(12) United States Patent
Kohn et al.

(10) Patent No.: US 8,563,257 B2
(45) Date of Patent: Oct. 22, 2013

(54) SENSITIVE AND RAPID METHODS OF USING CHIMERIC RECEPTORS TO IDENTIFY AUTOIMMUNE DISEASE AND ASSESS DISEASE SEVERITY

(75) Inventors: Leonard Kohn, Woodinville, WA (US); Jim Brown, Athens, OH (US); David Scholl, Athens, OH (US); Yunsheng Li, Athens, OH (US); Giorgio Napolitano, Pescara (IT)

(73) Assignee: Diagnostic Hybrids, Inc., Athens, OH (US)

( * ) Notice: Subject to any disclaimer, the term of this patent is extended or adjusted under 35 U.S.C. 154(b) by 748 days.

(21) Appl. No.: 12/483,689

(22) Filed: Jun. 12, 2009

(65) Prior Publication Data

US 2009/0325177 A1   Dec. 31, 2009

Related U.S. Application Data

(60) Continuation-in-part of application No. PCT/US2008/011027, filed on Sep. 24, 2008, which is a continuation-in-part of application No. 11/906,189, filed on Oct. 1, 2007, now Pat. No. 8,293,879, which is a continuation-in-part of application No. 10/996,961, filed on Nov. 24, 2004, now abandoned, which is a division of application No. 09/539,735, filed on Mar. 30, 2000, now Pat. No. 6,852,546.

(51) Int. Cl.
   *G01N 33/53*   (2006.01)

(52) U.S. Cl.
   USPC .......................................................... 435/7.2

(58) Field of Classification Search
   None
   See application file for complete search history.

(56) References Cited

U.S. PATENT DOCUMENTS

| 4,609,622 A | 9/1986 | Kohn et al. ...................... 435/29 |
| 6,524,580 B1 * | 2/2003 | Donovan ...................... 424/94.5 |
| 6,852,546 B1 * | 2/2005 | Brown ........................... 436/506 |

FOREIGN PATENT DOCUMENTS

| WO | WO99/16902 | 4/1999 |
| WO | WO 99/16902 | * 4/1999 |

OTHER PUBLICATIONS

Akamizu et al., 'Chimeric studies of the extracellular domain of the rat thyrotropin (TSH) receptor: amino acids (268-304) in the TSH receptor are involved in ligand high affinity binding, but not in TSH receptor-specific signal transduction' *Endocr J* 40:363-372 (1993).
Abaza et al., 'Effects of amino acid substitutions outside an antigenic site on protein binding to monoclonal antibodies of predetermined specificity obtained by peptide immunization: demonstration with region 94-100 (antigenic site 3) of myoglobin,' *J. Prot. Chem.* 11(5):433-444 (1992).
Baldet et al., 'Thyroid stimulating antibody: an index of thyroid stimulation in Graves' disease', *Acta Endocrinol.(Copenh)* 116:7-12 (1987).
Bidey et al., 'Characterization of thyroid-stimulating immunoglobulin-induced cyclic AMP accumulation in the rat thyroid cell strain FRTL-5: potentiation by forskolin and calibration against reference preparations of thyrotrophin', *J. Endocrinol.*, 105:7-15 (1985).
Boshart et al., 'A very strong enhancer is located upstream of an immediate early gene of human cytomegalovirus', *Cell* 41:521-530 (1985).
Botero and Brown, 'Bioassay of thyrotropin receptor antibodies with Chinese hamster ovary cells transfected with recombinant human thyrotropin receptor: Clinical utility in children and adolescents with Graves disease', *J. Pediatr.* 132:612-618 (1998).
Colman et al., 'Effects of amino acid sequence changes on antibody-antigen interactions,' *Research in Immunology* 145(1):33-36 (1994).
Da Costa et al., 'Modulation of graves' disease autoantibody stimulation of recombinant human thyrotrophin receptor', *Clinica. Chimica. Acata.*, 336: 39-44 (2003).
Dallas et al., 'Thyrotropin (TSH) receptor antibodies (TSHrAb) can inhibit TSH-mediated cyclic adenosine 3',5'-monophosphate production in thyroid cells by either blocking TSH binding or affecting a step subsequent to TSH binding', *Endocrinologu*, 137(8): 332-339 (1996).
Dijkema, et al., 'Cloning and expression of the chromosomal immune interferon gene of the rat', *EMBO J.* 4(3):761-767 (1985).
Evans et al., 'Development of a luminescent bioassay for thyroid stimulating antibodies', *J. Clin. Endocrinol. Metabol.*, 84:374-377 (1999).
Federman, Thyroid, in Dale and Federman (eds.), *Scientific American Medicine*, 3:1-6, Scientific American, New York, NY, (1997).
Gorman et al, 'The Rous sarcoma virus long terminal repeat is a strong promoter when introduced into a variety of eukaryotic cells by DNA-mediated transfection', *Proc. Natl. Acad. Sci. USA* 79:6777-6781 (1982).
Inui et al., 'Increase of thyroid stimulating activity in Graves' immunoglobulin-G by high polyethylene glycol concentrations using procine thyroid cell assay', *Thyroid*, 8(4): 319-325 (1998).

(Continued)

Primary Examiner — Michael Pak
(74) Attorney, Agent, or Firm — Medlen & Carroll, LLP

(57) ABSTRACT

The present invention provides methods and compositions useful in the diagnosis and management of autoimmune diseases. In particular, the present invention provides improved methods and compositions for the diagnosis and management of Graves' disease. The methods of the present invention not only avoids the need for radioactivity and are much simpler, economical, and rapid than methods traditionally used for the diagnosis of Graves' disease, but also improve upon the sensitivity and detection abilities of previous luciferase-based autoantibody detection assays. Such improvements are based upon the superior performance of assays comprising a chimeric TSH receptor in the presence of a glucocorticoid including, but not limited to, dexamethasone.

28 Claims, 20 Drawing Sheets

(56) References Cited

OTHER PUBLICATIONS

Kakinuma et al., 'The human thyrotropin (TSH) receptor in a TSH binding inhibition assay for TSH receptor autoantibodies', *J. Clin. Endocrinol. Metabol.*, 82: 2129-2134 (1997).

Kasagi et al., 'A sensitive and practical assay for thyroid-stimulating antibodies using crude immunoglobulin fractions precipitated with polyethylene glycol', *J. Clin. Endocrinol. Metabol.*, 62:855-862 (1986).

Kim et al., 'Use of the human elongation factor 1α promoter as a versatile and efficient expression system', *Gene* 91:217-223 (1990).

Kim et al., 'The prevalance and clinical significance of blocking thyrotropin receptor antibodies in untreated hyperthyroid graves' disease' *Thyroid* 10:579-586 (2000).

Kosugi et al., 'Mechanisms by which low salt condition increases sensitivity of thyroid stimulating antibody assay', *Endocrinol.*, 125:410-417 (1989).

Kung et al., 'Epitope mapping of TSH receptor-blocking antibodies in graves' disease that appear during pregnancy,' *J Clin Endocrinol Metab* 86:3647-3653 (2001).

Lederman et al., 'A single amino acid substitution in a common African allele of the CD4 molecule ablates binding of the monoclonal antibody, OKT4,' *Molec. Immunolo.* 28:1171-1181 (1991).

Maniatis, et al., 'Regulation of inducible and tissue-specific gene expression', *Science* 236: 1237-1245 (1987).

McKenzie and Zakarija, 'Clinical review 3: the clinical use of thyrotropin receptor antibody measurements', *J. Clin. Endocrinol. Metabol.*, 69:1093-1096 (1989).

Michelangeli et al., 'Measurement of thyroid stimulating immunoglobulins in a new cell line transfected with a functional human TSH receptor (JPO9 cells), compared with an assay using FRTL-5 cells', *Clin. Endocrinol.*,40:645-652 (1994).

Mizushima and Nagata, 'pEF-BOS, a powerful mammalian expression vector', *Nuc. Acids. Res.*, 18:5322 (1990).

Morganthaler et al., 'Application of a bioassay with CHO cells for the routine detection of stimulating and blocking autoantibodies to the TSH-receptor', *Horm. Metab. Res.*, 30: 162-168 (1998).

Ochi et al., 'Augmentative effect of polyethylene glycol, polyvinyl alcohol and dextran on thyroid-stimulating antibodystimulated cAMP production in FRTL-5 cells and CHO cells expressing human TSH receptor,' *Hormone. Res.* 53(1):20-25 (2000).

Rapoport et al, 'Clinical experience with a human thyroid cell bioassay for thyroid-stimulating immunoglobulin' *J. Clin. Endocrinol. Metabol.*, 58:332-338 (1984).

Sambrook et al., Molecular Cloning: A Laboratory Manual, 2nd ed., Cold Spring Harbor Laboratory Press, New York (1989), pp. 16.6-16.8.

Tahara et al., 'Immunoglobulins from graves' disease patients interact with different sites on TSH receptor/LH/CG receptor chimeras than either TSH or immunoglobulins from idiopathic myxedema patients,' *Biochem Biophys Res Comm* 179:70-77 (1991).

Uetsuki et al., 'Isolation and characterization of the human chromosomal gene for polypeptide chain elongation factor 1-α', *J. Biol. Chem.*, 264:5791-5798 (1989).

Vitti et al., 'Detection of thyroid-stimulating antibody using Chinese hamster ovary cells transfected with cloned human thyrotropin receptor', *J. Clin. Endocrinol. Metabol.*, 76:499-503 (1993).

Voss, et al., 'The role of enhancers in the regulation of cell-type-specific transcriptional control', *Trends Biochem. Sci.*, 11:287-289 (1986).

Yokoyama et al, 'Heterogeneity of graves' immunoglobulin g: comparison of thyrotropin receptor antibodies in serum mad in culture supernatants of lymphocytes transformed by epstein-barr virus infection', *J. Clin. Endocrinol. Metabol.*, 64:215-218 (1987).

\* cited by examiner

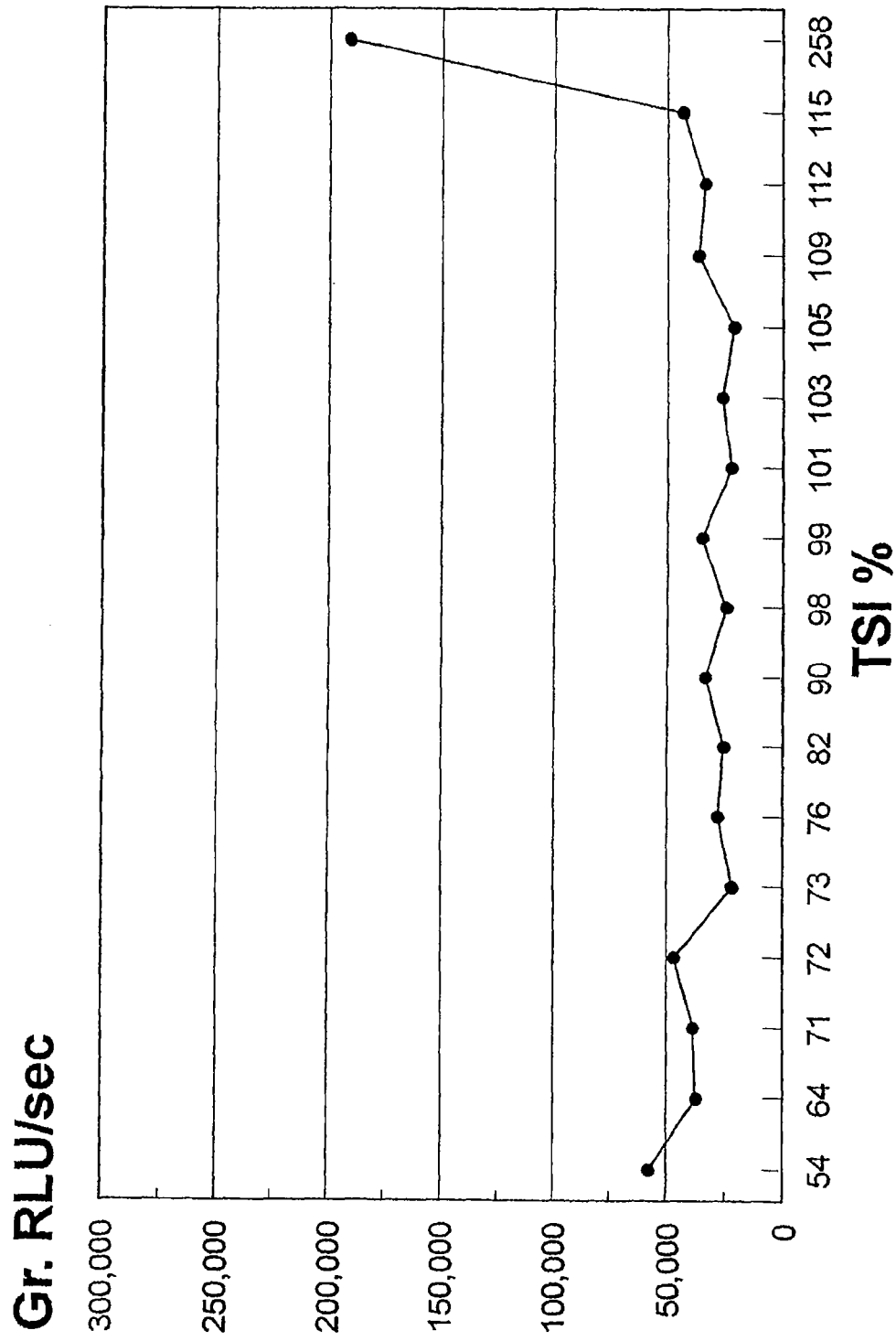

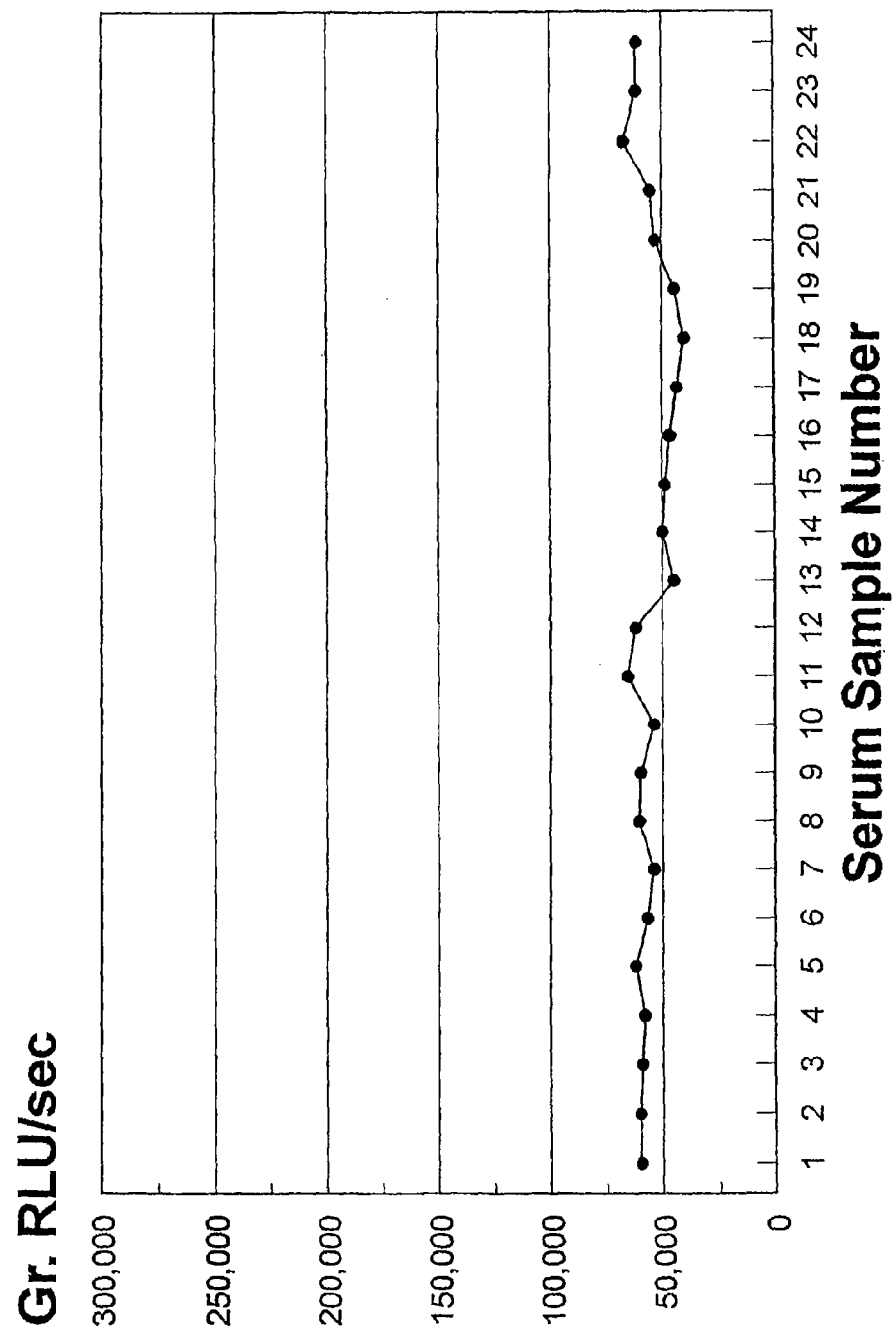

```
GGCGATTTCGGAGGATGGAGAAATAGCCCCGAGTCCCGTGGAAAATGAGGCCGGCGGAC
TTGCTGCAGCTGGTGCTGCTGCTCGACCTGCCCAGGGACCTGGGCGGAATGGGGTGTTC
GTCTCCACCCTGCGAGTGCCATCAGGAGGAGGACTTCAGAGTCACCTGCAAGGATATTC
AACGCATCCCCAGCTTACCGCCCAGTACGCAGACTCTGAAGCTTATTGAGACTCACCTG
AGAACTATTCCAAGTCATGCATTTTCTAATCTGCCCAATATTTCCAGAATCTACGTATC
TATAGATGTGACTCTGCAGCAGCTGGAATCACACTCCTTCTACAATTTGAGTAAAGTGA
CTCACATAGAAATTCGGAATACCAGGAACTTAACTTACATAGACCCTGATGCCCTCAAA
GAGCTCCCCCTCCTAAAGTTCCTTGGCATTTTCAACACTGGACTTAAAATGTTCCCTGA
CCTGACCAAAGTTTATTCCACTGATATATTCTTTATACTTGAAATTACAGACAACCCTT
ACATGACGTCAATCCCTGTGAATGCTTTTCAGGGACTATGCAATGAAACCTTGACACTG
AAGCTGTACAACAATGGCTTTACTTCAGTCCAAGGATATGCTTTCAATGGGACAAAGCT
GGATGCTGTTTACCTAAACAAGAATAAATACCTGACAGTTATTGACAAAGATGCATTTG
GAGGAGTATACAGTGGACCAAGCTTGCTGGACGTGTCTCAAACCAGTGTCACTGCCCTT
CCATCCAAAGGCCTGGAGCACCTGAAGGAACTGATAGCAAGAAACACCTGGACTCTTAA
GACACTGCCCTCCAAAGAAAAATTCACGAGCCTCCTGGTCGCCACGCTGACCTACCCCA
GCCACTGCTGCGCCTTCAG*TAATTTGCCGAAGAAGAACAGAATTTTTCATTTTCCAT
TTTTGAAAACTTCTCCAAACAATGCGAAAGCACAGTTAGAAAAGCAGATAACGAGACGC
TTTATTCCGCCATCTTTGAGGAGAATGAACTCAGTGGCTGGGATGAGCTCAAAAACCCC
CAGGAAGAGACTCTACAAGCTTTTGACAGCCATTATGACTACACCATATGTGGGGACAG
TGAAGACATGGTGTGTACCCCAAGTCCGATGAGTTCAACCCGTGTGAAGACATAATGG
GCTACAAGTTCCTGAGAATTGTGGTGTGGTTCGTTAGTCTGCTGGCTCTCCTGGGCAAT
GTCTTTGTCCTGCTTATTCTCCTCACCAGCCACTACAAACTGAACGTCCCCCGCTTTCT
CATGTGCAACCTGGCCTTTGCGGATTTCTGCATGGGGATGTACCTGCTCCTCATCGCCT
CTGTAGACCTCTACACTCACTCTGAGTACTACAACCATGCCATCGACTGGCAGACAGGC
CCTGGGTGCAACACGGCTGGTTTCTTCACTGTCTTTGCAAGCGAGTTATCGGTGTATAC
GCTGACGGTCATCACCCTGGAGCGCTGGTATGCCATCACCTTCGCCATGCGCCTGGACC
GGAAGATCCGCCTCAGGCACGCATGTGCCATCATGGTTGGGGCTGGGTTTGCTGCTTC
CTTCTCGCCCTGCTTCCTTTGGTGGGAATAAGTAGCTATGCCAAAGTCAGTATCTGCCT
GCCCATGGACACCGAGACCCCTCTTGCTCTGGCATATATTGTTTTTGTTCTGACGCTCA
ACATAGTTGCCTTCGTCATCGTCTGCTGCTGTTATGTGAAGATCTACATCACAGTCCGA
AATCCGCAGTACAACCCAGGGGACAAAGATACCAAAATTGCCAAGAGGATGGCTGTGTT
GATCTTCACCGACTTCATATGCATGGCCCCAATCTCATTCTATGCTCTGTCAGCAATTC
TGAACAAGCCTCTCATCACTGTTAGCAACTCCAAAATCTTGCTGGTACTCTTCTATCCA
CTTAACTCCTGTGCCAATCCATTCCTCTATGCTATTTTCACCAAGGCCTTCCAGAGGGA
TGTGTTCATCCTACTCAGCAAGTTTGGCATCTGTAAACGCCAGGCTCAGGCATACCGGG
GGCAGAGGGTTCCTCCAAAGAACAGCACTGATATTCAGGTTCAAAAGGTTACCCACGAC
ATGAGGCAGGGTCTCCACAACATGGAAGATGTCTATGAACTGATTGAAAACTCCCATCT
AACCCCAAAGAAGCAAGGCCAAATCTCAGAAGAGTATATGCAAACGGTTTTGTAAGTTA
ACACTACACTACTCACAATGGTAGGGGAACTTACAAAATAATAGTTTCTTGAATATGCA
TTCCAATCCCATGACACCCCCAAC
```

FIGURE 8

| | | |
|---|---|---|
| human PGH al | 1 | ---------------atgtgtatggctcaataaaattac |
| HEK M13R seq | 1 | attcgcccttgagctcatgtgtatggctcaataaaattac |
| human PGH al | 25 | gtacaaagtgacagcgtactctcttttcatgggctgacct |
| HEK M13R seq | 41 | gtacaaagtgacagcgtactctcttttcatgggctgacct |
| human PGH al | 65 | tgtcgtcaccatcacctgaaaatggctccaaacaaaaatg |
| HEK M13R seq | 81 | tgtcgtcaccatcacctgaaaatggctccaaacaaaaatg |
| human PGH al | 105 | acctaagggttgaaacaagataagatcaaattgacgtcat |
| HEK M13R seq | 121 | acctaagggttgaaacaagataagatcaaattgacgtcat |
| human PGH al | 145 | ggtaaaaattgacgtcatggtaattacaccaagtaccctt |
| HEK M13R seq | 161 | ggtaaaaattgacgtcatggtaattacaccaagtaccctt |
| human PGH al | 185 | caatcattggatggaatttcctgttgatcccagggcttag |
| HEK M13R seq | 201 | caatcattggatggaatttcctgttgatcccagggcttag |
| human PGH al | 225 | atgcaggtggaaacactctgctggtataaaagcaggtgac |
| HEK M13R seq | 241 | atgcaggtggaaacactctgctggtataaaagcaggtgag |
| human PGH al | 265 | gacttcattatactgcagttactgagaactcataagacga |
| HEK M13R seq | 281 | gacttcattatactgcagttactgagaactcataagacga |
| human PGH al | | ------------------ |
| HEK M13R seq | 321 | agatctaagggcgaatt |

FIGURE 9

A
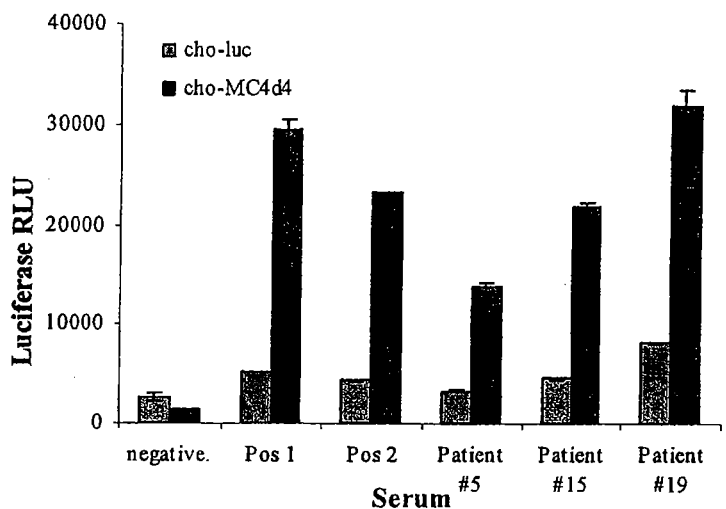
B
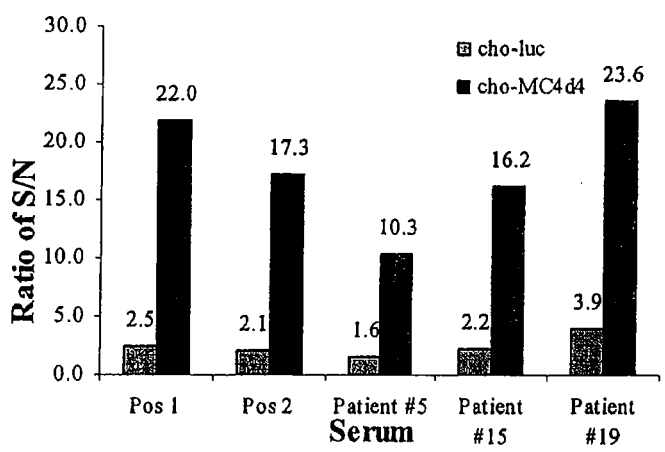
Figure 10

C
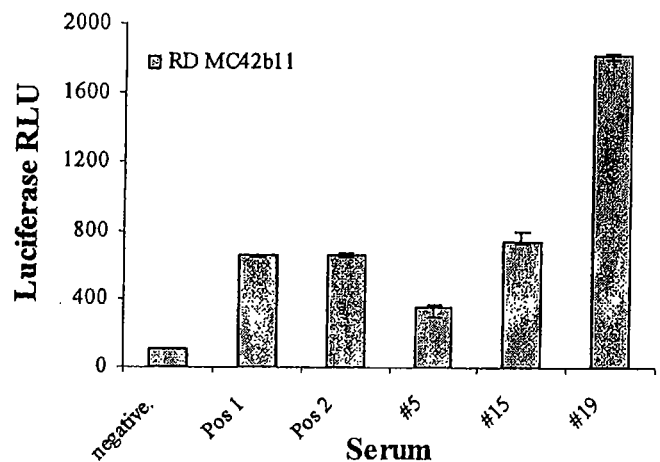
D
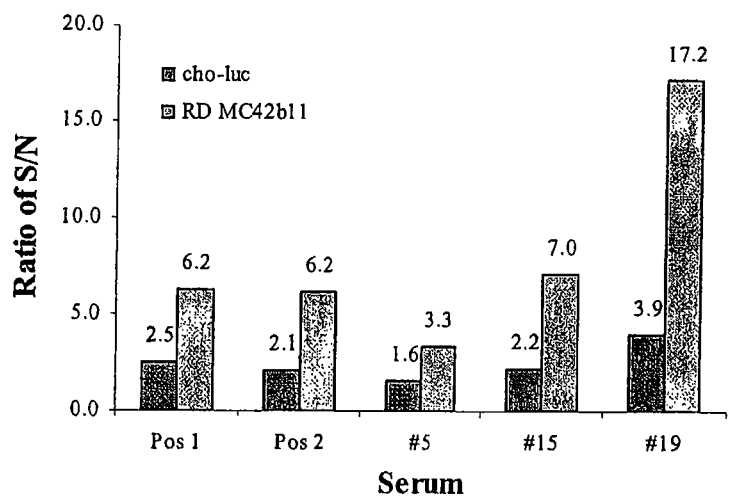
Figure 10 (Cont'd)

A
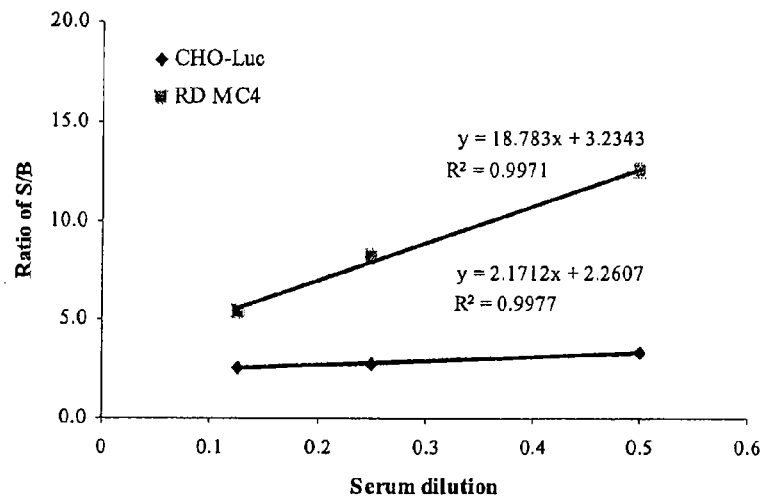
B
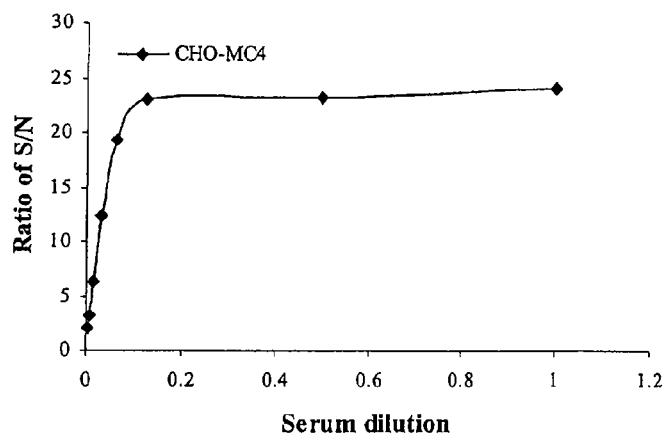
C
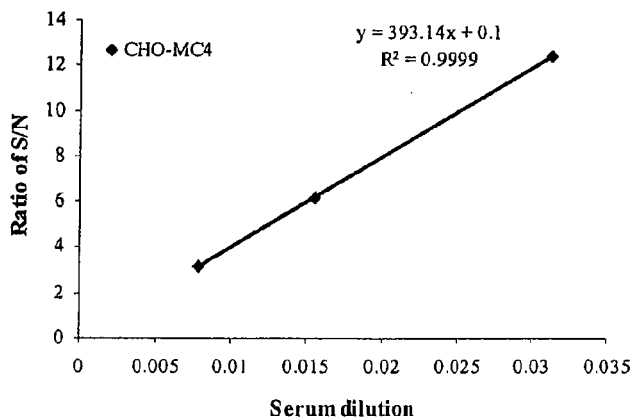
Figure 11

A 1 qtliatssys lkklpsrekf anlldatlty pshccafrnv ptkeqnfsfs isknfpkqce
61 stvrkqnnet lypaifaesg qsgwd

B 1 ililntknll hiedgafrnl prlkylsicn tgiiefpdlt qifsseahfi lelcdnlrmt
61 tipqnafrgm snesltlkly kngfedihsh afngtklnql ilkdnknlrr ihndalrgai
121 gpdvldisst aleslpsygl eaiqvlngms syslkrlppl dkfsslleav lty

C 1 mlpallplll pallpgaggg rcpqrcactq palrcptppp garpaparas fthlpvkvip
61 shafeglrda fiieisqsds lerieasafd slpalseili lntknllhie dgafrnlprl
121 kylsicntgi iefpdltqif sseahfilel cdnlrmttip qnafqgmsne sltlklykng
181 fedihshafn gtklnqlilk dnknlrrihn dalrgatgpd vldisstale slpsygleai
241 qvlnamssys lkrlppldkf sslleavlty pshccafqnl rtekqnslls ifdnfskqce
301 stmrkpasev fyrdassnts lwpaekhmyp letgeceafpy systvfyede mtgfdfeydf
361 cqpkiltctp epdafnpced ilgysflrvl iwfinilala gnfivllvli tshykltvpr
421 flmcnlsfad fcmglyllli asvdaqtsgq yynhaidwqt gsgcstagff tvfaselsvy
481 tltvitierw htityamqld rklrlrhavp imlggwvfsi liavlpllgv ssymkvsicl
541 pmdietglsq ayillilmln viaflvicac yikiyvavqn pelvaankdt kiakrmaili
601 ftdftcmapi sffaisaaik vplitvtnsk illvlfypvn scanpflyai ftkafqrdff
661 llmsklgcck sraelyrvny fsaytpnckn gssapgpska sqallllsas eklcktrrst
721 kksqpecq

D 1 mgrrvpalrq llvlamlvlk qsqlhspels gsrcpepcdc apdgalrcpg praglarl

E 1 mgrpslalrl llallllppp apllwalrpa pcpepcscpp dgalrcpgpq aglsrlslty
61 lpikvipsqa frglneviki eisqsdslek ieanafdnll nlseiliqnt knlvhieaga
121 ftnlprlkyl sicntgihkl pdvtkifsse fnfileicdn lhittiprna fqgmnnesit
181 lklygngfee iqshafngtt lislelkena rlekmhndaf rgatgpsild isstklqalp
241 tyglesiqtl iatssyslkk lpsrekftnl ldatltypsh ccafrnlptn eqnfsfsifk
301 nfskqcesta rrpnnetlys aifaeselsg wdydygfclp ktlqcapepd afnpcedimg
361 ynflrvliwl inilaitgnv tvlfvlltsr ykltvprflm cnlsfadfcm glyllliasv
421 daqtkgqyyn haidwqtgsg csaagfftvf aselsvytlt vitlerwhti tyaiqldqkl
481 rlkhaipvml ggwlfstlia vlplvgvsny mkvsiclpmd vestlsqvyi ltililnvma
541 fiiicacyik iyfavqnpel matnkdtkia kkmavliftd ftcmapisff aisaafkvpl
601 itvtnskvll vlfypvnsca npflyaiftk afqrdfflll skfgcckyra elyrrkdfsa
661 yisnckngft gsnkpsrstf klttlqcqys avldktcyke c

Figure 15

Appln. No.: 12/483,689
Inventor: Kohn, et al
Reply to Missing Parts of 07/01/2009
Replacement Sheet 3 of 5
Attorney Docket No.: DHI-13989

| Replicates | Specimen Type |
|---|---|
| A | Positive Control |
| B | Reference Control |
| C | Negative Control |
| D | Italy #2077 |
| E | Italy #1399 |
| F | Italy #3063 |
| G | NA |
| H | Italy #1427 |
| I | Italy #2765 |
| J | Italy #1450 |
| K | Italy #4497 |
| L | Italy #4442 |
| M | Italy #4637 |
| N | Blank |
| O | Blank |
| P | Blank |

SEQUENCE LISTING

<160> NUMBER OF SEQ ID NOS: 10

<210> SEQ ID NO 1
<211> LENGTH: 45
<212> TYPE: DNA
<213> ORGANISM: Artificial Sequence
<220> FEATURE:
<223> OTHER INFORMATION: Synthetic

<400> SEQUENCE: 1
gagctcatgt gtatggctca ataaaattac gtacaaagtg acagc        45

<210> SEQ ID NO 2
<211> LENGTH: 45
<212> TYPE: DNA
<213> ORGANISM: Artificial Sequence
<220> FEATURE:
<223> OTHER INFORMATION: Synthetic

<400> SEQUENCE: 2
agatcttcgt cttatgagtt ctcagtaact gcagtataat gaagt        45

<210> SEQ ID NO 3
<211> LENGTH: 2324
<212> TYPE: DNA
<213> ORGANISM: Artificial Sequence
<220> FEATURE:
<223> OTHER INFORMATION: Synthetic

<400> SEQUENCE: 3

```
ggcgatttcg gaggatggag aaatagcccc gagtcccgtg gaaaatgagg ccggcggact      60
tgctgcagct ggtgctgctg ctcgacctgc ccagggacct gggcggaatg gggtgttcgt     120
ctccaccctg cgagtgccat caggaggagg acttcagagt cacctgcaag gatattcaac     180
gcatccccag cttaccgccc agtacgcaga ctctgaagct tattgagact cacctgagaa     240
ctattccaag tcatgcattt tctaatctgc caatatttc cagaatctac gtatctatag     300
atgtgactct gcagcagctg gaatcacact ccttctacaa tttgagtaaa gtgactcaca     360
tagaaattcg gaataccagg aacttaactt acatagaccc tgatgccctc aaagagctcc     420
ccctcctaaa gttccttggc attttcaaca ctggacttaa aatgttccct gacctgacca     480
aagtttattc cactgatata ttctttatac ttgaaattac agacaaccct acatgacgt      540
caatccctgt gaatgctttt cagggactat gcaatgaaac cttgacactg aagctgtaca     600
acaatggctt tacttcagtc caaggatatg ctttcaatgg gacaaagctg gatgctgttt     660
acctaaacaa gaataaatac ctgacagtta ttgacaaaga tgcatttgga ggagtataca     720
gtggaccaag cttgctggac gtgtctcaaa ccagtgtcac tgcccttcca tccaaaggcc     780
tggagcacct gaaggaactg atagcaagaa acacctggac tcttaagaca ctgccctcca     840
aagaaaaatt cacgagcctc ctggtcgcca cgctgaccta ccccagccac tgctgcgcct     900
tcagtaattt gccgaagaaa gaacagaatt tttcatttc catttttgaa aacttctcca     960
aacaatgcga agcacagtt agaaaagcag ataacgagac gctttattcc gccatctttg    1020
aggagaatga actcagtggc tgggatgagc tcaaaaaccc caggaagag actctacaag     1080
cttttgacag ccattatgac tacaccatat gtggggacag tgaagacatg gtgtgtaccc    1140
ccaagtccga tgagttcaac ccgtgtgaag acataatggg ctacaagttc ctgagaattg    1200
tggtgtggtt cgttagtctg ctggctctcc tgggcaatgt cttgtcctg cttattctcc     1260
tcaccagcca ctacaaactg aacgtccccc gctttctcat gtgcaacctg gcctttgcgg    1320
atttctgcat ggggatgtac ctgctcctca tcgcctctgt agacctctac actcactctg    1380
agtactacaa ccatgccatc gactggcaga caggccctgg gtgcaacacg ctggtttct     1440
tcactgtctt tgcaagcgag ttatcggtgt atacgctgac ggtcatcacc ctggagcgct    1500
ggtatgccat caccttcgcc atgcgcctgg accggaagat ccgcctcagg cacgcatgtg    1560
ccatcatggt tgggggctgg gtttgctgct tccttctcgc cctgcttcct ttggtgggaa    1620
taagtagcta tgccaaagtc agtatctgcc tgcccatgga caccgagacc ctcttgctc     1680
tggcatatat tgttttgtt ctgacgctca acatagttgc cttcgtcatc gtctgctgct    1740
gttatgtgaa gatctacatc acagtccgaa atccgcagta caacccaggg gacaaagata    1800
ccaaaattgc caagaggatg ctgtgttga tcttcaccga cttcatatgc atggccccaa     1860
tctcattcta tgctctgtca gcaattctga caagcctct catcactgtt agcaactcca    1920
aaatcttgct ggtactcttc tatccactta actcctgtgc caatccattc ctctatgcta    1980
ttttcaccaa ggccttccag agggatgtgt tcatcctact cagcaagttt ggcatctgta    2040
aacgccaggc tcaggcatac cggggggcaga gggttcctcc aaagaacagc actgatattc    2100
aggttcaaaa ggttacccac gacatgaggc agggtctcca acatggaa gatgtctatg      2160
aactgattga aaactcccat ctaaccccaa agaagcaagg ccaaatctca gaagagtata    2220
tgcaaacggt tttgtaagtt aacactacac tactcacaat ggtaggggaa cttacaaaat    2280
aatagtttct tgaatatgca ttccaatccc atgacacccc caac                     2324
```

-continued

```
<210> SEQ ID NO 4
<211> LENGTH: 304
<212> TYPE: DNA
<213> ORGANISM: Homo sapiens

<400> SEQUENCE: 4
atgtgtatgg ctcaataaaa ttacgtacaa agtgacagcg tactctcttt tcatgggctg      60
accttgtcgt caccatcacc tgaaaatggc tccaaacaaa aatgacctaa gggttgaaac     120
aagataagat caaattgacg tcatggtaaa aattgacgtc atggtaatta caccaagtac     180
ccttcaatca ttggatggaa tttcctgttg atcccagggc ttagatgcag gtggaaacac     240
tctgctggta taaaagcagg tgacgacttc attatactgc agttactgag aactcataag     300
acga                                                                  304

<210> SEQ ID NO 5
<211> LENGTH: 337
<212> TYPE: DNA
<213> ORGANISM: Artificial Sequence
<220> FEATURE:
<223> OTHER INFORMATION: Synthetic

<400> SEQUENCE: 5
attcgccctt gagctcatgt gtatggctca ataaaattac gtacaaagtg acagcgtact      60
ctcttttcat gggctgacct tgtcgtcacc atcacctgaa aatggctcca aacaaaaatg     120
acctaagggt tgaaacaaga taagatcaaa ttgacgtcat ggtaaaaatt gacgtcatgg     180
taattacacc aagtacccttcaatcattgg atggaatttc tgttgatcc cagggcttag     240 atgcaggtgg aaacactctg ctggtataaa agcaggtgag gacttcatta tactgcagtt     300
actgagaact cataagacga agatctaagg gcgaatt                              337

<210> SEQ ID NO 6
<211> LENGTH: 85
<212> TYPE: PRT
<213> ORGANISM: Bos taurus

<400> SEQUENCE: 6

Gln Thr Leu Ile Ala Thr Ser Ser Tyr Ser Leu Lys Lys Leu Pro Ser
1               5                   10                  15

Arg Glu Lys Phe Ala Asn Leu Leu Asp Ala Thr Leu Thr Tyr Pro Ser
            20                  25                  30

His Cys Cys Ala Phe Arg Asn Val Pro Thr Lys Glu Gln Asn Phe Ser
        35                  40                  45

Phe Ser Ile Ser Lys Asn Phe Pro Lys Gln Cys Glu Ser Thr Val Arg
    50                  55                  60

Lys Gln Asn Asn Glu Thr Leu Tyr Pro Ala Ile Phe Ala Glu Ser Gly
65                  70                  75                  80

Gln Ser Gly Trp Asp
            85

<210> SEQ ID NO 7
<211> LENGTH: 173
<212> TYPE: PRT
<213> ORGANISM: Bos taurus

<400> SEQUENCE: 7

Ile Leu Ile Leu Asn Thr Lys Asn Leu Leu His Ile Glu Asp Gly Ala
1               5                   10                  15

Phe Arg Asn Leu Pro Arg Leu Lys Tyr Leu Ser Ile Cys Asn Thr Gly
            20                  25                  30
```

-continued

```
Ile Ile Glu Phe Pro Asp Leu Thr Gln Ile Phe Ser Ser Glu Ala His
        35                  40                  45

Phe Ile Leu Glu Leu Cys Asp Asn Leu Arg Met Thr Thr Ile Pro Gln
 50                  55                  60

Asn Ala Phe Arg Gly Met Ser Asn Glu Ser Leu Thr Leu Lys Leu Tyr
 65                  70                  75                  80

Lys Asn Gly Phe Glu Asp Ile His Ser His Ala Phe Asn Gly Thr Lys
                 85                  90                  95

Leu Asn Gln Leu Ile Leu Lys Asp Asn Lys Asn Leu Arg Arg Ile His
            100                 105                 110

Asn Asp Ala Leu Arg Gly Ala Ile Gly Pro Asp Val Leu Asp Ile Ser
            115                 120                 125

Ser Thr Ala Leu Glu Ser Leu Pro Ser Tyr Gly Leu Glu Ala Ile Gln
130                 135                 140

Val Leu Asn Gly Met Ser Ser Tyr Ser Leu Lys Arg Leu Pro Pro Leu
145                 150                 155                 160

Asp Lys Phe Ser Ser Leu Leu Glu Ala Val Leu Thr Tyr
                165                 170
```

<210> SEQ ID NO 8
<211> LENGTH: 728
<212> TYPE: PRT
<213> ORGANISM: Bos taurus

<400> SEQUENCE: 8

```
Met Leu Pro Ala Leu Leu Pro Leu Leu Pro Ala Leu Leu Pro Gly
 1               5                  10                  15

Ala Gly Gly Arg Cys Pro Gln Arg Cys Ala Cys Thr Gln Pro Ala
                 20                  25                  30

Leu Arg Cys Pro Thr Pro Pro Gly Ala Arg Pro Ala Pro Ala Arg
            35                  40                  45

Ala Ser Phe Thr His Leu Pro Val Lys Val Ile Pro Ser His Ala Phe
 50                  55                  60

Glu Gly Leu Arg Asp Ala Phe Ile Ile Glu Ile Ser Gln Ser Asp Ser
 65                  70                  75                  80

Leu Glu Arg Ile Glu Ala Ser Ala Phe Asp Ser Leu Pro Ala Leu Ser
                 85                  90                  95

Glu Ile Leu Ile Leu Asn Thr Lys Asn Leu Leu His Ile Glu Asp Gly
            100                 105                 110

Ala Phe Arg Asn Leu Pro Arg Leu Lys Tyr Leu Ser Ile Cys Asn Thr
            115                 120                 125

Gly Ile Ile Glu Phe Pro Asp Leu Thr Gln Ile Phe Ser Ser Glu Ala
130                 135                 140

His Phe Ile Leu Glu Leu Cys Asp Asn Leu Arg Met Thr Thr Ile Pro
145                 150                 155                 160

Gln Asn Ala Phe Gln Gly Met Ser Asn Glu Ser Leu Thr Leu Lys Leu
                165                 170                 175

Tyr Lys Asn Gly Phe Glu Asp Ile His Ser His Ala Phe Asn Gly Thr
            180                 185                 190

Lys Leu Asn Gln Leu Ile Leu Lys Asp Asn Lys Asn Leu Arg Arg Ile
            195                 200                 205

His Asn Asp Ala Leu Arg Gly Ala Thr Gly Pro Asp Val Leu Asp Ile
        210                 215                 220

Ser Ser Thr Ala Leu Glu Ser Leu Pro Ser Tyr Gly Leu Glu Ala Ile
225                 230                 235                 240
```

```
Gln Val Leu Asn Ala Met Ser Tyr Ser Leu Lys Arg Leu Pro Pro
                245                 250                 255

Leu Asp Lys Phe Ser Ser Leu Leu Glu Ala Val Leu Thr Tyr Pro Ser
            260                 265                 270

His Cys Cys Ala Phe Gln Asn Leu Arg Thr Glu Lys Gln Asn Ser Leu
        275                 280                 285

Leu Ser Ile Phe Asp Asn Phe Ser Lys Gln Cys Glu Ser Thr Met Arg
    290                 295                 300

Lys Pro Ala Ser Glu Val Phe Tyr Arg Asp Ala Ser Ser Asn Thr Ser
305                 310                 315                 320

Leu Trp Pro Ala Glu Lys His Met Tyr Pro Leu Glu Thr Gly Glu Glu
                325                 330                 335

Ala Phe Pro Tyr Ser Tyr Ser Thr Val Phe Tyr Glu Asp Glu Met Thr
            340                 345                 350

Gly Phe Asp Phe Glu Tyr Asp Phe Cys Gln Pro Lys Ile Leu Thr Cys
        355                 360                 365

Thr Pro Glu Pro Asp Ala Phe Asn Pro Cys Glu Asp Ile Leu Gly Tyr
    370                 375                 380

Ser Phe Leu Arg Val Leu Ile Trp Phe Ile Asn Ile Leu Ala Leu Ala
385                 390                 395                 400

Gly Asn Phe Ile Val Leu Leu Val Leu Ile Thr Ser His Tyr Lys Leu
                405                 410                 415

Thr Val Pro Arg Phe Leu Met Cys Asn Leu Ser Phe Ala Asp Phe Cys
            420                 425                 430

Met Gly Leu Tyr Leu Leu Leu Ile Ala Ser Val Asp Ala Gln Thr Ser
        435                 440                 445

Gly Gln Tyr Tyr Asn His Ala Ile Asp Trp Gln Thr Gly Ser Gly Cys
    450                 455                 460

Ser Thr Ala Gly Phe Phe Thr Val Phe Ala Ser Glu Leu Ser Val Tyr
465                 470                 475                 480

Thr Leu Thr Val Ile Thr Ile Glu Arg Trp His Thr Ile Thr Tyr Ala
                485                 490                 495

Met Gln Leu Asp Arg Lys Leu Arg Leu Arg His Ala Val Pro Ile Met
            500                 505                 510

Leu Gly Gly Trp Val Phe Ser Ile Leu Ile Ala Val Leu Pro Leu Leu
        515                 520                 525

Gly Val Ser Ser Tyr Met Lys Val Ser Ile Cys Leu Pro Met Asp Ile
    530                 535                 540

Glu Thr Gly Leu Ser Gln Ala Tyr Ile Leu Leu Ile Leu Met Leu Asn
545                 550                 555                 560

Val Ile Ala Phe Leu Val Ile Cys Ala Cys Tyr Ile Lys Ile Tyr Val
                565                 570                 575

Ala Val Gln Asn Pro Glu Leu Val Ala Ala Asn Lys Asp Thr Lys Ile
            580                 585                 590

Ala Lys Arg Met Ala Ile Leu Ile Phe Thr Asp Phe Thr Cys Met Ala
        595                 600                 605

Pro Ile Ser Phe Phe Ala Ile Ser Ala Ala Ile Lys Val Pro Leu Ile
    610                 615                 620

Thr Val Thr Asn Ser Lys Ile Leu Leu Val Leu Phe Tyr Pro Val Asn
625                 630                 635                 640

Ser Cys Ala Asn Pro Phe Leu Tyr Ala Ile Phe Thr Lys Ala Phe Gln
                645                 650                 655

Arg Asp Phe Phe Leu Leu Met Ser Lys Leu Gly Cys Cys Lys Ser Arg
            660                 665                 670
```

```
Ala Glu Leu Tyr Arg Val Asn Tyr Phe Ser Ala Tyr Thr Pro Asn Cys
            675                 680                 685

Lys Asn Gly Ser Ser Ala Pro Gly Pro Ser Lys Ala Ser Gln Ala Leu
        690                 695                 700

Leu Leu Leu Ser Ala Ser Glu Lys Leu Cys Lys Thr Arg Arg Ser Thr
705                 710                 715                 720

Lys Lys Ser Gln Pro Glu Cys Gln
                725

<210> SEQ ID NO 9
<211> LENGTH: 58
<212> TYPE: PRT
<213> ORGANISM: Bos taurus

<400> SEQUENCE: 9

Met Gly Arg Arg Val Pro Ala Leu Arg Gln Leu Leu Val Leu Ala Met
1               5                   10                  15

Leu Val Leu Lys Gln Ser Gln Leu His Ser Pro Glu Leu Ser Gly Ser
            20                  25                  30

Arg Cys Pro Glu Pro Cys Asp Cys Ala Pro Asp Gly Ala Leu Arg Cys
        35                  40                  45

Pro Gly Pro Arg Ala Gly Leu Ala Arg Leu
    50                  55

<210> SEQ ID NO 10
<211> LENGTH: 701
<212> TYPE: PRT
<213> ORGANISM: Bos taurus

<400> SEQUENCE: 10

Met Gly Arg Pro Ser Leu Ala Leu Arg Leu Leu Ala Leu Leu Leu Leu
1               5                   10                  15

Leu Pro Pro Pro Ala Pro Leu Leu Trp Ala Leu Arg Pro Ala Pro Cys
            20                  25                  30

Pro Glu Pro Cys Ser Cys Pro Pro Asp Gly Ala Leu Arg Cys Pro Gly
        35                  40                  45

Pro Gln Ala Gly Leu Ser Arg Leu Ser Leu Thr Tyr Leu Pro Ile Lys
    50                  55                  60

Val Ile Pro Ser Gln Ala Phe Arg Gly Leu Asn Glu Val Ile Lys Ile
65                  70                  75                  80

Glu Ile Ser Gln Ser Asp Ser Leu Glu Lys Ile Glu Ala Asn Ala Phe
                85                  90                  95

Asp Asn Leu Leu Asn Leu Ser Glu Ile Leu Ile Gln Asn Thr Lys Asn
            100                 105                 110

Leu Val His Ile Glu Ala Gly Ala Phe Thr Asn Leu Pro Arg Leu Lys
        115                 120                 125

Tyr Leu Ser Ile Cys Asn Thr Gly Ile His Lys Leu Pro Asp Val Thr
    130                 135                 140

Lys Ile Phe Ser Ser Glu Phe Asn Phe Ile Leu Glu Ile Cys Asp Asn
145                 150                 155                 160

Leu His Ile Thr Thr Ile Pro Arg Asn Ala Phe Gln Gly Met Asn Asn
                165                 170                 175

Glu Ser Ile Thr Leu Lys Leu Tyr Gly Asn Gly Phe Glu Glu Ile Gln
            180                 185                 190

Ser His Ala Phe Asn Gly Thr Thr Leu Ile Ser Leu Glu Leu Lys Glu
        195                 200                 205
```

```
Asn Ala Arg Leu Glu Lys Met His Asn Asp Ala Phe Arg Gly Ala Thr
            210                 215                 220
Gly Pro Ser Ile Leu Asp Ile Ser Ser Thr Lys Leu Gln Ala Leu Pro
225                 230                 235                 240
Thr Tyr Gly Leu Glu Ser Ile Gln Thr Leu Ile Ala Thr Ser Ser Tyr
                    245                 250                 255
Ser Leu Lys Lys Leu Pro Ser Arg Glu Lys Phe Thr Asn Leu Leu Asp
            260                 265                 270
Ala Thr Leu Thr Tyr Pro Ser His Cys Cys Ala Phe Arg Asn Leu Pro
            275                 280                 285
Thr Asn Glu Gln Asn Phe Ser Phe Ser Ile Phe Lys Asn Phe Ser Lys
            290                 295                 300
Gln Cys Glu Ser Thr Ala Arg Arg Pro Asn Asn Glu Thr Leu Tyr Ser
305                 310                 315                 320
Ala Ile Phe Ala Glu Ser Glu Leu Ser Gly Trp Asp Tyr Asp Tyr Gly
                    325                 330                 335
Phe Cys Leu Pro Lys Thr Leu Gln Cys Ala Pro Glu Pro Asp Ala Phe
                340                 345                 350
Asn Pro Cys Glu Asp Ile Met Gly Tyr Asn Phe Leu Arg Val Leu Ile
            355                 360                 365
Trp Leu Ile Asn Ile Leu Ala Ile Thr Gly Asn Val Thr Val Leu Phe
370                 375                 380
Val Leu Leu Thr Ser Arg Tyr Lys Leu Thr Val Pro Arg Phe Leu Met
385                 390                 395                 400
Cys Asn Leu Ser Phe Ala Asp Phe Cys Met Gly Leu Tyr Leu Leu Leu
                405                 410                 415
Ile Ala Ser Val Asp Ala Gln Thr Lys Gly Gln Tyr Tyr Asn His Ala
            420                 425                 430
Ile Asp Trp Gln Thr Gly Ser Gly Cys Ser Ala Ala Gly Phe Phe Thr
            435                 440                 445
Val Phe Ala Ser Glu Leu Ser Val Tyr Thr Leu Thr Val Ile Thr Leu
            450                 455                 460
Glu Arg Trp His Thr Ile Thr Tyr Ala Ile Gln Leu Asp Gln Lys Leu
465                 470                 475                 480
Arg Leu Lys His Ala Ile Pro Val Met Leu Gly Gly Trp Leu Phe Ser
                485                 490                 495
Thr Leu Ile Ala Val Leu Pro Leu Val Gly Val Ser Asn Tyr Met Lys
            500                 505                 510
Val Ser Ile Cys Leu Pro Met Asp Val Glu Ser Thr Leu Ser Gln Val
            515                 520                 525
Tyr Ile Leu Thr Ile Leu Ile Leu Asn Val Met Ala Phe Ile Ile Ile
530                 535                 540
Cys Ala Cys Tyr Ile Lys Ile Tyr Phe Ala Val Gln Asn Pro Glu Leu
545                 550                 555                 560
Met Ala Thr Asn Lys Asp Thr Lys Ile Ala Lys Met Ala Val Leu
                565                 570                 575
Ile Phe Thr Asp Phe Thr Cys Met Ala Pro Ile Ser Phe Phe Ala Ile
            580                 585                 590
Ser Ala Ala Phe Lys Val Pro Leu Ile Thr Val Thr Asn Ser Lys Val
            595                 600                 605
Leu Leu Val Leu Phe Tyr Pro Val Asn Ser Cys Ala Asn Pro Phe Leu
            610                 615                 620
Tyr Ala Ile Phe Thr Lys Ala Phe Gln Arg Asp Phe Phe Leu Leu Leu
625                 630                 635                 640
```

-continued

```
Ser Lys Phe Gly Cys Cys Lys Tyr Arg Ala Glu Leu Tyr Arg Arg Lys
            645                 650                 655

Asp Phe Ser Ala Tyr Ile Ser Asn Cys Lys Asn Gly Phe Thr Gly Ser
            660                 665                 670

Asn Lys Pro Ser Arg Ser Thr Phe Lys Leu Thr Leu Gln Cys Gln
            675                 680                 685

Tyr Ser Ala Val Leu Asp Lys Thr Cys Tyr Lys Glu Cys
            690                 695             700
```

US 8,563,257 B2

SENSITIVE AND RAPID METHODS OF USING CHIMERIC RECEPTORS TO IDENTIFY AUTOIMMUNE DISEASE AND ASSESS DISEASE SEVERITY

STATEMENT OF RELATED APPLICATIONS

This is a Continuation-In-Part of co-pending application(s) PCT/US2008/011027 with an International Filing Date of Sep. 24, 2008 which is a Continuation-In-Part of U.S. patent application Ser. No. 11/906,189 (now issued as U.S. Pat. No. 8,293,879) filed on Oct. 1, 2007 which is a Continuation-In-Part of U.S. patent application Ser. No. 10/996,961 filed on Nov. 24, 2004 (now abandoned) which is a divisional of U.S. patent application Ser. No. 09/539,735 (now issued as U.S. Pat. No. 6,852,546) filed on Mar. 30, 2000.

FIELD OF THE INVENTION

The present invention provides methods and compositions useful in the diagnosis of autoimmune diseases. In particular, the present invention provides methods and compositions for use in the diagnosis and management of Graves' disease. For example, one composition comprises a chimeric thyroid stimulating hormone receptor having improved sensitivity and specificity for circulating thyroid stimulating immunoglobulin. Assays using such chimeric receptors can be optimized in the presence of a glucocorticoid.

BACKGROUND OF THE INVENTION

Graves' disease (also referred to as "diffuse toxic goiter"), is the leading cause of hyperthyroidism due to the action of autoantibodies that recognize and bind to receptors present on the thyroid gland, resulting in gland growth and over-production of thyroid hormone. Graves' disease is reported to be the most frequent cause of hyperthyroidism in childhood and adolescence (See, Boter and Brown, J. Pediatr. 132:612-618 (1998)).

Current diagnostic techniques for Graves' disease leave much to be desired. In general, the commercially available methods are cumbersome and laborious. Other methods require the administration of radioactive tracers to the person requiring a diagnosis. Most importantly, however, the vast majority of the presently used methods lack sufficient sensitivity such that a quick, accurate and cost-effective test can be performed.

What is still needed is an assay system for Graves' disease that is safe, easy to use, sensitive, specific, and cost-effective.

SUMMARY OF THE INVENTION

The present invention provides methods and compositions useful in the diagnosis and management of autoimmune diseases. In particular, the present invention provides methods and compositions for the diagnosis and management of Graves' disease. For example, one composition comprises a chimeric thyroid stimulating hormone receptor having improved sensitivity and specificity for circulating thyroid stimulating immunoglobulin. Assays using such chimeric receptors can be optimized in the presence of a glucocorticoid.

In one embodiment, the present invention contemplates a method, comprising: a) providing; i) a cell line comprising a stably transfected vector encoding a chimeric TSH receptor and a luciferase gene; ii) a serum sample derived from a patient suspected of having Graves' disease; and iii) a cell culture medium comprising a glucocorticoid; b) contacting the serum sample with the cell line and the medium under conditions such that the luciferase gene emits a detectable signal. In one embodiment, the method further comprises step c) measuring the signal intensity, wherein the intensity correlates with a thyrotropin stimulating hormone receptor autoantibody concentration present in the sample. In one embodiment, the glucocorticoid is selected from the group comprising dexamethasone, prednisone, hydrocortisone, fluticasone, or cortisone. In one embodiment, the contacting further comprises polyethylene glycol. In one embodiment, the chimeric TSH receptor comprises an amino acid sequence derived from rat chorionic hormone gonadotropin receptor. In one embodiment, the amino acid sequence comprises seventy three amino acids corresponding to amino acid residues 262-335 of a human TSH receptor amino acid sequence. In one embodiment, the serum sample comprises TSH receptor autoantibodies. In one embodiment, the autoantibodies comprise TSH stimulating autoantibodies. In one embodiment, the autoantibodies comprise TSH blocking antibodies.

In one embodiment, the present invention contemplates a kit comprising a chimeric TSH receptor and a luciferin-luciferase system capable of detecting serum TSH autoantibodies, wherein the system comprises a glucocorticoid. In one embodiment, the glucocorticoid is selected from the group comprising dexamethasone, prednisone, hydrocortisone, fluticasone, or cortisone. In one embodiment, the receptor comprises a human TSH receptor amino acid sequence. In one embodiment, the receptor comprises a rat chorionic hormone receptor amino acid sequence. In one embodiment, the rat receptor amino acid sequence comprises amino acid residues 262-335. In one embodiment, the kit further comprises a cell line capable of expressing the chimeric TSH receptor and the luciferin-luciferase system. In one embodiment, the kit further comprises polyethylene glycol. In one embodiment, the kit comprises a vector encoding the chimeric TSH receptor and a luciferase gene. In one embodiment, the vector further comprises a promoter in operably linked to the vector. In one embodiment, the promoter comprises a glycoprotein alpha subunit promoter. In one embodiment, the cell line comprises CHO cells. In one embodiment, the cell line comprises RD cells. In one embodiment, the kit further comprises an instruction sheet.

In one embodiment, the present invention provides methods for determining the presence of thyroid-stimulating autoantibodies in a test sample, comprising: a) providing i) a test sample suspected of containing thyroid-stimulating autoantibodies, ii) cultured cells comprising a glucocorticoid contained within a testing means, wherein the cells express a chimeric TSH receptor and a luciferin-luciferase system, and iii) polyethylene glycol; b) exposing the test sample to the cultured cells and polyethylene glycol under conditions such that thyroid-stimulating antibodies are detectable using a luciferin-luciferase system; and c) observing for the presence of detectable thyroid-stimulating antibodies. In one embodiment, the glucocorticoid is selected from the group comprising dexamethasone, prednisone, hydrocortisone, fluticasone, or cortisone. In one preferred embodiment, the cultured cells are selected from the group consisting of RDluc and CHOR-luc cells. In another embodiment, the observing is conducted using a luminometer. In further embodiments, the cAMP concentration is determined by the luciferin-luciferase system. In yet another embodiment, the methods further comprise a Growth Medium, while in other embodiments, the methods further comprise a Stimulation Medium. In some particularly preferred embodiments, the cultured cells are exposed to the Growth Medium prior to exposure of the test sample. In still further embodiments, the cultured cells are exposed to Stimulation Medium containing the test sample. In other particularly preferred embodiments, the Stimulation Medium comprises polyethylene glycol.

The present invention also provides methods for determining the presence of thyroid-stimulating autoantibodies in a test sample, comprising: a) providing; i) a test sample suspected of containing thyroid-stimulating autoantibodies, ii) cultured cells comprising a glucocorticoid, wherein the cells are selected from the group comprising RD-Rluc or CHO-Rluc cells contained within a testing means, wherein the cells express a chimeric TSH receptor, and iii) polyethylene glycol; b) exposing the test sample to the cultured cells and the polyethylene glycol under conditions such that thyroid stimulating antibodies are detectable using a luciferin-luciferase system; and c) observing for the presence of detectable thyroid-stimulating antibodies, wherein observing is conducted using a luminometer. In one embodiment, the glucocorticoid is selected from the group comprising dexamethasone, prednisone, hydrocortisone, fluticasone, or cortisone. In further embodiments, the cAMP concentration is determined by the luciferin-luciferase system. In some embodiments, the methods further comprise a Growth Medium, while in other embodiments the methods further comprise a Stimulation Medium. In some particularly preferred embodiments, the cultured cells are exposed to the Growth Medium prior to exposure of the test sample. In still other embodiments, the cultured cells are exposed to the Stimulation Medium containing the test sample. In yet other preferred embodiments, the Stimulation Medium comprises polyethylene glycol.

The present invention also provides methods for determining the presence of thyroid-stimulating autoantibodies in a test sample, comprising: a) providing; i) a test sample suspected of containing thyroid-stimulating autoantibodies, ii) cultured cells comprising a glucocorticoid, wherein the cells are selected from the group comprising RD-Rluc or CHO-Rluc cells contained within a testing means, wherein the cells express a chimeric TSH receptor, iii) Growth Medium, and iv) Stimulation Medium, wherein the Stimulation Medium comprises polyethylene glycol; b) exposing the cultured cells to Growth Medium to produce grown cells; c) exposing the test sample to the grown cells and Stimulation Medium under conditions such that thyroid-stimulating antibodies are detectable using the luciferin-luciferase system; and d) observing for the presence of detectable thyroid-stimulating antibodies, wherein said observing is conducted using a luminometer. In one embodiment, the glucocorticoid is selected from the group comprising dexamethasone, prednisone, hydrocortisone, fluticasone, or cortisone. In further embodiments, the cAMP concentration is determined by the luciferase-luciferin system.

In one embodiment, the present invention contemplates utilizing a clinical activity score (CAS) together with the various detection methods described herein. CAS is a validated scoring system, designed to distinguish inflammatory from noninflammatory Graves' orbitopathy (GO), and has a high predictive value for the outcome of immunosuppressive treatment in GO patients. It is based on the classical signs of inflammation: pain (2 points), redness (2 points), swelling (4 points) and impaired function (2 points). While the scoring can be done based on a single examination, it is preferred that two consecutive clinical examinations be done and then an "activity score" can be determined, ranging from 0 to 10 points. In some embodiments wherein CAS is determined in a single session, a modified CAS system is employed comprising seven items (the "7 item CAS"). The two methods differ in evaluation of visual acuity, diplopia and proptosis, which are part of the full 10 item CAS and are not included in the 7 item CAS. In studies performed before the introduction of the CAS scoring system, the ophthalmopathy index (OI) as proposed by Donaldson et al or the total eye score (TES) were developed. Secondary outcomes included the NOSPECS scheme (mnemonic for No signs or symptoms, Only signs, Soft tissue involvement, Proptosis, Extraocular muscle involvement, Corneal involvement and Sight loss, graded as O, A, B or C), diplopia, proptosis, optic neuropathy in either eye, subjective outcome measures (e.g. cosmetic response satisfaction), visual acuity, and local eye irritation.

BRIEF DESCRIPTION OF THE FIGURES

FIG. 6 shows the results for a group of samples with known TSI results using FRTL-5 cells (10 µl samples of LCA TSI specimens).

FIG. 7 shows the results for a group of normal samples (10 µl of AML "normal" specimens).

FIG. 8 shows one embodiment of a DNA sequence for a chimeric hTSH/mLH (Mc4) receptor comprising 2,324 base pairs and encoding 730 amino acids (SEQ ID NO: 3). The underlined letters are the human TSHR sequence. The letters in italics are the rat LHR sequence. "*" (T) in the rat LHR sequence is a G in the wild type sequence. This G to T mutation resulted in an amino acid change from Arginine to Serine.

FIG. 9 shows one embodiment of a 236 nucleotide glycoprotein alpha subunit promoter comprising a cyclic AMP (cAMP) regulatory element (CRE) (AF401991) sequence alignment (SEQ ID NO: 4) with a GPH promoter amplified by PCR from HEK cells (SEQ ID NO: 5). Shaded areas indicate homology. Non-highlighted areas designate the flanking region of the promoter in the plasmid.

FIG. 10A: Luciferase assay on CHO-RLuc and CHO-RMc4 cell lines induced with TSI negative and positive sera.

FIG. 10B: The ratio of S/N derived from the luciferase assay on CHO-RLuc and CHO-RMc4 cell lines induced with TSI negative and positive sera.

FIG. 10C: Luciferase assay on CHO-RLuc and RD-RMc4 cell lines induced with TSI negative and positive sera.

FIG. 10D: The ratio of S/N derived from the luciferase assay on CHO-RLuc and RD-RMc4 cell lines induced with TSI negative and positive sera.

FIG. 10E: The ratio of S/N derived from the luciferase assay on CHO-RLuc, CHO-RMc4 and RD-RMc4 cell lines induced with TSI negative and positive sera.

FIG. 11 presents exemplary data showing signal-to-noise (S/N) ratios for RD-RMc4 and CHO-RLuc cell lines in response to a serum dilution profile.

FIG. 11A: The S/N ratio from the luciferase assay on CHO-RLuc and RD-RMc4 cell lines induced with same dilutions of the TSI positive serum.

FIG. 11B: The S/N ratio from the luciferase assay on CHO-RMc4 cell line induced with dilution of the TSI positive serum.

FIG. 11C: The S/N ratio from the luciferase assay on CHO-RMc4 cell line induced with higher dilutions of the TSI positive

FIG. 15 presents exemplary amino acid sequences: luteinizing hormone receptor:

FIG. 15A: *Callithrix jacchus* (white-tufted-ear marmoset) CAJ57370 (SEQ ID NO: 6)

FIG. 15B: *Coturnix japonica* (Japanese quail) AAB32614 (SEQ ID NO: 7)

FIG. 15C: *Gallus gallus* (chicken) NP_990267 (SEQ ID NO: 8)

FIG. 15D: *Mus musculus* (mouse) AAB24402 (SEQ ID NO: 9)

FIG. 15E: *Bos taurus* (cow) NP_776806 (SEQ ID NO: 10)

DEFINITIONS

Figure 1:
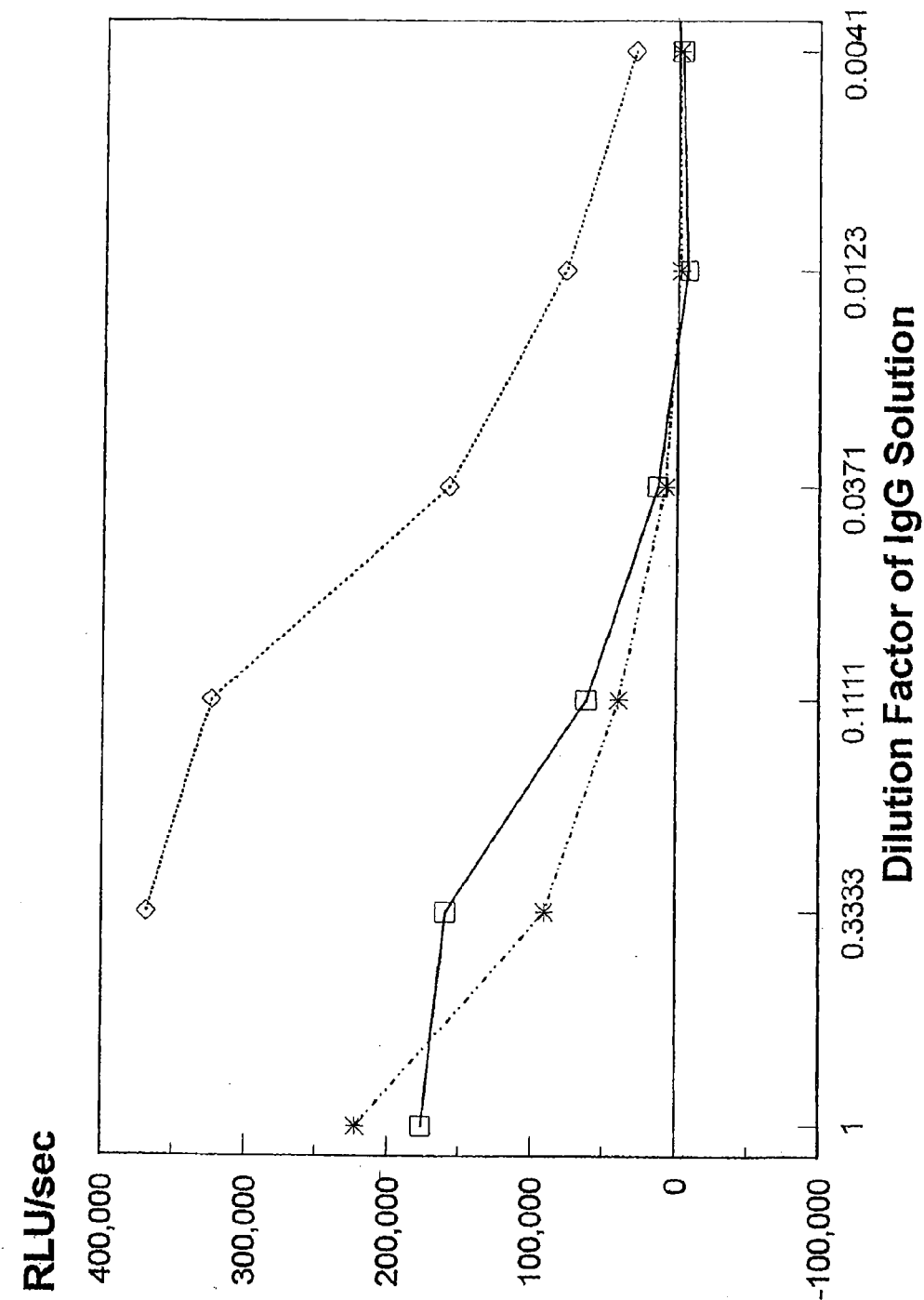
FIG. 1 provides results for serial 3-fold dilutions of three Graves' disease IgG samples (from untreated Graves' patients), in assays utilizing Stimulation Medium containing 6% PEG-8000.

The terms "sample" and "specimen" in the present specification and claims are used in their broadest sense. On the one hand, they are meant to include a specimen or culture. On the other hand, they are meant to include both biological and environmental samples. These terms encompass all types of samples obtained from humans and other animals, including but not limited to, body fluids (e.g., blood), as well as solid tissue.

Biological samples may be animal, including human, fluid or tissue, food products and ingredients such as dairy items, vegetables, meat and meat by-products, and waste. These examples are not to be construed as limiting the sample types applicable to the present invention.

As used herein, the term "kit" is used in reference to a combination of reagents and other materials.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen.

As used herein, the terms "antigen fragment" and "portion of an antigen" are used in reference to a portion of an antigen. Antigen fragments or portions may occur in various sizes, ranging from a small percentage of the entire antigen to a large percentage, but not 100% of the antigen. However, in situations where at least a portion of an antigen is specified, it is contemplated that the entire antigen may be present. It is contemplated that antigen fragments or portions, may, but are not required to comprise an "epitope" recognized by an antibody. Antigen fragments or portions also may or may not be immunogenic.

As used herein, the term "autoantibodies" refers to antibodies that are capable of reacting against an antigenic constituent of an individual's own tissue or cells (e.g., the antibodies recognize and bind to "self" antigens).

As used herein, the term "immunoassay" is used in reference to any method in which antibodies are used in the detection of an antigen. It is contemplated that a range of immunoassay formats be encompassed by this definition, including but not limited to, direct immunoassays, indirect immunoassays, and "sandwich" immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the method of the present invention.

As used herein, the term "capture antibody" refers to an antibody that is used to bind an antigen and thereby permit the recognition of the antigen by a subsequently applied antibody. For example, the capture antibody may be bound to a microtiter well and serve to bind an antigen of interest present in a sample added to the well. Another antibody (termed the "primary antibody") is then used to bind to the antigen-antibody complex, in effect to form a "sandwich" comprised of antibody-antigen-antibody complex. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of an antibody-antigen-antibody-antibody complex. Again, appropriate reporter reagents are then added to detect the labelled antibody. Any number of additional antibodies may be added as desired. These antibodies may also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, a reporter reagent may be a calorimetric substance attached to an enzymatic substrate. Upon binding of antibody and antigen, the enzyme acts on its substrate and causes the production of a color. Other reporter reagents include, but are not limited to, fluorogenic and radioactive compounds or molecules. This definition also encompasses the use of biotin and avidin-based compounds (e.g., including, but not limited to, neutravidin and streptavidin) as part of the detection system. In one embodiment of the present invention, biotinylated antibodies may be used in the present invention in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, luminescent and enzymatic reactions will be used with the present invention. The signal may be assessed quantitatively as well as qualitatively.

As used herein the term "signal intensity" refers to magnitude of the signal strength wherein the intensity correlates with the amount of reaction substrate. For example, a luciferin-luciferase system generates a signal intensity that correlates with the amount of cAMP generated by thyrotropin stimulating hormone receptor autoantibodies.

The term "correlates" indicates that a phenomenon (e.g. signal intensity) is related to another phenomenon (e.g anti-body concentration, or disease severity). The relationship is typically a parallel relationship (e.g. as one increases, the other increases).

As used herein, the term "clinical activity" means ongoing signs and symptoms of inflammation and pathology (pain, red eyes, double vision, etc.).

As used herein, the term "luciferin-luciferase system" refers to any process or method that allows the contact of luciferin and luciferase in the presence of a substrate (i.e., for example, cAMP) under conditions such that the resulting luminesence may be detected. Such a system may be comprised within a transfected host cell encoded by a vector, or provided in separate kit containers whereby the contents may be mixed together.

As used herein, the term "solid support" is used in reference to any solid material to which reagents such as antibodies, antigens, and other compounds may be attached. For example, in the ELISA method, the wells of microtiter plates often provide solid supports. Other examples of solid supports include microscope slides, coverslips, beads, particles, cell culture flasks, as well as many other items.

As used herein, the term "cell staining" is used in reference to methods used to label or stain cells to enhance their visualization. This staining or labelling may be achieved through the use of various compounds, including but not limited to, fluorochromes, enzymes, gold, and iodine. It is contemplated that the definition encompasses such methods as "in situ chromogenic assays," in which a test (i.e., an assay) is conducted on a sample in situ. It is also contemplated that the in situ chromogenic assay will involve the use of an immunoassay (i.e., an ELISA).

As used herein, the term "Growth Medium" refers to a culture medium formulated to contain various growth factors including, but not limited to, vitamins, amino acids, co-factors, and any other appropriate nutrients to enhance growth and replication of cells in culture.

As used herein, the term "Stimulation Medium" refers to a medium formulated to be deficient in certain constituents (e.g., sodium chloride), in order to enhance the stimulation of by TSH and/or TSI, thereby increasing the resulting signal (e.g., cAMP and/or luciferase).

As used herein, the term "Starvation Medium" refers to a medium formulated to be deficient in at least one growth factors included in the Growth Medium. In preferred embodiments, this medium contains only the salts and glucose necessary to sustain cells for a short period of time.

As used herein, the term "organism" and "microorganism," are used to refer to any species or type of microorganism, including but not limited to viruses and bacteria, including *rickettsia* and *chlamydia*. Thus, the term encompasses, but is not limited to DNA and RNA viruses, as well as organisms within the orders Rickettsiales and Chlamydiales.

As used herein, the term "culture," refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "mixed cell culture," refers to a mixture of two types of cells. In some preferred embodiments, the cells are cell lines that are not genetically engineered, while in other preferred embodiments the cells are genetically engineered cell lines. In some embodiments, the one or more of the cell types is "permissive" (i.e., virus is capable of replication and spread from cell to cell within the culture). The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used herein, the term "suitable for the detection of intracellular parasites," refers to cell cultures that can be successfully used to detect the presence of an intracellular parasite in a sample. In preferred embodiments, the cell cultures are capable of maintaining their susceptibility to infection and/or support replication of the intracellular parasite. It is not intended that the present invention be limited to a particular cell type or intracellular parasite.

As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

As used herein, the terms "monolayer," "monolayer culture," and "monolayer cell culture," refer to cells that have adhered to a substrate and grow as a layer that is one cell in thickness. Monolayers may be grown in various vessels including, but not limited to, flasks, tubes, coverslips (e.g., shell vials), roller bottles, etc. Cells may also be grown attached to microcarriers, including but not limited to beads.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein, the term "obligate intracellular parasite," (or "obligate intracellular organism) refers to any organism which requires an intracellular environment for its survival and/or replication. Obligate intracellular parasites include viruses, as well as many other organisms, including certain bacteria including, but not limited to, most members of the orders: i) Rickettsiales: for example, *Coxiella, Rickettsia* and *Ehrlichia*; and ii) Chlamydiales: for example, *C. trachomatis, C. psittaci*. The term "intracellular parasite," refers to any organism that may be found within the cells of a host animal, including but not limited to obligate intracellular parasites briefly described above. For example, intracellular parasites include organisms such as *Brucella, Listeria, Mycobacterium* (e.g., *M. tuberculosis* and *M. leprae*), and *Plasmodium*, as well as Rochalimea.

As used herein, the term "antimicrobial," is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorgamsms.

As used herein, the terms "chromogenic compound," and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator," encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator," and "oxidation-reduction indicator," encompasses all compounds commonly used for detection of oxidation/reduction potentials (i.e., "eH") including, but not limited to various types or forms of tetrazolium, resazurin, and methylene blue.

As used herein, the term "inoculating suspension," or "inoculant," is used in reference to a suspension which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "primary isolation," refers to the process of culturing organisms directly from a sample. As used herein, the term "isolation," refers to any cultivation of organisms, whether it be primary isolation or any subsequent cultivation, including "passage," or "transfer," of stock cultures of organisms for maintenance and/or use.

As used herein, the term "presumptive diagnosis," refers to a preliminary diagnosis which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis," is used to refer to a final diagnosis in which the etiologic agent of the patient's disease has been identified. The term "definitive identification" is used in reference to the final identification of an organism to the genus and/or species level.

The term "recombinant DNA molecule," as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene," refers to a DNA sequence comprising the coding region of a gene or, in other words, the DNA sequence which encodes a gene product. The coding region may be present in either a cDNA or genomic DNA form. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers and/or promoters, splice junctions, intervening sequences, polyadenylation signals, etc. or a combination of both endogenous and exogenous control elements.

The term "transcription unit," as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element," as used herein refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The terms "reporter gene construct," or "reporter gene vector," as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene," refers to an oligonucleotide having a sequence encoding a gene product (typically an enzyme) which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding β-galactosidase (lacZ, the bacterial chloramphenicol acetyltransferase (cat) genes, firefly luciferase genes and genes encoding β-glucuronidase (GUS).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986), and Maniatis, et al., supra (1987)). For example, the SV40 early gene enhancer is very active in a wide variety of cell types from many mammalian species and has been widely used for the expression of proteins in mammalian cells (Dijkema, et al., EMBO J. 4:761 (1985)). Two other examples of promoter/enhancer elements active in a broad range of mammalian cell types are those from the human elongation factor 1α gene (Uetsuki et al., J. Biol. Chem., 264:5791 (1989); Kim et al., Gene 91:217 (1990); and Mizushima and Nagata, Nuc. Acids. Res., 18:5322 (1990)) and the long terminal repeats of the Rous sarcoma virus (Gorman et al., Proc. Natl. Acad. Sci. USA 79:6777 (1982)), and the human cytomegalovirus (Boshart et al., Cell 41:521 (1985)).

The term "promoter/enhancer," denotes a segment of DNA which contains sequences capable of providing both promoter and enhancer functions (for example, the long terminal repeats of retroviruses contain both promoter and enhancer functions). The enhancer/promoter may be "endogenous," or "exogenous," or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals," on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989), pp. 16.7-16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site," or "poly A sequence," as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7). This 237 bp fragment is contained within a 671 bp BamHI/PstI restriction fragment.

The term "genetically engineered cell line," refers to a cell line that contains heterologous DNA introduced into the cell line by means of molecular biological techniques (i.e., recombinant DNA technology).

The term "vector" as used herein, refers to a nucleotide sequence comprising at least a promoter and a gene of interest. Such a gene of interest may encode an amino acid sequence for the purpose of expressing the amino acid sequence (i.e., for example, a TSH receptor amino acid sequence). A vector has the capability of becoming integrated into foreign DNA to form a stable transfected cell.

The term "stable transfection," or "stably transfected," refers to the introduction and integration of foreign DNA into the genome of the transfected cell.

The term "stable transfectant," refers to a cell which has stably integrated foreign DNA into the genomic DNA.

The term "stable transfection" (or "stably transfected"), refers to the introduction and integration of foreign DNA into the genome of the transfected cell. The term "stable transfectant," refers to a cell which has stably integrated foreign DNA into the genomic DNA.

The term "RDluc" refers to an RD cell line having been stably transfected with a luciferase gene. Further, RD-Rluc refers to a RD cell line having been stably transfected with a luciferase gene and that displays an exogenous receptor (i.e., for example, a TSH receptor including but not limited to, a Mc4 receptor).

The term "CHOluc" refers to a CHO cell line having been stably transfected with a luciferase gene. Further, CHO-Rluc refers to a CHO cell line having been stably transfected with a luciferase gene and that displays an exogenous receptor (i.e., for example, a TSH receptor including but not limited to, a wild-type receptor). Alternatively, CHO-RMc4luc refers to a CHO cell line having been stably transfected with a luciferase gene that displays a chimeric receptor. (i.e., for example, a TSH receptor that comprises amino acid sequences derived from a rat chorionic gonadotrophin receptor).

The term "selectable marker," as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprt cell lines. A review of the use of selectable markers in mammalian cell lines is provided in Sambrook et al., supra at pp. 16.9-16.15.

The terms "nucleic acid molecule encoding," "DNA sequence encoding," and "DNA encoding," refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The terms "confluent" or "confluency" as used herein in reference to an adherent cell line define a condition wherein cells throughout a culture are in contact with each other creating what appears to be a continuous sheet or "monolayer" of cells.

The terms "cytopathic effect" or "CPE" as used herein describe changes in cellular structure (i.e., a pathologic effect) resulting from external agents such viruses. Common cytopathic effects include cell destruction, syncytia (i.e., fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

The abbreviation "ONPG," represents o-Nitrophenyl-13-D-Galactopyranoside. ONPG is a substrate for the enzyme β-galactosidase (β-gal). The reaction between ONPG and (β-gal produces a yellow product which can be quantified spectrophotometrically at 405 nm.

The abbreviation "X-gal," represents the chemical compound 5-bromo-4-chloro-3-indolyl-(3-D-galactopyranoside, a substrate for the enzyme β-galactosidase. The reaction between X-gal and β-galactosidase results in the formation of a blue precipitate which is visually discernable.

The term "hybriwix," represents a product of Diagnostic Hybrids, Inc., Athens, Ohio which allows for quantification of certain viral DNA in an infected monolayer of cells by DNA hybridization. "DNA hybridization" is the annealing of two complementary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}$I, a radioisotope which can be detected and quantified with a gamma counter.

The phrase "plaque reduction assay," or "PRA," as used herein describes a standard method used to determine efficacy of anti-viral drugs by enumerating a decrease in plaque formation in a cell monolayer exposed to a drug. A "plaque" is a defined area of "CPE." It is usually the result of infection of the cell monolayer with a single infectious virus which then replicates and spreads to adjacent cells of the monolayer. A plaque may also be referred to as a "focus of viral infection."

The term "permissive" as used herein describes the sequence of interactive events between a virus and its putative host cell. The process begins with viral adsorption to the host cell surface and ends with release of infectious virions. A cell is "permissive" if it readily permits the spread of virus to other cells. Many methods are available for the determination of the permissiveness of a given cell line, including but not limited to, plaque reduction assays, comparisons of the production and/or quantitation of viral proteins based on results obtained from gel electrophoresis, relative comparisons using hybridization analysis to analyze DNA or RNA content, etc.

The term "susceptible," as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on," as used herein describes the act of transferring an aqueous solution of suspended cells into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer," results from the "seed on" process.

The phrase "seed in," as used herein describes the mixing of two or more aqueous solutions of suspended tissue culture cells, each cell suspension having different cellular properties, and transfer of such mixture of cells into a vessel which is stored for a sufficient period of time to allow the suspended cells to settle out by gravity and attach in a relatively uniform manner such that the distribution of any single cell type is indicative of the relative ratio of the cells in the original mixture.

The term "starts," as used herein refers to the reporter cells which represent a primary infection of virus. The virus infects a reporter cell (a genetically engineered cell) and induces the expression of the reporter gene. A reporter cell can be non-permissive (i.e. permissiveness of the reporter cells is not required) and still produce starts.

The term "chimeric" as used herein, refers to any nucleic and/or amino acid sequence containing portions from two or more different species. A protein may be chimeric if the primary amino acid sequence contains portions from two or more different species (i.e., for example, an hTSH/rLH-R or RMc4). A protein may also be chimeric if the primary amino acids sequence contains portions from two or more different proteins, whether from the same species or different species. A protein may also be chimeric if the quaternary amino acid structure contains proteins from two or more different species. Further, a nucleic acid may be chimeric if the primary nucleotide sequence contains portions from two or more different species. A nucleic acid may also be chimeric if the primary nucleotide sequence contains portions from two or more different proteins, whether from the same species or different species.

The term, "glucocorticoid" as used herein, refers to any compound any corticosteroid that increases gluconeogenesis, raising the concentration of liver glycogen and blood glucose; the group includes, but is not limited to, dexamethasone, prednisone, hydrocortisone, fluticasone, cortisol, cortisone, or corticosterone.

Graves' opthalmopathy, also known as Graves' thyroid-associated or dysthyroid "orbitopathy," is an autoimmune inflammatory disorder affecting the orbit of the eye. In mild disease, patients present with eyelid retraction. In moderate disease, patients present with myopathy. In more severe and active disease, mass effects and cicatricial changes occur within the orbit. Disease may progress to a restrictive myopathy which restricts eye movements and an optic neuropathy. With enlargement of the extraocular muscle at the orbital apex, the optic nerve is at risk of compression. The orbital fat or the stretching of the nerve due to increased orbital volume may also lead to optic nerve damage.

In some embodiments, serum samples are diluted (e.g. a series of dilutions) and assayed in order to generate a serum dilution curve. In one embodiment, the shape of serum dilution curves are compared to generate a comparative reactivity profile (CRP). For example, in one embodiment, the present invention contemplates generating a CRP by comparing the shape of a serum dilution curves from a patient pre- (e.g. before initiation of therapy) and post- (after initiation of therapy) drug therapy/treatment. In this manner, one can compare the read out (e.g. luciferase activity) to determine reduction of the thyroid-stimulating immunoglobulin (TSI or TSAb) in the serum; by comparing them, one can conclude whether the therapy is effective not.

In some embodiments, the present invention contemplates using the assays and methods herein described to assess clinical activity, and/or the severity of disease, and/or Graves' orbitopathy. In one embodiment, the present invention contemplates a method, comprising: a) providing: i) a cell line comprising a stably transfected recombinant plasmid vector encoding a chimeric human TSH receptor and a reporter gene; ii) a cell culture medium compatible with said cell line; and iii) a serum sample derived from a patient suspected of having Graves' disease; b) contacting the serum sample with the cell line and the medium (e.g. the cells are in the medium) under conditions such that a reporter gene emits a detectable signal upon induction by a TSH receptor-specific stimulating auto-antibody (in one embodiment, the signal intensity reflects the antibody concentration). In one embodiment, said chimeric receptor comprises a portion of a human chorionic gonadotropin receptor. In one embodiment, said method further comprises step c) measuring the activity of the expressed reporter gene, wherein said activity correlates with clinical activity. In one embodiment, said method further comprises step c) measuring the activity of the expressed reporter gene, wherein said activity correlates with the clinical severity of Graves' disease. In one embodiment, said clinical severity is assessed, measured or determined on the basis of diplopia, proptosis, visual acuity, ocular motility, optic neuropathy, or extra-ocular muscle thickness as determined by either computed tomographic or magnetic resonance imaging scans. In one embodiment, said clinical severity is measured on the basis of the NOSPECS score. In one embodiment, said method further comprises step c) measuring the activity of the expressed reporter gene, wherein said activity correlates with Graves' orbitopathy. In one embodiment, the thyrotropin stimulating hormone receptor autoantibody concentration correlates with clinical activity, and/or with the clinical severity of Graves' disease. The clinical severity may be assessed in a variety of ways. In one embodiment, the clinical severity is assessed on the basis of diplopia, proptosis, visual acuity, ocular motility, optic neuropathy, or extra-ocular muscle thickness as determined by either computed tomographic or magnetic resonance imaging scans. In one embodiment, said clinical severity is measured on the basis of the NOSPECS score. In one embodiment, the thyrotropin stimulating hormone receptor autoantibody concentration correlates with Graves' orbitopathy. In one embodiment, said culture medium contains a glucocorticoid. In one embodiment, said reporter gene is luciferase.

In one embodiment, diluted (e.g. with a buffer or other aqueous solution) and undiluted serum samples are employed. In one embodiment, the present invention contemplates a method, comprising: a) providing: i) a cell line comprising a stably transfected recombinant plasmid vector encoding a chimeric human TSH receptor and a reporter gene; ii) a cell culture medium compatible with said cell line; and iii) an undiluted serum sample and a diluted serum sample from a patient suspected of having Graves' disease; b) contacting the undiluted serum sample and diluted serum sample with the cell line and the medium under conditions such that a reporter gene emits a detectable signal upon induction by a TSH receptor-specific stimulating auto-antibody (in one embodiment, the signal intensity reflects the antibody concentration). In one embodiment, said chimeric receptor comprises a portion of a human chorionic gonadotropin receptor. In one embodiment, said method further comprises step c) comparing the activity of the expressed reporter gene from said undiluted sample with said diluted sample. In one embodiment, said activity from undiluted and diluted serum demonstrates a comparative reactivity profile indicative of clinical activity. In one embodiment, said activity from undiluted and diluted serum demonstrates a comparative reactivity profile indicative of severity of Graves' disease. In one embodiment, said activity from undiluted and diluted serum demonstrates a comparative reactivity profile indicative for Graves' orbitopathy. In one embodiment, said culture medium contains a glucocorticoid. In one embodiment, said reporter gene is luciferase.

In one embodiment, the present invention contemplates testing pre- and post-drug therapy serum samples. In one embodiment, the present invention contemplates a method, comprising: a) providing: i) a cell line comprising a stably transfected recombinant plasmid vector encoding a chimeric human TSH receptor and a reporter gene; ii) a cell culture medium compatible with said cell line; iii) a first undiluted serum sample obtained from a patient having Graves' disease prior to being treated with drug therapy (pre-treatment); and iv) a second undiluted serum sample obtained from a patient having Graves' disease after being treated with drug therapy (post-treatment); b) diluting a portion of said first serum to create a diluted first serum sample; and contacting said undiluted first serum sample and said diluted first serum sample with the cell line and the medium under conditions such that a reporter gene emits a detectable signal upon induction by a TSH receptor-specific stimulating auto-antibody (in one embodiment, the signal intensity reflects the antibody concentration). In one embodiment, the method further comprises step d) diluting a portion of said second serum sample to create a diluted second serum sample; and e) contacting the undiluted second serum sample and diluted second serum sample with the cell line and the medium under conditions such that a reporter gene emits a detectable signal upon induction by a TSH receptor-specific stimulating auto-antibody. In one embodiment, the method further comprises step f) comparing the activity of the expressed reporter gene from the first and second serum samples. In one embodiment, the comparative reactivity profiles of the first and second serum samples serve as an indication of patient response to drug treatment. In one embodiment, said culture medium contains a glucocorticoid. In one embodiment, said reporter gene is luciferase. It is not intended that the present invention be limited by nature of the drug treatment. A variety of drugs and treatment approaches can be utilized. In one embodiment, the drug received by said patients is selected from the group consisting of anti-thyroid drugs, steroids, T4, and immunosuppressive drugs. In one embodiment, the thyrotropin stimulating hormone receptor auto-antibody concentration is used to monitor drug treatment (e.g. whether immunosuppressive drug therapy is effective).

DETAILED DESCRIPTION

The present invention provides methods and compositions useful in the diagnosis of autoimmune diseases. In particular, the present invention provides methods and compositions for use in the diagnosis and management of Graves' disease. For example, one composition comprises a chimeric thyroid stimulating hormone receptor having improved sensitivity and specificity for circulating thyroid stimulating immunoglobulin. Assays using such chimeric receptors can be optimized in the presence of a glucocorticoid.

In addition, the present invention provides methods and compositions for monitoring the immune status and responses of individuals. In particular, the present invention finds use in monitoring the immune responses of vaccine recipients. The present invention further provides methods and compositions for accelerating and enhancing the attachment of viruses to cell surface receptors, providing increased sensitivity in assays to detect and quantitate viruses in samples.

I. Graves' Disease

Typically, the clinical picture of Graves' disease in young adults is very easily recognized. The patients are more commonly female than male, and report symptoms including, but not limited to, sweating, palpitations, nervousness, irritability, insomnia, tremor, frequent stools, and weight loss in spite of a good appetite. Physical examination usually shows mild proptosis, stare, lid lag, a smooth, diffuse, non-tender goiter, tachycardia (especially after exercise) with loud heart sounds, and often a systolic murmur or left sternal border scratch, tremor, onycholysis, and palmar erythema; often, a bruit is heard over the thyroid, and a cervical hum is almost always present. In patients with these symptoms, Graves' disease is readily recognized, and can be confirmed with laboratory tests (See, Federman, Thyroid, in Dale and Federman (eds.), Scientific American Medicine, 3:1-6, Scientific American, New York, N.Y., (1997).

Although the signs and symptoms described above can be troublesome, other symptoms of the disease can be more dangerous. One of the most disturbing symptoms is severe exopthalmos, accompanied by opthalmoplegia, follicular conjunctivitis, chemosis, and loss of vision. Additional symptoms include, but are not limited to, dermopathy, pretibial myxedema, clubbing, and in the most severe cases, acropachy. These signs and symptoms are indicative of a representative autoimmune etiology of Graves' disease.

Despite the typical clinical picture of Graves' disease, methods are needed to confirm the diagnosis, as well as provide prognostic indicators for management and treatment. In addition, in cases where the cause of hyperthyroidism is unclear, diagnostic test methods must be utilized to determine the etiology. Although in vivo methods such as radioactive-iodine uptake (RAIU) may be used in the diagnosis and monitoring of patients with Graves' disease (See e.g., Baldet et al., Acta Endocrinol. (Copenh) 116:7-12 (1987)), there are two basic groups of in vitro assay systems developed for this purpose. One is dependent upon the measurement of some index of thyroid stimulation (e.g., cAMP generation) and the other assesses the ability of thyroid-stimulating autoantibodies (TSAb) to inhibit the binding of radiolabelled thyroid stimulating hormone (TSH) to its receptor. These methods include bioassays and in vitro assays for TSAb. However, no widespread application of methods to measure the thyroid-stimulating immunoglobulin (TSI or TSAb) in Graves' disease diagnosis has been reported. (See e.g., Rapoport et al., J. Clin. Endocrinol. Metabol., 58:332-338 (1984)). In addition, it was recognized that in the sera of Graves' disease patients there is a heterogenous population of immunoglobulin G (IgG) molecules that recognize the thyroid hormone receptor (See e.g., Yokoyama et al., J. Clin. Endocrinol. Metabol., 64:215-218 1987)). Further, the recognition that TSH-binding inhibition assays do not necessarily reflect a thyroid-stimulating activity contributed to confusion in attempts to reach agreement on the clinical application of such assays (See e.g., McKenzie and Zakarija, J. Clin. Endocrinol. Metabol., 69:1093-1096 (1989)). Limitations in terms of sensitivity and specificity were also problematic. Indeed, problems associated with available assay systems resulted in arguments that the measurement of thyroid peroxidase antibodies is a sufficiently sensitive marker for underlying thyroid autoimmunity (See, Botero and Brown, supra).

As indicated by Rapoport et al., the available assays that could be performed easily, in a standardized manner, and for large numbers of samples had significant limitations in terms of sensitivity and/or specificity, making these tests unreliable for clinical use. These problems apply primarily to assays that measure the ability of TSI to inhibit the binding of radiolabelled TSH to human thyroid plasma membranes (i.e., the assays do not measure TSI activity per se). Also, not all of the anti-TSH receptor antibodies are stimulatory. Rapoport et al. further indicate that assays using TSI stimulation of adenylate cyclase activity in human thyroid plasma membranes are seriously lacking in sensitivity. Some assays are unpractical for general clinical use, including those that rely upon the use of fresh human thyroid tissue, involve extremely difficult techniques with limited sample capacity, and are very laborious and/or uneconomical (See e.g., Rapoport et al, supra). The development of assays using cultured canine and porcine thyroid cells to measure the cAMP response to TSH were later adapted for use with human thyroid cells which offered potentially superior results. In addition to the requirement for fresh thyroid cells in some of these methods (e.g., the methods discussed by Rapoport et al.), many also required tedious and time-consuming sample preparation prior to assaying the specimens. For example, some protocols require laborious and time-consuming dialysis methods and/or precipitation of immunoglobulins in the test sera with ammonium sulfate or polyethylene glycol (See e.g., Rapoport et al., supra; and Kasagi et al., J. Clin. Endocrinol. Metabol., 62:855-862 (1986)).

In view of the problems encountered with these assay systems, other methods were investigated in an effort to develop an assay that is easy to perform, reliable, sensitive, and specific for Graves' disease autoantibodies. For example, the use of bioassays to measure cAMP production rely upon the use of cells of non-human origin grown in continuous culture or on human cells used as primary cultures or frozen in aliquots for use as needed. Problems with the use of human thyroid cells include the variability in responsiveness of surgically obtained thyroid tissue. Thus, cells of nonhuman origin gained popularity, including the rat thyroid cell line (FRTL-5). This is a non-transformed, differentiated cell line that has been well-studied and characterized (See e.g., Bidey et al., J. Endocrinol., 105:7-15 (1985); and Michelangeli et al., Clin. Endocrinol., 40:645-652 (1994)). However, a number of disadvantages make these cells less than ideal for Graves' disease assays. For example, the cells are slow growing and have fastidious growth requirements which include the need for TSH. Consequently, it is necessary to deprive the cells of TSH for at least 5 days prior to assay in order to achieve a reasonable level of sensitivity.

Subsequent development of cells such as the JP09 cells (Chinese hamster ovary cells transfected with a functional human TSH receptor) and other cell lines which stably express the human TSH receptor have greatly improved the assay systems available for the detection of Graves' disease autoantibodies. These cells have a TSH receptor that is comparable to that of native thyrocytes and possess a functional signal transduction system involving G-protein coupling, activation of adenylate cyclase and cAMP generation in response to TSH and to thyroid-stimulating antibodies (TSAb) (See e.g., Michelangeli et al., supra). These cells have been reported to be superior to FRTL-5 cells as they provide similar diagnostic information, but are more sensitive, grow faster, have less fastidious growth requirements, and respond to unextracted sera, in comparison with FRTL-5 cells (Michelangeli et al., supra; see also, Kakinuma et al., J. Clin. Endocrinol. Metabol., 82:212902134 (1997)). In addition, these methods are more rapid and reproducible, and perhaps more specific for detection of human autoantibodies directed against the human receptor. Further, the assays are easier and less cumbersome to perform than those using the FRTL-5 cell line (See e.g., Vitti et al., J. Clin. Endocrinol. Metabol., 76:499-503 (1993)). However, these assays rely upon the use of radioactivity (e.g., in radioimmunoassays) to detect and quantitate cAMP and are as a result, still cumbersome.

II. Diagnostic Assays for Graves Disease

Graves' disease is a thyroid disorder caused by an antibody-mediated auto-immune reaction. In Graves' patients, the autoantibodies recognizing the TSHR (TRAbs) are heterogeneous, including mainly thyroid stimulating antibodies (TSAbs) and thyroid blocking antibodies (TBAbs.) TSAbs act as a TSH agonist causing hyperthyroidism while the TBAbs function as a TSH antagonist causing hypothyroidism. While TSAb and TBAb bind to different epitopes on the TSHR, TBAb binding can "neutralize" the stimulating effect of TSAb. When the TSAb binds to the TSHR, it induces the cAMP signaling pathway, TBAb does not have this effect.

Currently, several bioassays are used to diagnose Graves' disease. The Kronus® Radio Receptor Assay (RRA) kit is used for determination of TRAbs and detects both TSAbs and TBAbs but cannot distinguish between the two. Diagnostic Hybrids Inc. (DHI) previously developed a Graves' diagnostic CHO-Luc cell line that detects the TRAbs in patient serum. This cell line co-expresses the wildtype TSH receptor gene and a firefly luciferase gene which is driven by the human glycoprotein alpha subunit promoter. This wild type TSHR has epitopes that bind TSAbs and TBAbs. Binding of TBAb to the receptor can modulate TSAbs' binding, resulting in lower stimulation by the TSAbs.

Thyroid-stimulating autoantibodies (TSAb) directed against the thyroid stimulating hormone (TSH) receptor are capable of stimulating thyroid adenylyl cyclase, the enzyme responsible for producing cyclic-adenosine monophosphate (cAMP). These autoantibodies have been used as diagnostic markers for detection and identification of patients suffering from Graves' disease, as these autoantibodies appear to be responsible for the hyperthyroidism seen in patients with this disease. However, as discussed in more detail below, the methods commonly used to detect and measure these TSAbs are complex and time-consuming.

A. cAMP Detection

One method that measures TSAbs utilizes a rat thyroid cell line known as "FRTL-5." This cell line, available from Interthyroid Research Foundation (Baltimore, Md.) expresses receptors that cross-react with human TSAbs. In the presence of TSAbs (i.e., for example, upon exposure of the cells to serum from a Graves' patient containing these antibodies), FRTL-5 cells are stimulated to produce cAMP. This cAMP is then measured in a portion of the lysed cells or the medium bathing the cells using a radioimmunoassay method. The FRTL-5 cells formed the basis for the first successful bioassay for the autoantibodies that are pathognomonic of Graves' disease. U.S. Pat. No. 4,609,622 (herein incorporated by reference).

B. FRTL-5 Cell Assays and Starvation Medium

A typical assay using FRTL-5 cells performed as described by Vitti et al. (Vitti et al., J. Clin. Endocrinol. Metabol., 76:499 (1993)) involves seeding FRTL-5 cells in 96-well plates (30,000 cells/well) in a special complete medium containing 6 hormones (i.e., for example, a 6H medium) in addition to the normal growth constituents used in cell culture medium. After 2-3 days incubation in a 5% $CO_2$, humidified, 37° C. incubator (i.e., when the cells are confluent), the medium is changed to a "Starvation Medium," which is deficient in TSH (thereby resulting in a 5H medium), wherein TSH is one of the 6 hormones in the 6H medium. The cells are then maintained for 4-5 days in the incubator with a medium change every 2-3 days. During this time the cells do not grow or multiply. Subsequently, the cells may be used in a diagnostic assay.

C. Radiolabel Assays and Stimulation Medium

Early diagnostic methods for Graves' disease were performed by removing the Starvation Medium and adding a Simulation Medium comprising a special low sodium chloride, high sucrose buffer (HBSS NaCl+222 mM sucrose; the formula for this buffer is: 0.0608 g/L $KH_2PO_4$, 0.144 g/L $CaCl_2$, 0.373 g/L KCl, 0.048 g/L $MgSO_4$, 0.097 g/L $Na_2PHO_4$, 1.0 g/L D-glucose, 76 g/L (i.e., 222 mM) sucrose, 4.77 g/L HEPES, and 10 g/L BSA; pH 7.2-7.4) containing a phosphodiesterase inhibitor (e.g., 0.5 mM methylisobutylxanthine; IBMX), to prevent this enzyme from breaking down cAMP. Specially prepared samples of patient immunoglobulin (IgG), controls, and standards are added to the appropriate wells, usually in triplicate, and the plate is incubated in a 5% $CO_2$, humidified, 37° C. incubator for 2 hours. Following this incubation, 5-10 µl of the medium are removed from each well and used in a radioimmunoassay system to detect the presence of cAMP. Typically this assay is run with about 6 standards in duplicate, with patient and controls also run in duplicate. The assay usually requires an overnight incubation with about an hour required the next day for the separation of free, radiolabelled cAMP from antibody-bound, radiolabelled cAMP.

As the use of radioactivity and long preparation times are negative aspects of the FRTL-5 assay, improved systems have been developed. One investigation involved the use of low salt conditions to increase the sensitivity of the assay system (See, Kosugi et al., Endocrinol., 125:410-417 (1989)). Additional improvements in the bioassay involved a strain of Chinese Hamster Ovary ("CHO") cells transfected with a human TSH receptor ("CHO-R"; See, Vitti et al., supra). This cell line offered two major improvements over the FRTL assay. First, this method involves the use of human TSH receptors instead of rat TSH receptors which should provide greater specificity and perhaps sensitivity for the detection of TSAbs. Second, there is no requirement for the special 6H medium and 5H medium changes over a 6-8 day period, since the CHO-R cells grow well on a standard supplemented medium and can be used 1-3 days after seeding, depending on the density of the cell suspension used to inoculate the wells. In addition, comparative studies with FRTL-5 cells have shown that the CHO-R cells may be more accurate in detecting Graves' TSAbs (See, Vitti et al.).

D. Luciferase Gene Assays Using CHO-Rluc Cell Lines

A further improvement was provided by the use of CHO-R cells designed to readily assess the increased amounts of cAMP caused by TSI through the use of a reporter gene (i.e., for example, luciferase) (Evans et al., J. Clin. Endocrinol. Metabol., 84:374 (1999)). Thus, with the introduction of this engineered cell line (i.e., CHO-Rluc), the complexity and dangers inherent in the use of radioactive compounds used in the previously developed radioimmunoassay for cAMP detection and quantitation are eliminated. With these cells, luciferase is measured simply by removing the medium from the cells, adding a lysis buffer, allowing 20-30 minutes for lysis to occur, removing a sample of the lysate, adding luciferase substrate and measuring light output over a 15 second interval using a luminometer. However, as indicated in the Experimental section below, this method provides equivocal results and required further improvement.

In one embodiment, the present invention contemplates methods that incorporate the advantages of a CHO-Rluc protocol, while providing additional advantages in terms of reliability and reproducibility. Considerable development effort was dedicated to the development of methods of the present invention, including those that allow the use of CHO-Rluc cells in luminometric assays using TSH and immunoglobulins from untreated Graves' disease patients.

The standard protocol originally used involved planting the CHO-Rluc cells from a frozen stock, so as to seed at a concentration that produced confluent monolayers after 18-24 hours of incubation. Initially, the Growth Medium was removed and Stimulation Medium was added to the monolayers, to which a series of TSH standards (e.g., 0, 10, 100, 1000 µIU TSH/ml), and patient IgG samples were added. As this approach yielded poor results, an overnight Starvation or conditioning period was tested.

A Starvation period resulted in improved results with lower background values and appeared to produce good values for the TSH standards and the test patient samples. An additional experimental option was also tested in which polyethylene glycol (PEG) was used to enhance antigen and antibody binding. In these experiments, PEG was added to the Stimulation Medium.

In various experiments, different media formulations and combinations were tested, as described in the Experimental section below. For example, starvation with the Stimulation Medium resulted in RLU/sec values of (32,103) for the 0 µIU/ml TSH standard, −1,148 for the 10 µIU TSH/ml sample, 47,478 for the 1000 µIU TSH/ml sample, and 19,350 for IgG sample #13. In this, and the following discussions, the numbers in parentheses represent the 0 µIU TSH/ml value, which is subtracted from the values for the standards or samples to yield net values.

Starvation with standard HBSS resulted in RLU/sec values of (21,671) for the 0 µIU/ml TSH control, 1,336 for the 10 µIU TSH/ml sample, 82,466 for the 1000 µIU TSH/ml sample, and 39,082 for IgG sample #13. Starvation with standard HBSS and 6% PEG in the Stimulation Medium resulted in RLU/sec values of (32,562) for the 0 µIU/ml TSH control, 5,980 for the 10 µIU TSH/ml sample, 207,831 for the 1000 µIU 5 TSH/ml sample, and 174,461 for IgG sample #13. Thus, starvation with standard HBSS yielded higher values for TSH and the Graves' disease samples, and the incorporation of PEG into the Stimulation Medium yielded even higher values. These higher values appear to impart a higher level of sensitivity in the methods of the present invention, as compared to the above described methods. Nonetheless, the long duration of these assays involving Starvation periods is disadvantageous. It was hypothesized that assay improvements that shortened the 3-4 days assay period might also improve assay sensitivity and accuracy.

E. Chimeric TSH Receptor Cell Lines

In one embodiment, the present invention contemplate recombinant cell lines (i.e., for example, CHO and RD) that express a TSH/LH/TSH chimeric receptor (i.e., for example, RMc4) in combination with a firefly luciferase gene. In one embodiment, the expression is driven by a human glycoprotein alpha subunit promoter. Although it is not necessary to understand the mechanism of an invention, it is believed that by using a chimeric receptor, binding of the blocking antibodies (i.e., for example, TBAb) is either eliminated and/or reduced. In one embodiment, a chimeric receptor comprises at least one genetic modification such that only a TSAb binding region is expressed. It is believed that the recombinant cell lines have increased specificity when compared to either the CHO-Luc cells or KRONUS® assay.

III. Monitoring of Immune Response Development

As indicated above, the present invention also provides methods and compositions for the monitoring of immune response development. In particular, the present invention provides methods and compositions suitable for monitoring the response of individuals to vaccination.

In one embodiment, a pre-immune serum (i.e., serum collected prior to administration of vaccine) may be used as a baseline for control purposes. Such serum would also be collected shortly following vaccination (e.g., 1-2 weeks after vaccination), as well as periodically in the months following vaccination. The serum samples are then tested for the presence and quantity of neutralizing antibodies.

In some embodiments, diagnostic assays are conducted to monitor the response to viral antigens. In such assays, cells such as ELVIS™ (Diagnostic Hybrids, Athens, Ohio) are used in combination with a polyethylene glycol (PEG) solution of the present invention. In one embodiment, PEG enhances the antigen-antibody reaction, thereby resulting in higher reactivity.

IV. TSI Detection in CHO-Mc4luc and RD-Mc4luc Cell Lines

In one embodiment, the present invention contemplates using genetically engineered Chinese Hamster Ovary (CHO) and/or human Rhabdomyosarcoma cells (RD) for diagnosing Graves' disease and/or monitoring Graves' disease therapy.

Clinical laboratories currently utilize various cells and reaction buffer for the detection and measurement of stimulating autoantibodies specific to Graves' disease in patient sera for identifying patients suffering from this disease and monitoring their therapy. For example, cells comprising genetically modified CHO cells containing wild type human Thyroid Stimulating Hormone Receptor (TSHR) and the CRE-Luc reporter system are utilized by numerous laboratories. These cells, however, need one day for growth and one day for starvation which puts a time constraint on test results availability. On the third day, the patient's serum specimens are incubated with the cells and reaction buffer in order to detect the presence of the Graves' autoantibodies. In some embodiments, the present invention contemplates methods that do not require these multi-day assay procedures. In one embodiment, these shorter methods do not have a Starvation period incubation. The advantages of a quick, accurate, and sensitive assay to diagnose Grave's disease are explained more fully below.

In one embodiment, the present invention contemplates a method for improving a thyroid stimulating immunoglobulin (TSI) detecting cell line (CHO-RLuc). In one embodiment, the cell line further comprises a chimeric receptor. In one embodiment, the chimeric receptor comprises a human Thyroid Stimulating Hormone Receptor (TSHR) and a rat Luteinizing Hormone (LH) (i.e., for example, a RMc4 receptor). Although it is not necessary to understand the mechanism of an invention, it is believed that a chimeric TSH receptor provides improved binding specificity for TSI such that a Starvation period in the diagnostic assay is not required.

In one embodiment, the present invention contemplates a method for expressing the Mc4 chimeric receptor in the CHO cells and/or RD cells (or other mammalian cells). In one embodiment, the method further comprises using CRE-Luc as a reporter gene to detect TSI. In one embodiment, the chimeric receptor provides greater specificity than a wild-type receptor by preferentially binding to stimulating autoantibodies (i.e., as opposed to blocking autoantibodies). In one embodiment, the chimeric receptor provides greater sensitivity than a wild-type receptor by preferentially binding to stimulating autoantibodies (i.e., as opposed to blocking autoantibodies). In one embodiment, the cell culture further comprises PEG. Although it is not necessary to understand the mechanism of an invention, it is believed that because Graves' patient sera can have both stimulating and blocking autoantibodies, the wild type TSH-R receptor will bind with both antibodies equally. Further, it is believed that blocking autoantibodies can moderate and suppress stimulating autoantibody activity.

These chimeric TSH-R receptors expressed in the disclosed cell lines offer the following advantages over currently used cell lines:

1. The system results in a lower luciferase activity background leading to higher Signal:Noise (S:N) or Signal:Background (S:B) ratios.

2. The cell lines do not need to be "starved" overnight, a requirement for currently used cell lines in order to maximize the signal resulting from TSI binding. This change reduces the turn-around time from a current 3 day assay to a 2 day assay, which is very advantageous to the laboratory, the physician, and the patient.

3. The assay is designed to measure stimulating antibodies, whereas the wild type TSH-R is responsive to both stimulating and blocking antibodies whereas this Mc4 chimeric receptor is responsive only to stimulating antibodies, thereby providing greater specificity for what is being measured.

V. Chimeric TSH Receptor

In one embodiment, the present invention contemplates novel diagnostic cell lines that detect thyroid stimulating hormone receptor (TSH-R) autoantibody (i.e., for example, thyroid stimulating immunoglobulin; TSI) with high detection sensitivity and specificity. In one embodiment, the cell line comprises a recombinant Chinese Hamster Ovary cell (i.e., for example, a CHO-K1 cell). In one embodiment, the cell line comprises a Human Rhabdomyosarcoma (RD) cell.

In one embodiment, the present invention contemplates a vector comprising a nucleic acid sequence encoding a hTSH/rLH-R fusion protein (i.e., for example, RMc4) linked to a firefly luciferase reporter gene and in operable combination with a glycoprotein hormone alpha subunit promoter. In one embodiment, a cell line is transfected with the vector. In one embodiment, the transfected cell line expresses a human TSH-R/rat Luteinizing hormone (LH) chimeric receptor (hTSH/rLH-R), under conditions such that the luciferase reporter signal is detected.

A. Chimera Construction

The identity of binding sites for TSH and thyroid stimulating autoantibodies in relation to Graves' disease was initially examined by constructing human/rat chimeric TSH-R constructs. A partial substitution of the human TSH-R with the corresponding rat sequence resulted in the following chimeric receptors: i) Mc1+2 substituting amino acid residues 8-165; ii) Mc2 substituting amino acid residues 90-165; and iii) Mc4 substituting amino acid residues 261-370. The data suggested that amino acid residues 8-165 contain an epitope specific for thyroid stimulating autoantibodies which are not the same as those required by TSH. Significant heterogeneity in the binding sites between idiopathic myxedema thyroid stimulating antibodies, Graves' disease thyroid stimulating antibodies, and TSH was observed. Tahara et al., "Immunoglobulins From Graves' Disease Patients Interact With Different Sites On TSH Receptor/LH/CG Receptor Chimeras Than Either TSH Or Immunoglobulins From Idiopathic Myxedema Patients" *Biochem Biophys Res Comm* 179:70-77 (1991).

Early studies demonstrated transfection and expression of chimeric TSH receptors that included segments from rat TSH receptors and rat lutenizing hormone chorionic gonadotropin receptors. Various rat TSH amino acid sequences were substituted with the corresponding rat LH/GC sequences. The data demonstrated that amino acid residues 268-304 were not critical for generating the cAMP response but did eliminate a TSH high affinity binding site. Akamizu et al., "Chimeric Studies Of The Extracellular Domain Of The Rat Thyrotropin (TSH) Receptor: Amino Acids (268-304) In The TSH Receptor Are Involved In Ligand High Affinity Binding, But Not In TSH Receptor-Specific Signal Transduction" *Endocr J* 40:363-372 (1993). The heterogeniety of anti-TSH receptor antibodies was addressed by comparing binding of: i) TSH-binding inhibitory immunoglobulin; ii) thyroid-stimulating antibody; and iii) thyroid blocking antibody using a chimeric human TSH receptor wherein amino acid residues 90-165 of the human TSH receptor were substituted by equivalent amino acid residues from the lutenizing hormone chorionic gonadotropin receptor. The binding data suggest that there might be two different types of thyroid-stimulating antibodies, three different types of TSH-binding inhibitory immunoglobulins, and one nonfunctional antibody.

Chimeric TSH receptors have been reported to detect and characterize various types of circulating antibodies suspected of having a relationship with Graves' disease. Such antibodies are believed to include, but are not limited to, stimulating autoantibodies that can activate TSH-R and blocking autoantibodies that can block TSH-R binding by either TSH or stimulating autoantibodies. For example, chimeras of human TSH-R (hTSH-R) and lutenizing hormone human chorionic gonadotropin receptor (LH-hCG-R) included an RMc4 chimera having amino acids 261-370 of the hTSH-R substituted with equivalent residues from a human LH/CG-R. The ability of purified IgG samples from Graves' disease sera samples to stimulate cAMP production was measured by radioimmunoassay. Kung et al., Epitope Mapping of TSH Receptor-Blocking Antibodies In Graves' Disease That Appear During Pregnancy" *J Clin Endocrinol Metab* 86:3647-3653 (2001).

The interactions between TSH stimulating and blocking autoantibodies was addressed by using two types of TSH-R chimera constructs. The first chimera is designated Mc2 having human TSH-R amino acid residues 90-165 substituted by equivalent residues from rat lutenizing hormone chorionic gonadotropin receptor. The second chimera is designated Mc1+2 having human TSH-R amino acid residues 8-165 substituted by equivalent residues from rat lutenizing hormone chorionic gonadotropin receptor. Evaluation of circulating autoantibodies in Graves' disease patients showed that blocking autoantibodies do not strongly antagonize the action of stimulating autoantibodies, but could be responsible for underestimating stimulating autoantibody activities as measured by current CHO-hTSH-R diagnostic assay methods. Kim et al., "The Prevalance And Clinical Significance Of Blocking Thyrotropin Receptor Antibodies In Untreated Hyperthyroid Graves' Disease" *Thyroid* 10:579-586 (2000).

The DNA sequence of the chimeric hTSH/rLH-R receptor (RMc4) contains a total of 2,324 base pairs and encodes 730 amino acids. FIG. 8. In this chimeric receptor, the human TSH-R region ranging from amino acid number 262 to 335 was substituted with the corresponding 73 amino acids from the rat luteinizing hormone (LH) receptor The sequence that drives the expression of the luciferase reporter is a 236 nucleotide glycoprotein alpha subunit promoter, which contains a cyclic AMP (cAMP) regulatory element (CRE) and was cloned by PCR. The nucleotide sequence of the cloned promoter was determined by DNA sequencing and was confirmed by sequence comparison with Gene bank sequence AF401991. An alignment of the cloned promoter with a GPH promoter amplified by PCR from HEK cells indicate that the two sequences are identical. FIG. 9.

C. Chimera Diagnostic Assay

Figure 10:
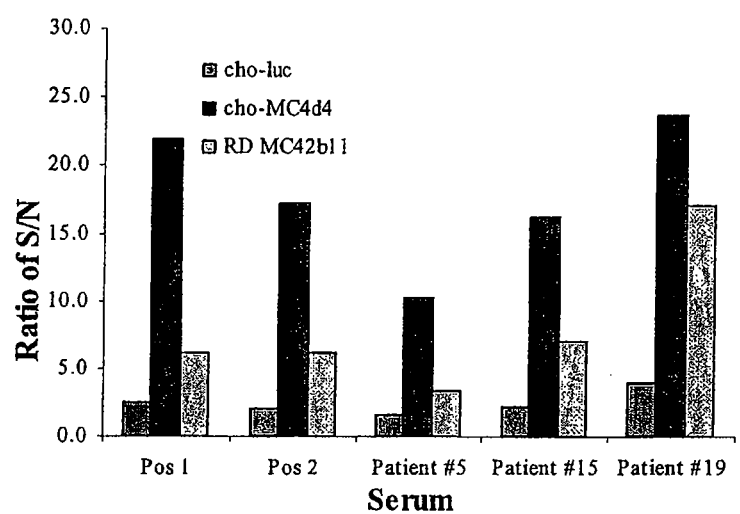
FIG. 10 presents exemplary data showing the response of the CHO-RMc4, RD-RMc4 and CHO-RLuc cell lines to negative and positive TSI-containing sera.

The response of the CHO-RMc4luc, RD-RMc4luc and CHO-Rluc cell lines to negative and positive TSI sera was then compared. The cells were incubated with TSI negative and positive sera for three hours. Cells were then lysed and luciferase activity was measured by a Veritas Microplat Luminometer. The results indicated that both the CHO-RMc4luc and RD-RMc4luc cell lines had much higher detecting sensitivity when compared to the CHO-Rluc cells. FIGS. 10A, 10B, 10C, 10D and 10E. A comparison of the ratio of luciferase RLU from TSI positive sera to the negative sera (ratio of S/N,) shows that CHO-RMc4luc and RD-RMc4luc cells were 6-8 and 2.1-4 times more sensitive than CHO-Rluc cell line. FIGS. 10B and 10D, respectively. CHO-RMc4luc cells were about 1.3 to 3.5 more sensitive than RD-RMc4luc cells. FIG. 10E. In addition, the CHO-RMc4luc had lower levels of induced luciferase activity than CHO-Rluc when tested with TSI negative serum leading to lower background and increased signal/negative (S/N) ratios. FIG. 10A. Furthermore, both CHO-RMc4luc and RD-RMc4luc cell lines showed very low standard deviation values. FIG. 10A and FIG. 10C, respectively. A TSI positive serum, denoted #19, showed a high luciferase induction level on the CHO-RMc4luc, RD-RMc4luc and CHO-Rluc cell lines This serum was diluted and tested on these cell lines to compare the sensitivities. FIG. 10E.

Further, detecting sensitivity between the CHO-Rluc, CHO-RMc4luc and RD-RMc4luc cell lines induced with a serially diluted TSI positive serum was compared. For example, a TSI positive serum was serially diluted and incubated on the different cell lines for three hours. The RD-RMc4luc and CHO-Rluc cell lines showed linear responses of the ratio of S/N in the serum dilution range between 1:2 and 1:8. However, the slope of the dose response (value) and hence, the detection sensitivity, for RD-RMc4luc was much higher than that of CHO-Rluc cell line. FIG. 11A. CHO-RMc4luc did not show a linear response of the ratio of S/N at no or low serum dilutions. FIG. 11B. CHO-RMc4luc cells, however, did show a linear dose response of the ratio of S/N from the serum dilution ranging from 1:32 to 1:128. FIG. 11C. Note that the slope of the dose response (value) was even higher than that of RD-RMc4luc cell line. FIG. 11A versus FIG. 11C.

Figure 12:
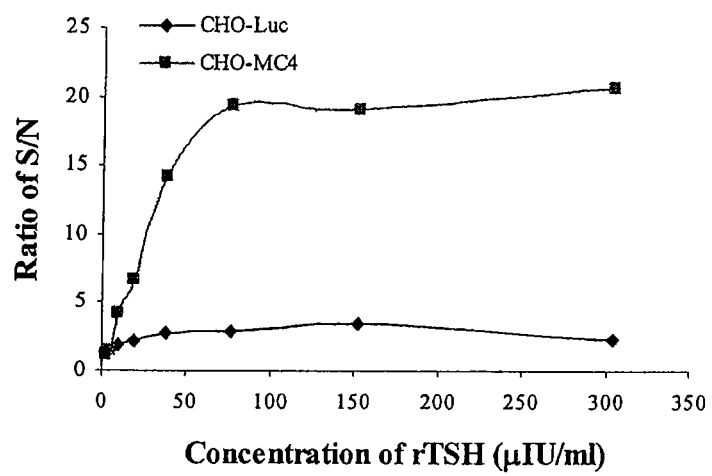
FIG. 12 presents exemplary data comparing TSH sensitivity between a CHO-RMc4 cell line and a CHO-RLuc cell line.

The CHO-RMc4luc cell line was also compared to the CHO-Rluc cell line for TSH sensitivity. The S/N ratio was derived from the luciferase assay using CHO-Rluc, CHO-RMc4luc and RD-RMc4luc cell lines induced with recombinant human TSH. Recombinant human TSH at various concentrations was incubated with CHO-RMc4luc or CHO-Rluc cell lines for three hours. After incubation, the luciferase assays were performed. The results indicated that they both are able to detect TSH at a concentration as low as 5 µIU/ml, but the detection sensitivity of CHO-RMc4luc was much higher than that of the CHO-Rluc cell line. FIG. 12.

CHO-RMc4luc and CHO-Rluc cell lines were also tested for their specificity using other anterior pituitary hormones including human luteinizing hormone, LH,) human follicle stimulating hormone (hFSH) and human chorionic gonadotropin (hCG), all of which share a common alpha subunit. Neither cell line showed any cross activity with the tested hormones. Table 1.

TABLE 1

Specificity of CHO-Rluc and CHO-RMc4luc to human TSH and other hormones.

A. Luciferase S/N Ratio Comparision Of TSI Serum To Gonadotropin Hormones

| | Ratio of Signal/Negative | | | | |
|---|---|---|---|---|---|
| | Positive TSI serum | FSH (364 mIU/ml) | LH (455 mIU/ml) | HCG (29.5 IU/ml) | hTSH (76 µIU/ml) |
| CHO-Mc4luc | 9.4 | 0.6 | 0.9 | 0.8 | 19.4 |
| CHO-Rluc | 1.9 | 0.7 | 0.8 | 0.96 | 2.9 |

| | −TSI serum | +TSI serum | Hormones |
|---|---|---|---|

B. CHO-RMc4luc Cell Line Results

CHO-RMc4luc

| | | −TSI serum | +TSI serum | Hormones |
|---|---|---|---|---|
| FSH (364 mIU/ml) | RLU | 1589 | 15069 | 1019 |
| | Ratio of S/N | | 9.5 | 0.6 |
| LH (455 mIU/ml) | RLU | 1737 | 15565 | 1561 |
| | Ratio of S/N | | 9 | 0.9 |
| hCG (29.5 IU/ml) | RLU | 1432 | 13491 | 1168 |
| | Ratio of S/N | | 9.4 | 0.8 |
| hTSH (76 µIU/ml) | RLU | 1284 | 12512 | 24880 |
| | Ratio of S/N | | 9.7 | 19.4 |

C. CHO-Rluc Cell Line Results.

CHO-Rluc

| | | −TSI serum | +TSI serum | Hormones |
|---|---|---|---|---|
| FSH (364 mIU/ml) | RLU | 1052 | 1929 | 728 |
| | Ration of S/N | | 1.8 | 0.7 |
| LH (455 mIU/ml) | RLU | 1058 | 2011 | 835 |
| | Ration of S/N | | 1.9 | 0.8 |
| hCG (29.5 IU/ml) | RLU | 946 | 1976 | 912 |
| | Ration of S/N | | 2.1 | 0.96 |
| hTSH (76 µIU/ml) | RLU | 847 | 2291 | 2495 |
| | Ration of S/N | | 2.7 | 2.9 |

Figure 13:
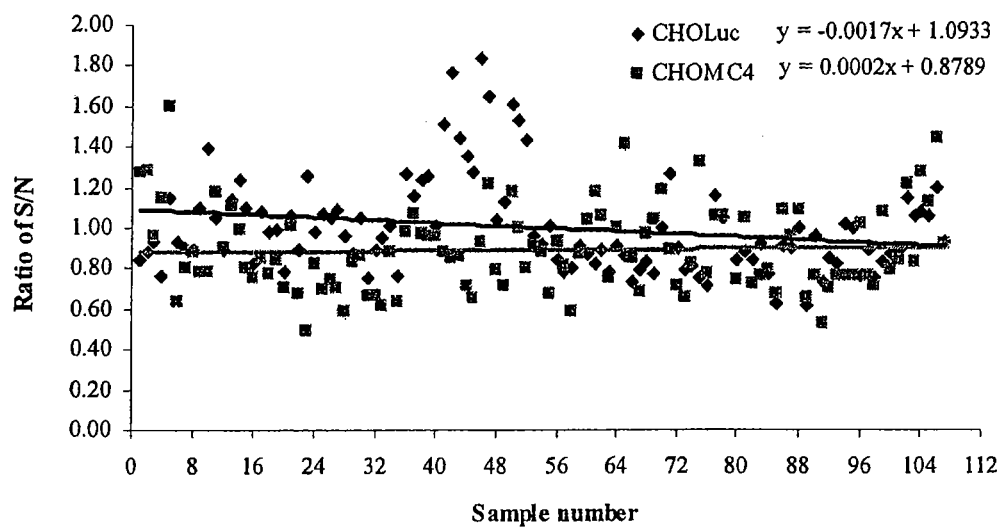
FIG. 13 presents exemplary data presenting the distribution of signal-to-noise ratios from human sera using CHO-RMc4 and CHO-RLuc cell lines.

CHO-RMc4luc and CHO-Rluc cell lines were used to screen normal human sera to determine the distribution of the ratio of S/N derived from a luciferase assay. Comparisons of distribution of the S/N ratios derived from luciferase assays on CHO-Rluc and CHO-RMc4luc cell lines induced with sera from 108 normal people were performed. All serum samples were tested in both CHO-RMc4luc and CHO-Rluc cell lines. A known normal serum was used as a reference for calculating S/N ratios. The distribution of CHO-RMc4luc cell line revealed a pattern very similar to that of the CHO-Rluc cell line. The mean of the CHO-Rluc cell was 1 and the CHO-RMc4luc was 0.88. The standard deviation of CHO-Rluc was 0.23 and CHO-Luc was 0.21. FIG. 13.

Figure 14:
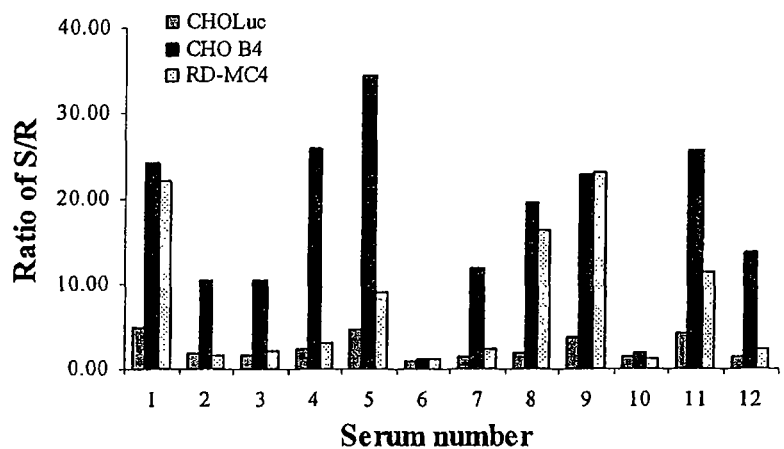
FIG. 14 presents exemplary data showing the relative sensitivity of the CHO-RMc4, RD-RMc4 and CHO-RLuc cell lines to clinical patient serum samples.

The responses of the CHO-RMc4luc, RD-RMc4luc and CHO-Rluc cell lines to clinical patient serum samples were compared. The ratio of S/N derived from the luciferase assay on CHO-Rluc, CHO-RMc4luc and RD-RMc4 luc cell lines induced with 12 clinical serum samples. Each of the 12 serum samples was tested in the CHO-RMc4luc, RD-RMc4luc and CHO-Rluc cell lines. Luciferase activities of these samples were compared to that from a known negative serum sample (negative reference). The results of this study indicated that both the CHO-RMc4luc and RD-RMc4luc cell lines had much higher detection sensitivity when compared to the CHO-Rluc cell line with the and CHO-RMc4luc cell line being the most sensitive cell line. FIG. 14.

VI. Chimeric Receptor Assay and the Starvation Pre-Conditioning Period

As discussed above, the CHO-RMc4luc cell line provides definite advantages in sensitivity and specificity over the currently used CHO-Rluc cell lines. For example, the CHO-RMc4luc cells, upon stimulation by Graves' Disease antibodies, provide increased luciferase responses as measured by the Relative Light Units (RLU) output. This improvement allows the elimination of the one day starvation step from the protocol.

The standard procedure used for the CHO-Rluc cell line includes a starvation period. The protocol for the Starvation format is to plant the cells for Growth on day 1, Starve on day 2 and Stimulate and measure RLU on day 3. When the starvation period is eliminated, the "starve day 2" step is eliminated and the final results can be reported to the physician on day 2 instead of day 3, which is much more desirable. This non-starved protocol provides a significant advantage to the user and physician because labor for the user is significantly reduced and the physician can have the results the next day, all with an assay of higher accuracy than that provided by the CHO-Rluc protocol with its one day of starvation.

Starvation periods were used to increase the RLU or % separation between Normal and Graves' Positive sera. This RLU separation relates directly to the accuracy of the assay. The effect of the Starvation period was tested using Graves' Positive and Normal serum specimens using the two different cell lines, CHO-Rluc and CHO-RMc4luc. See, Table 8.

TABLE 8

Relative Effects Of Starvation Periods On CHO-Rluc And CHO-RMc4luc Cells

| | Cutoff 130% CHO-RLuc Starved | | Cutoff 140% CHO-RMc4 Non-Starved | | Cutoff 170% CHO-RMc4 Starved | | |
|---|---|---|---|---|---|---|---|
| Serum # | (SRR) % | RLU | (SRR) % | RLU | (SRR) % | RLU | |
| 26 | 118% | 874 | 310.2% | 13457 | 1023.3% | 10162 | Positive |
| 27 | 149% | 1105 | 208.3% | 8751 | 198.0% | 1966 | |
| 28 | 302% | 2236 | 525.6% | 22083 | 1291.5% | 12825 | |
| 29 | 504% | 3725 | 627.3% | 27211 | 1912.2% | 18988 | |
| 30 | 380% | 2811 | 481.4% | 20885 | 1366.7% | 7763 | |
| 31 | 300% | 2221 | 660.3% | 27743 | 2345.7% | 13323 | |
| 32 | 571% | 4226 | 525.9% | 22096 | 1855.6% | 10540 | |
| 33 | 144% | 1062 | 405.8% | 17049 | 1495.9% | 8497 | |
| 34 | 208% | 1537 | 150.5% | 6530 | 265.8% | 1510 | |
| 35 | 167% | 1234 | 353.7% | 15345 | 917.3% | 5210 | |
| 36 | 180% | 1334 | 574.2% | 24909 | 2340.0% | 13291 | |
| 37 | 119% | 878 | 187.5% | 7878 | 388.9% | 2209 | |
| 38 | 114% | 846 | 231.9% | 9745 | 468.6% | 2662 | |

TABLE 8-continued

Relative Effects Of Starvation Periods On CHO-Rluc And CHO-RMc4luc Cells

| Serum # | Cutoff 130% CHO-RLuc Starved (SRR) % | RLU | Cutoff 140% CHO-RMc4 Non-Starved (SRR) % | RLU | Cutoff 170% CHO-RMc4 Starved (SRR) % | RLU | |
|---|---|---|---|---|---|---|---|
| 39 | 104% | 771 | 145.8% | 6127 | 287.8% | 3031 | |
| 40 | 137% | 856 | 81.0% | 3405 | 96.0% | 1011 | |
| Ave. |  | 1714 |  | 15548 |  | 7532 | |
| 7 | 94% | 504 | 39.2% | 1944 | 80% | 525 | Normal |
| 8 | 90% | 486 | 48.1% | 2382 | 88% | 658 | |
| 9 | 89% | 482 | 38.1% | 1887 | 78% | 724 | |
| 10 | 110% | 591 | 37.8% | 1872 | 79% | 639 | |
| 12 | 105% | 566 | 51.1% | 2290 | 90% | 963 | |
| 14 | 113% | 611 | 43.1% | 1930 | 99% | 907 | |
| 16 | 110% | 591 | 35.9% | 1608 | 75% | 659 | |
| 17 | 82% | 443 | 36.8% | 1648 | 85% | 617 | |
| 18 | 108% | 582 | 40.5% | 1816 | 77% | 696 | |
| 19 | 98% | 542 | 42.6% | 1908 | 84% | 666 | |
| 21 | 78% | 431 | 84.4% | 3781 | 101% | 613 | |
| 23 | 90% | 495 | 55.9% | 2504 | 49% | 587 | |
| 24 | 125% | 693 | 35.9% | 1609 | 82% | 428 | |
| 25 | 98% | 541 | 50.8% | 2274 | 70% | 711 | |
| 26 | 107% | 591 | 45.7% | 2049 | 75% | 603 | |
| 27 | 104% | 577 | 62.8% | 2813 | 71% | 647 | |
| 28 | 109% | 600 | 38.1% | 1707 | 59% | 613 | |
| 29 | 96% | 532 | 48.2% | 2021 | 83% | 509 | |
| 30 | 87% | 481 | 39.5% | 1655 | 87% | 721 | |
| 31 | 105% | 489 | 40.4% | 1696 | 66% | 769 | |
| 32 | 75% | 350 | 51.8% | 2173 | 67% | 589 | |
| 33 | 89% | 416 | 78.4% | 3289 | 62% | 592 | |
| Ave. |  | 527 |  | 2130 |  | 656 | |
| +RLU/−RLU |  | 3.25X |  | 7.3X |  | 11.9X | |

The RLU values for Graves' Positive and Negative sera as obtained using the respective protocols for starved CHO-Rluc and CHO-RMc4luc cells, and non-starved CHO-RMc4luc cells. The intended effect of starvation on CHO-RMc4luc cells was to decrease the background level of luciferase activity in the cells, thereby raising the ratio of RLU between Graves' Positive and Graves' Negative sera. For these sets of sera, the average ratio for Starved CHO-Rluc is 3.25x, for non-Starved CHO-RMc4luc is 7.29x and for Starved CHO-RMc4luc cells is 11.5x.

Thus, the non-starved CHO-RMc4luc cells provide a greater than 2-fold increase in luminosity (i.e., and therefore sensitivity) over the starved CHO-Rluc cells. This provides distinct advantages of a protocol lasting one day shorter and providing more accurate and sensitive results. The Serum: Reference Ratios (SRRs) compare the RLU values as percentages and further confirm that the CHO-RMc4luc cells (whether starved or non-starved) provide an improved separation between the RLUs between Normal and Graves' Disease sera. The Cutoff values presented are approximate and are indicative of Graves' Disease when the assayed value is ≥ to the cutoff value of the particular protocol/cell line.

VII. Chimeric Receptor Assay Improvements with Glucocorticoids

Because the above data indicate that Starvation periods also provide an improvement of the accuracy and sensitivity of the CHO-RMc4luc cells, further investigations were then directed to develop superior CHO-RMc4luc cell assays without a Starvation period.

One set of data was collected in accordance with Example 15, wherein CHO-RMc4luc cells underwent Starvation periods and then were incubated with various concentrations of dexamethasone (DEX). The data clearly indicate that dexamethasone significantly improved the RLU intensity over and above that provided by a Starvation period alone. Table 9.

TABLE 9

Effect of Dexamethasone On Starved CHO-R-Mc4 Cells CHO-RMc4luc

| DEX uM | Reference Serum | | | | | | |
|---|---|---|---|---|---|---|---|
|  | 0 | 12. | 25 | 40 | 50 | 100 | pc* |
| Test 1 | 151 | 141 | 132 | 126 | 122 | 973 | 1601 |
| Test 2 | 148 | 118 | 121 | 128 | 117 | 118 | 1277 |
| Test 3 | 122 | 129 | 129 | 123 | 135 | 120 | 1306 |
| Avg | 140 | 129 | 127 | 126 | 125 | 112 | 1395 |
| S/B |  |  |  |  |  |  | 9.9 |

| DEX uM | Patient #18 Serum | | | | | |
|---|---|---|---|---|---|---|
|  | 0 | 12.5 | 25 | 40 | 50 | 100 |
| Test 1 | 2795 | 4710 | 5172 | 5039 | 4861 | 3542 |
| Test 2 | 3393 | 5456 | 5151 | 5198 | 5298 | 3414 |
| Test 3 | 3167 | 5330 | 5260 | 5038 | 4909 | 3521 |
| Average | 3118 | 5165 | 5194 | 5092 | 5023 | 3492 |
| S/B | 22.2 | 39.8 | 40.6 | 40.4 | 40.1 | 31.1 |
| % of S/B | 100 | 180 | 183 | 182 | 181 | 140 |

*Positive Control

The data show that dexamethasone reduces the Reference serum RLU readings while at the same time greatly increasing Patient #18 RLU readings. Overall, the presence of dexamethasone results in about an 80% increase in S/B ratios for the Patient #18 serum samples.

These observations provided a suggestion that an improved assay may result if dexamethasone is used in place of a Starvation period. Consequently, a comparison between cells exposed to a Starvation period and cells only exposed to dexamethasone (40 μM) in the Growth Medium was performed. See Example 16. To compare the different protocols, the RLU results for Graves' Positive and Graves' Negative serum were averaged together and their respective percentages above the Reference standards were calculated. Table 10.

TABLE 10

Comparison Of Starved vs. Dexamethasone Treated CHO-rMc4 Cells

|  | CHO-Mc4 Non-Starvation Protocol | | | CHO-Luc Protocol (Starvation) | | |
| --- | --- | --- | --- | --- | --- | --- |
|  | MC4 w/Dex | Mc4 w/o Dex | Luc | MC4 w/Dex | Mc4 w/o Dex | Luc |
| Positive (n = 4) | 12555 | 11023 | 1747 | 7978 | 4866 | 2486 |
| Negative (n = 5) | 1931 | 1885 | 1040 | 445 | 492 | 749 |
| Reference (n = 1) | 3436 | 5827 | 972 | 957 | 1129 | 691 |
| Positive (n = 4) | 365% | 189% | 179% | 834% | 431% | 360% |
| Negative (n = 5) | 56% | 32% | 107% | 46% | 44% | 108% |
| Reference (n = 1) | 100% | 100% | 100% | 100% | 100% | 100% |

The data demonstrate that non-starved CHO-RMc4luc cells with dexamethasone provides a more sensitive (and therefore more accurate) detection of circulating TSI's as compared to non-starved CHO-RMc4luc cells without dexamethasone. For example, in the Graves' Positive patient serums not subjected to a Starvation period, CHO-rMc4luc cells with dexamethasone showed a 365% increase in luminescence (as relative to the Reference) while CHO-rMc4 cells without dexamethasone showed a 189% increase in luminescence.

The improvement in sensitivity and accuracy with dexamethasone is even more dramatic when comparing the Grave's Positive patient serums with the Grave's Negative patient serums. For example, in the presence of dexamethasone the difference between Grave's positive and Grave's negative serums is 309% (i.e., for example, 365%-56%) but in the absence of dexamethasone the difference between Grave's positive and Grave's negative serums is 157% (i.e., for example, 189%-32%).

These results clearly show that dexamethasone provides a better assay system in terms of sensitivity due to a stronger luminescent signal strength. Such an improvement results in improved testing accuracy and when combined with the RMc4luc testing platform, the present invention contemplates a diagnostic assay that is more rapid and accurate than any previously disclosed TSI antibody assay requiring a Starvation medium period.

Further studies demonstrated that this effect was not limited to dexamethasone but can be expected from most, if not all, glucocorticoids. For example, the data presented herein show that other glucocorticoids also improve the sensitivity of the CHO-RMc4luc assay to provide equivalent sensitivity in comparison with substitution for a Starvation medium period. Nonetheless, the presence of a glucocorticoid provides the advantage that the assay can be performed in two days, rather than three days.

Alternative glucocorticoids (GCs) where compared to dexamethasone (40 μM) on the basis of Relative Light Units (RLUs) and Serum Reference Ratios expressed in percentages (SRRs %). For this purpose, all five (5) tested glucocorticoids show a generic effect in improving the sensitivity of the RMc4luc assay in the absence of a Starvation period.

The data was collected in accordance with the protocol outlined in Example 17. The data was calculated as the difference (Δ) in RLU values or SRR % values for each glucocorticoid (GC) concentration by subtracting the RLU value or SRR % value for the Normal control at that concentration from the RLU value or SRR % value for the Positive control at that concentration, respectively.

Figure 17:
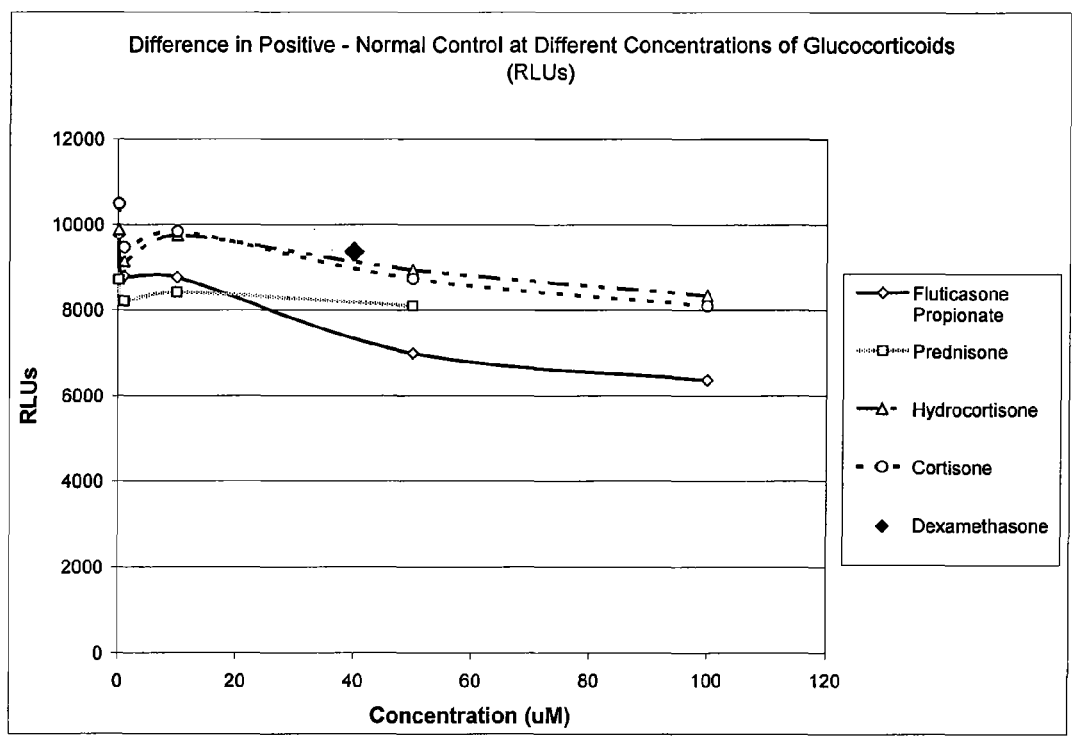
FIG. 17 present exemplary Relative Light Unit (RLU) data showing that the alternative glucocorticoids fluticasone, prednisone, hydrocortisone and cortisone provide equal signal intensities of the CHO-RMc4 assay when compared to 40 μM dexamethasone.
Figure 18:
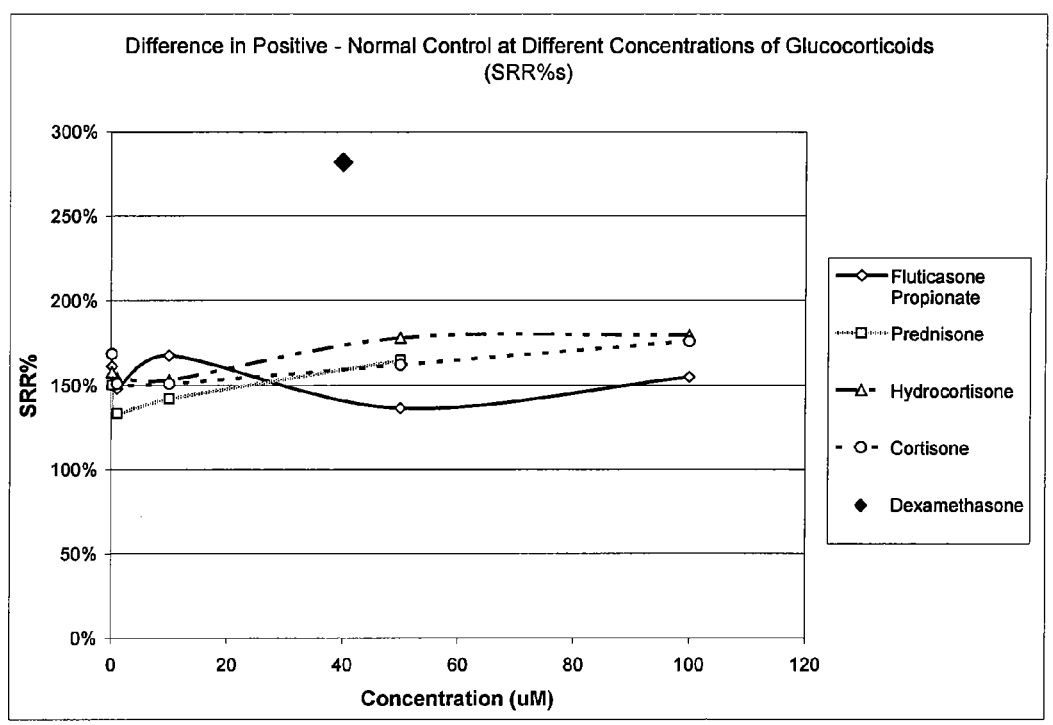
FIG. 18 present exemplary Serum Reference Unit percentages (SSR %) data showing that the alternative glucocorticoids fluticasone, prednisone, hydrocortisone and cortisone provide an improved CHO-RMc4 assay.

The data demonstrate that all four GCs improve signal intensity by at least 6000 RLUs, wherein hydrocortisone and cortisone have signal intensities equivalent to dexamethasone. See, FIG. 17. When the data was calculated as SRR %, however, it can be seen that dexamethasone improves signal-to-noise ratio by approximately 2-fold when compared to all the alternative GCs. See, FIG. 18. Nonetheless, the data demonstrate that any glucocorticoid can provide improvements in RMc4luc assay sensitivity and accuracy such that a Starvation medium period is not required.

VII. Kits

In yet other embodiments, the present invention provides kits for performing Graves' disease diagnostic assays using chimeric TSH receptors. The kits preferably include one or more containers containing a cell line-based diagnostic method of this invention. In some embodiments, the containers may contain a glucocorticoid including, but not limited to, dexamethasone, cortisone, hydrocortisone, prednisone, or fluticasone. In some embodiments, the kits contain all of the components necessary or sufficient for performing a Grave's disease diagnostic assay to detect circulating TSH autoantibodies in patient sera, including all controls, directions for performing assays, and any software for analysis and presentation of results. In some embodiments, the kits contain vectors encoding chimeric TSH receptors capable of transfecting cell lines. In some embodiments, the kits comprise all materials necessary or sufficient to perform diagnostic assays in a single reaction and provide diagnostic, prognostic, or predictive information (e.g., to a researcher or a clinician). For example, such a kit might contain a cell line comprising a chimeric TSH receptor and a luciferase reporter system. In some embodiments, the kits comprise one or more of a vector comprising a first nucleic acid sequence for an Mc4 chimeric TSH receptor, a second nucleic acid sequence for a luciferin/luciferase reporter system, and a third nucleic acid sequence for a promoter. Other embodiments also include buffers, control reagents, detection devices, software, instructions, and TSH autoantibody standard preparations.

The kits may also optionally include appropriate systems (e.g. opaque containers) or stabilizers (e.g. antioxidants) to prevent degradation of the reagents by light or other adverse conditions. Each solution or composition may be contained in a vial or bottle and all vials held in close confinement in a box for commercial sale.

The kits may optionally include instructional materials containing directions (i.e., protocols) providing for the use of the reagents in the diagnosis, detection, and/or treatment of Graves' disease. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); or L (liters); ml (milliliters); µl (microliters); µIU (micro International Units); cm (centimeters); mm (millimeters); µm (micrometers); nm (nanometers); °C. (degrees Centigrade); sec. or s (second(s)); min. and m (minute(s)); MW (molecular weight); thyroid stimulating hormone or thyrotropin (TSH); bTSH (bovine TSH); TSI (thyroid stimulating immunoglobulin); TSAb (thyroid stimulating antibodies); EDTA (ethylene diamine tetraacetic acid); RLU/sec (relative light units per second); GM or PM (Growth Medium or Planting Medium); SM (Starvation Medium); HBSS (Hank's Balanced Salt Solution); EMEM (Eagle's Minimum Essential Medium); FBS or FCS (fetal bovine serum or fetal calf serum); DMSO (dimethyl sulfoxide); CHO (Chinese hamster ovary cells); CHO-R (CHO cells transfected with the human TSH receptor; CHO-Rluc (CHO-R cells transfected with the cre-luciferase reporter gene complex); Oxoid (Oxoid, Basingstoke, England); BBL (Becton Diclinson Microbiology Systems, Cockeysville, Me.)); DIFCO (Difco Laboratories, Detroit, Nil); U.S. Biochemical (U.S. Biochemical Corp., Cleveland, Ohio); Fisher (Fisher Scientific, Pittsburgh, Pa.); Sigma (Sigma Chemical Co., St. Louis, Mo.); ATCC (American Type Culture Collection, Rockville, Md.); LTI (Life Technologies, Rockville, Md.); and Promega (Promega Corp., Madison, Wis.).

In the following methods, all solutions used in these methods were sterile (with the exception of TSH, controls, patient specimens) and treated aseptically. All manipulations were conducted in a biosafety cabinet under aseptic conditions. Cell culture media (e.g., Ham's F-12, EMEM, etc.) were obtained from LTI, while additive reagents such as non-essential amino acids were obtained from Sigma.

Freezer vials of cells should not be allowed to warm from their −80° C. (or lower) storage temperature until immediately prior to thawing and use in the methods of the present invention, as cycling of the temperature may result in viability losses. Because it contains dithiothreitol, which is unstable at room temperatures, the 5× cell lysis solution should be removed from its −20° C. storage temperature only long enough to remove the required volume for preparation of the 1× solution. As it also contains dithiothreitol, reconstituted luciferase substrate solution should be kept frozen at −20° C. until just prior to use, at which time it may be removed and placed in a 25-37° C. water bath to thaw and reach room temperature.

In general, when removing liquid from wells (e.g., microtiter plates, etc.), the liquid may be dumped from the wells into a receptacle in a biosafety hood. The residual liquid can be drained and removed by placing the plate upside down on a sterile, absorbent wipe. Or, the liquid may be removed by aspiration using a fine tip on the aspirator. If aspiration is used, the plate is held at a steep angle so that the liquid does not overflow the wells, and the aspirator tip is directed down the side of the well almost to the bottom to remove the liquid and only leave minimal residue. However, care must be exercised in order to prevent disturbance of the cell monolayer, as the cells can be easily removed by the aspirator.

As indicated in the methods below, it is recommended that specimens, standards, and controls be run in triplicate. Because of the viscous nature of Solution 3 and the difficulty in achieving adequate mixing in the wells, the best reproducibility was achieved when the total triplicate volume is +10% (33 µl) of these reagents is transferred to the required triplicate volume +10% (330 µl) of Solution 3, thoroughly mixed, and 110 µl transferred to the triplicate wells.

In the preparation of cell monolayers (e.g., within the wells of microtiter plates), it is preferred that the cells be distributed evenly within the wells. Thus, in order to avoid uneven cell distributions, the transfer of cell suspensions into wells should be performed in a vibration-free biosafety hood. After all of the wells in a plate have received cells, the plate is covered and carefully placed on a solid, vibration-free surface, for 30 minutes, to allow the cells to attach undisturbed, to the bottom of the wells. This helps ensure that an even distribution of cells is present in each of the wells.

Example 1

Preparation of Cho-Rluc Cells for Testing

In these experiments, CHO-Rluc cells were prepared from W-25 CHO-R cells for use in the testing methods to detect TSI in Graves' disease patients. Pools of puromycin-resistant cells were obtained and tested for light output in response to bovine TSH. Clones with the highest light output were selected for use in the experiments described below.

CHO-Rluc cells were grown in cell culture flasks (e.g., T-225 flasks) in growth medium containing Ham's F-12 medium, 10% FBS (heated at 56° C. for 30 minutes to inactivate complement), 2 mM glutamine, and 1× non-essential amino acids. The flasks were incubated at 35-37° C., in a humidified atmosphere, containing 5% carbon dioxide.

After the cell cultures reached confluence, the medium from each flask was aspirated, and the cell monolayers were washed with HBSS without Ca and $Mg^{++}$. Then, 7 ml of a 0.25% trypsin/1 mM EDTA solution were added to each flask, and allowed to react with the monolayers for approximately 5-10 minutes at room temperature, in order to detach and disperse the cells in a nearly unicellular suspension. The cell suspensions were then centrifuged for approximately 5 minutes at 300-400×g. The supernatants were then removed and the pelleted cells resuspended in 8 ml of a medium prepared by mixing 4 ml EMEM containing 1×HBSS and 20% FBS with 4 ml of cryoprotective medium (EMEM containing 1×HBSS and 15% DMSO).

An aliquot of each cell suspension was then used to determine the number of cells present in the suspension. This determination can be accomplished using any method known in the art, including but not limited to methods using a hemocytometer to determine the cell count. Thus, it is contemplated that any method can be used to determine the cell count in the suspensions. Based on the number of cells in the suspension, the cells were aliquoted by volume to approximately $2 \times 10^6$ cells into standard freezer vials. The cells were then stored frozen at −90° C. for short-term storage. For long-term storage, the cells were stored in liquid nitrogen (about −200° C.).

Example 2

CHO-Rluc Assay Plate Preparation and Testing

In these experiments, CHO-Rluc cells prepared as described in Example 1 were used in assays for diagnosis of Graves' disease. To prepare 24 monolayers for testing, 24 wells in a 96-well microtiter plate were first treated by adding 50-100 µl 0.1% gelatin solution (Sigma) to enhance attachment of the cells to the bottom of the 24 wells chosen for the test. Following incubation for approximately 1 minute at room temperature, the gelatin solution was removed from each of the wells by aspiration. It was noted that the gelatin can remain on the wells for longer than one minute. The gelatin serves to coat the wells with collagen, so that the cells attach more quickly to the wells and reach confluence more rapidly. However, cells can be planted and grown to confluence without gelatin and still perform well.

A freezer vial of CHO-Rluc cells produced as described in Example 1 was rapidly thawed in a 37° C. water bath to provide approximately 0.4 ml cell suspension, which was well-mixed using a pipette. The cells were then added to 2.5 ml GM (also referred to as "Planting Medium"), thoroughly mixed by vortexing for 1-2 seconds, and 100 μl aliquots of the cell suspension were added to each well, and the plates were covered. It is preferable to produce an even distribution of cells in each well. Thus, to avoid uneven cell distributions, the microtiter plate should be placed in a vibration-free hood for cell planting and attachment of cells to the walls of the microtiter plate. The planted cells were then incubated at 35-37° C., in a humidified atmosphere, containing 5% $CO_2$, for approximately 20-24 hours, to allow the cells to form a nearly or completely confluent monolayer.

The GM was then aspirated from each well as completely as possible, being careful not to disturb the monolayers (i.e., confluent monolayers remain in the wells). The monolayers were rinsed with approximately 100 μl Starvation Medium (HBSS containing $Ca^{++}$ (0.14 g/L) and $Mg^{++}$ (0.048 g/L) per well. The Starvation Medium was aspirated and a fresh 100 μl of Starvation Medium was then added to each well. It is important that these steps be conducted sufficiently rapidly that the cell monolayers do not dry. The plates were then incubated overnight in a 35-37° C., 5% $CO_2$, humidified incubator. Following incubation, the Starvation Medium was aspirated from the wells, using care to avoid disturbing the monolayers. Then, approximately 100 μl Stimulation Medium were added to each monolayer, again working quickly so that the monolayers did not dry.

Then, in an alternative method to that previously described, 10 μl of patient, control, and TSH standard solutions were added to the appropriate wells. The TSH standards and IgG samples were diluted with diluent (i.e., HBSS-NaCl+222 mM sucrose). The TSH standards were tested at concentrations of 0, 10, 100, 1000, and 5000 μIU. Patient samples were diluted to a concentration of 10 mg protein/ml for use in the assay. As the Stimulation Medium is viscous, thorough mixing of the suspensions was important. Adequacy of the mixing was ascertained by microscopic examination of the monolayers. The plates were incubated for 4 hours at 35-37° C. in a 5% $CO_2$, humidified incubator. The medium was carefully aspirated from each well and 150 μl lysis solution (Promega) was added to each well. The lysis solution contained 25 mM Tris-phosphate, pH 7.8, 2 mM diaminocyclohexane tetraacetic acid (CDTA), 2 mM dithiothreitol (DTT), 10% glycerol, and 1% Triton X-100. The plates were then incubated for 30 minutes at room temperature, to allow the monolayers to lyse. Following lysis, each well was scraped and stirred using a pipet tip. Then, 25 μl of lysate were removed from each well and placed in a luminometer tube (12×75 mm, polypropylene), and 50 μl of luciferase substrate (Promega) were then added. The tubes were vortexed for 1-2 seconds and the RLU/sec values determined, using settings of 5 seconds delay and 10 second read. To obtain average net values, the average of the "0 TSH" (i.e., the negative control) samples was subtracted from all test average values.

Example 3

Preparation of IgG Samples

In these experiments, patients' IgG was prepared for testing in the present methods. Lyophilized IgG samples from 38 well-known and characterized, untreated Graves' disease patients were kindly provided by Dr. B. Y. Cho (Department of Internal Medicine, Seoul National University, College of Medicine, Seoul, Korea). As most of the samples had been previously tested in standard methods using CHO-R and FRTL-5 cells, these test results were known for 35 of these samples.

In preparation for lyophilization, the IgGs were affinity-purified using protein A-Sepharose CL-4B columns, as known in the art, and then dialyzed against 100 volumes of distilled water at 4° C. The dialysis water was changed every 8 hours over a 2 day period. After removal of denatured protein by centrifugation at 1500×g for 15 minutes at 4° C., the IgG was lyophilized and stored at −20° C. until used in the experiments described herein.

In some experiments, purified untreated Graves' IgG was diluted in normal serum (euthyroid sera discussed in Example 7, below), and assayed using the CHORluc assay described below.

Example 4

CHO-Rluc Assays

In these experiments, the performance of CHO-Rluc cells using the method described by Evans et al. (Evans et al., J. Clin. Endocrinol. Metabol., 84:374 (1999)) was evaluated. The media from the cell monolayers in the 24 wells used in the 96-well microtiter plates prepared as described in Example 2 were aspirated and replaced with 100 μl Ham's F-12 medium containing 10% charcoal-stripped calf serum (Sigma), and incubated overnight at 35-37° C., in a humidified atmosphere containing 5% $CO_2$.

Then, 10 μl of bovine TSH standards diluted to a range of concentrations (e.g., 0 10, 100, and 1000 μIU) and Graves' IgG (dissolved to a concentration of 10 mg protein/ml in charcoal-stripped calf serum) were added to respective quadruplicate wells. The suspension in each well was mixed, and the plates were incubated for 4 hours at 35-37° C., in a humidified atmosphere containing 5% $CO_2$. The medium was then aspirated from each of the wells, and 150 μl of lysis buffer (Promega, as described above) were added to each well. The plates were then incubated at room temperature for 30 minutes to allow lysis of the cells in the wells. Then, 25 μl of each lysate were transferred to a 12×75 polyethylene luminometer tube, to which 50 μl of luciferase substrate (Promega) were added immediately prior to mixing and reading in the luminometer at settings of 5 seconds delay and 10 second read. The luminometer read out provided results as relative light units per second (RLU/sec). The negative or "zero" TSH standard value was subtracted from each of the readings. In one run, the average net value for the zero μU/ml TSI standard was 68,011 RLU/sec, while the result for the sample containing 10 μIU/μl was 4031 RLU/sec, the sample containing 1000 μIU was 222,801 RLU/sec, one Graves' IgG test sample was 384 RLUTsec (sample #1), and another Graves' IgG test sample was −3012 RLU/sec (sample #9).

The Graves' IgG sample #1 and sample #9 were previously assayed using standard FRTL-5 cells and a cAMP RIA assays. In the cAMP assay, values greater than 153 with FRTL-5 cells are considered positive for the presence of TSI.

The cAMP value with FRTL-5 cells for sample #1 was 212, and the cAMP value for sample #9 was 803. The CHO-R values for these same samples (#1 and #9) were 116 and 1733, respectively, in an assay system where CHO-R values greater than 173 are considered to be positive for Graves' disease. Thus, these results clearly indicate that there is a discrepancy between the results obtained using different cell lines for the detection of Graves' disease. Indeed, the use of the Evans et al. method yielded negative results for both IgG samples, indicating that this system with CHO-Rluc is useless for detecting human TSI, despite the fact that the response to bovine TSH was very good.

Furthermore, during the development of the present invention (as described below), it was determined that if the CHO-Rluc cells were planted in a medium containing charcoal-stripped calf serum for 24 hours (i.e., to reach confluence), the cells simply attached to the bottom of the wells, but did not multiply and become confluent during the incubation period, unlike the situation in which normal FBS was used. Thus, this surprising result indicates that the use of charcoal-stripped serum in the medium resulted in a starvation step for the cells, somewhat analogous to the incubation of FRTL-5 cells in 5H medium.

In some experiments purified, untreated Graves' IgG diluted in normal serum, were tested in the CHO-Rluc assay (with PEG). For IgG #10, (2 mg/ml), the RLU/sec value was 131,461; for IgG #15 (2 mg/ml), the RLU/sec value was 180,327; for IgG #27 (5 mg/ml), the RLU/sec value was 179,777; and for IgG#32 (5 mg/ml), the RLU/sec value was 112,627. These results clearly show that the CHO-Rluc assay measures TSI in the presence of serum.

Example 5

Development of Media Formulations

In view of the previously-described experiments, the effects of different media formulations were investigated for use with the CHO-Rluc cells in the measurement of bovine TSH and human TSI. In these experiments, various media formulations were tested for the "starvation," and "stimulation" steps in the CHO-Rluc assay, using bTSH standards and IgG extracted from the sera of Graves' disease patients.

In these experiments, once the cell monolayers contained within the wells of 96-well microtiter plates (as described above), reached confluence, the Growth Medium was removed by aspiration and 100 µl of Starvation Medium were added to each monolayer. The plates were then incubated for 16-24 hours at 35-37° C., in a humidified atmosphere containing 5% $CO_2$, to starve or condition the cells. The Starvation Medium was then aspirated from the wells.

To perform the assay, 10 µl of the patient specimen IgG, bTSH standards, and IgG controls (normal and Graves' disease sera), were added to the monolayers in triplicate. The suspensions were mixed within each well, and incubated under the above conditions for 4 hours. The liquid was then removed from each monolayer by aspiration, and 150 µl of lysis buffer (Promega, as described above) were added to each well. The plates were allowed to incubate at room temperature for 30 minutes to lyse the cells in the monolayers.

In order to measure the amount of cell stimulation caused by the TSH standard or antibody to the TSH receptor, the luciferase in the cell lysates was measured by adding 25 µl of lysate to a luminometer tube to which 50 µl of substrate solution (Promega) were added. The suspensions were mixed and then read in a luminometer with settings of a 5 second delay and a 10 second read, to determine the RLU for each sample.

In order to use the cells for TSI or TSH stimulation, the Starvation Medium was removed by aspiration, and 100 µl of the Stimulation Medium were added to each well. This Stimulation Medium was HBSS-NaCl+222 mM sucrose. The following Table 2 provides a comparison of the formulations of HBSS-NaCl+222 mM sucrose and standard HBSS.

TABLE 2

HBSS Medium Formulation Comparisons

| Component | HBSS--NaCl + 222 mM Sucrose (g/L) | Standard HBSS (g/L) |
|---|---|---|
| $CaCl_2$ | 0.144 g/L | 0.14 g/L |
| KCl | 0.373 | 0.400 |
| $KH_2PO_4$ | 0.060 | 0.060 |
| $MgSO_4$ | 0.048 | 0.048 |
| $Na_2HPO_4$ | 0.097 | 0.048 |
| $NaHCO_3$ | 0.00 | 0.35 |
| NaCl | 0.00 | 8.00 |
| D-Glucose | 1.00 | 1.00 |
| Sucrose | 76.00 | 0.00 |
| HEPES | 4.77 | 0.00 |
| Bovine Serum Albumin | 10.00 | 0.00 |

This Stimulation Medium formulation is a formulation that is commonly used in the measurement of TSI in FRTL-5 and CHO-R cells.

The results of experiments to test various Starvation Medium formulations are indicated in the following Table 3. In these experiments, the HBSS-NaCl+222 mM sucrose Stimulation Medium was used. As indicated in Table 3, the standard HBSS with 20 mM sucrose yielded the best signal to noise ratio (i.e., the lowest background and highest value for Graves' IgG).

TABLE 3

RLU/Sec Results for Various Media: Growth Versus Starvation

| Medium | RLU/Sec | | | |
|---|---|---|---|---|
| | 0 TSH | 10 µIU TSH/ml | 1000 µIU TSH/ml | #13 IgG |
| CHO GM[a] | (66,232) | 782 | 265,195 | 5,144 |
| CHO Char[b] | (50,638) | 5,602 | 229,492 | 34,042 |
| HBSS--NaCl + 222 mM Sucrose[c] | (32,289) | 2,188 | 142,666 | 30,640 |
| Standard HBSS with 20 mM Sucrose[c] | (27,139) | 14,390 | 156,548 | 53,994 |

[a]CHO GM is CHO Growth Medium containing 10% FBS.
[b]CHO Char. is CHO Growth Medium with 10% charcoal-stripped calf serum.
[c]A Starvation Medium Example 6

Use of PEG

As PEG may be used in in vitro antigen/antibody reactions to assist or enhance the reaction rate, a trial was conducted in which PEG was incorporated into the Stimulation Medium. As this compound may decrease the off-rate or dissociation of the antigen/antibody complex, the use of PEG in the methods of the present invention was investigated.

Preliminary results with 12% PEG-8000 (i.e., ave. MW 8,000) in HBSS-NaCl sucrose, resulted in monolayers with increased spaces between the cells. To reduce this apparent osmotic stress, 6% PEG-8000 in HBSS-NaCl+111 mM sucrose was tested. In these experiments, the Starvation Medium yielding the best results (i.e., standard HBSS+20 mM sucrose) was used. The results are shown in Table 4, below.

TABLE 4

RLU/Sec Results for Stimulation Media With and Without PEG

| | RLU/Sec | | | |
|---|---|---|---|---|
| Stimulation Medium | 0 TSH | 10 µIU TSH/ml | 1000 µIU TSH/ml | #13 IgG |
| HBSS--NaCl + 222 mM Sucrose | (21,671) | 1,336 | 82,466 | 39,082 |
| HBSS--NaCl + 111 mM Sucrose + 6% PEG-8000 | (32,562) | 5,980 | 207,831 | 174,461 |

As indicated in Table 4, the incorporation of 6% PEG-8000 significantly and substantially enhanced the luminescent signal from the CHO-Rluc cells, in response to added bTSH, as well as Graves' IgG.

An additional experiment was conducted to determine the optimal concentration of PEG-8000 to use in the Stimulation Medium. The net values for one Graves' sample (Graves' IgG #20), with an FRTL-5 cAMP value of 957, are shown in Table 5. As indicated in Table 5, 6% PEG yielded maximum signal for Graves' TSAb.

TABLE 5

RLU/Sec Results for Various PEG Concentrations

| | % PEG In Stimulation Medium | | | | |
|---|---|---|---|---|---|
| Results | 2% | 4% | 6% | 8% | 10% |
| RLU/sec | 15,566 | 52,259 | 87,908 | 73,260 | 47,991 |

Subsequent experiments have shown that the Starvation Medium need not contain 20 mM sucrose, as there is no statistically significant difference in the results with or without it.

In addition, experiments were conducted to demonstrate that the assay of the present invention measures thyroid-stimulating immunoglobulin in a dose-dependent manner. In these experiments, three Graves' disease IgG samples (#6, #11, and #16) were tested. Serial 3-fold dilutions were made using the Stimulation Medium containing 6% PEG-8000, and the methods described above. The results are shown in FIG. 1, which shows the linearity of the dilutions. The IgG samples were prepared from 10 mg/ml stocks, which were then tested undiluted, and serially diluted (3-fold dilutions) to 0.3333, 0.1111, 0.0371, 0.0123, and 0.0041 dilutions (i.e., to yield 3.333 mg/ml, which was then diluted 3-fold to yield 1.111 mg/ml, etc.).

The FRTL-5 value for IgG sample #6 was 2080, while the FRTL-5 value for IgG sample #11 was 4453, and for IgG sample #16, the value was 830. The following Table 6 lists the results for each of these samples. The correlation coefficients (r) were 0.857 for IgG sample #6, 0.858 for sample #11, and 0.995 for sample #16.

TABLE 6

Dose-Response (Dilution) Curves of Graves' IgG Specimens*

| | Dilution Factor | | | | | |
|---|---|---|---|---|---|---|
| Sample | 1 | 0.3333 | 0.1111 | 0.0371 | 0.0123 | 0.0041 |
| IgG #6 | 176,123 | 159,694 | 62,115 | 13,480 | −6,628 | −2,574 |
| IgG #11 | Not Done | 368,373 | 324,143 | 158,641 | 77,298 | 30,166 |
| IgG #16 | 222,413 | 90,646 | 40,048 | 8,093 | −1,705 | −691 |

*All values are reported as RLU/sec.

Example 7

Alternative Protocol Using PEG

In these experiments, alternative protocols using PEG were tested. First, freezer vials of CHO-Rluc cells were thawed, diluted in Growth Medium (the contents of each cell vial were added to 2.5 ml medium), and 100 µl of this cell suspension were added to each of the 24 gelatin-coated wells of a 96-well microtiter plate, prepared as described previously. The plates were incubated for 20-24 hours in a 35-37° C., humidified incubator with an atmosphere containing 5% $CO_2$. This provided monolayers that were loosely confluent.

The Growth Medium was removed and the monolayers rinsed with 100 µl of Starvation Medium (normal HBSS with $Ca^{++}$ and $Mg^{++}$), and a final 100 µl were added to each monolayer before incubating overnight under the conditions described above. Following incubation, the Starvation Medium was removed and 100 µl of Stimulation Medium containing 6% PEG (i.e., as described above) were added to each monolayer. Then, 10 µl of each of the standards and samples were placed into the wells (in triplicate). While other volumes were tested (e.g., 25 µl, 50 µl, and 75 µl), the values obtained were substantially equivalent to those obtained with 10 µl volumes. Thus, the smaller volume was used in order to conserve the samples and reagents, and to minimize the concentration of potentially interfering substances present in some serum samples.

The well contents were mixed and the monolayers incubated as described above for 4 hours (i.e., a stimulation step). The medium was removed from each well, and 150 µl of lysis solution (as described above) were added to each well. The monolayers were allowed to stand at room temperature for 30 minutes for lysis to occur. Then, 25 µl of each lysate were added to individual luminometer tubes. Fifty microliters of luciferase substrate (as described above) were added to each tube, the contents mixed, and the tubes immediately read in a luminometer with settings of 5 seconds delay and a 10 second read time.

In an experiment to determine the normal range of euthyroid sera, 24 specimens obtained from a reference laboratory were run using the CHO-Rluc assay as described above. The sera were euthyroid in that none of the samples were submitted for thyroid testing. The mean (55,334 RLU/sec) and standard deviation (1 SD 7,434 RLU/sec) were calculated for these 24 euthyroid samples. The results are shown in FIG. 7. The SD value was then multiplied by three, which yielded a cut-off for normal, non-Graves' disease values of 77,636 RLU/sec. This cut-off encompasses >99% of the normal population; values greater than this were considered to be TSI positive.

In a separate set of experiments, a group of 17 patient specimens which previously been tested by a commercial esoteric testing laboratory using cAMP RIA and FRTL-5 cells for TSI, were tested using the CHO-Rluc cells with the above procedure. The FRTL-5 test results indicated 16 of the patient specimens were negative for TSI (i.e., only one was positive). The single positive specimen identified by the FRTL-5/cAMP assay (258% or 1.98× the cut-off, where the assay cut-off was 130%), was likewise positive by the CHO-Rluc assay (190,691 RLU/sec) based on a 2.45× cut-off of 77,636 RLU/sec, as shown in FIG. 7. The CHO-Rluc values of the 16 patient specimens which were negative (i.e., normal) by the FRTL-5/cAMP assay were found to be in good agreement with the 24 normal sera used to establish the normal range for the assay. See, FIG. 7.

Example 8

Comparison of CHO-Rluc Method and Standard Methods

Figure 4:
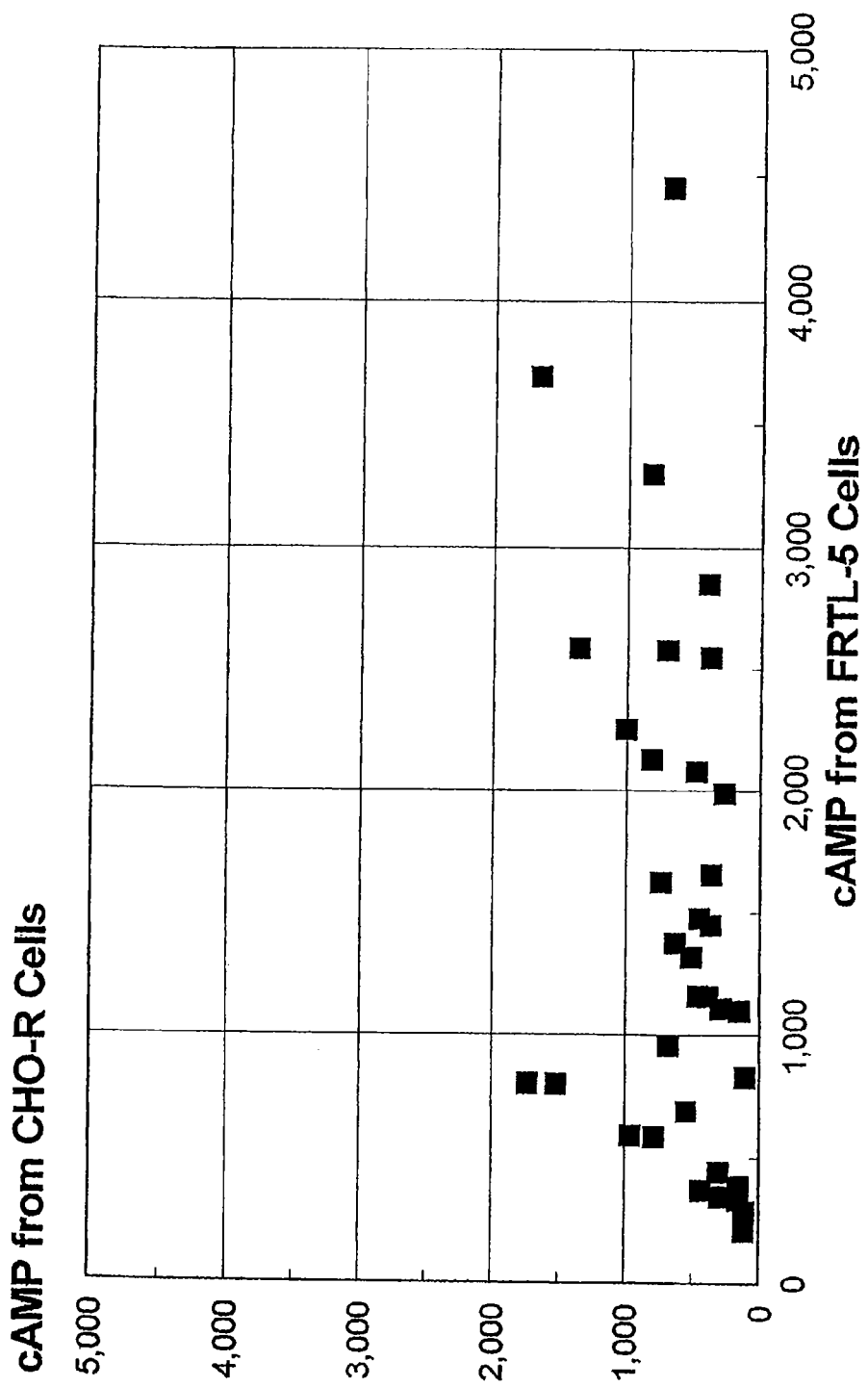
FIG. 4 provides a comparison of CHO-R cAMP results with FRTL-5 cAMP results for IgGs from 35 untreated Graves' patients.
Figure 5:
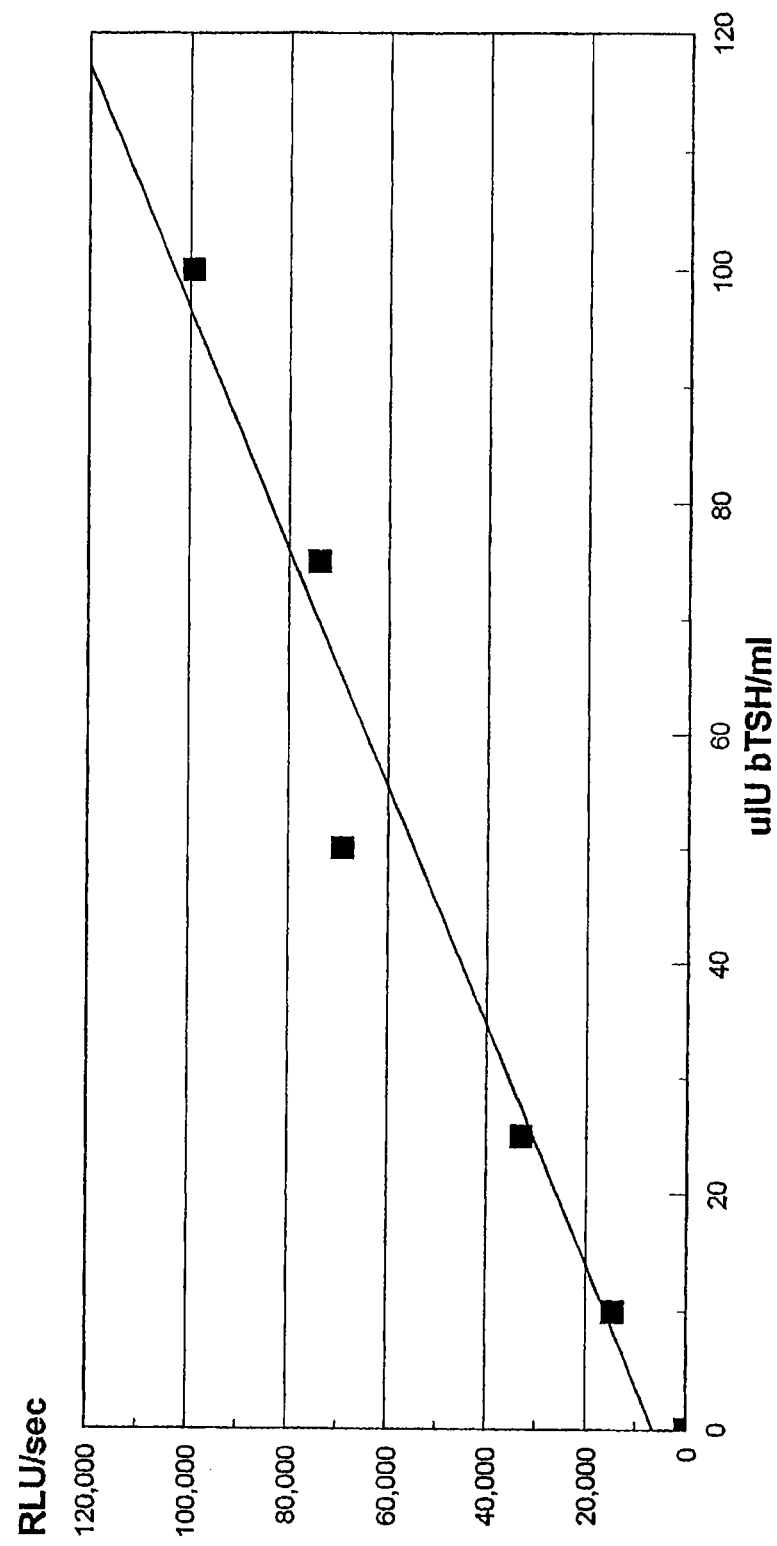
FIG. 5 shows the linearity of the response to bTSH of the CHO-Rluc cells.

In these experiments, the methods of the present invention utilizing Stimulation Medium containing 6% PEG-8000 were compared with methods using the standard HBSS-containing Starvation Medium and Stimulation Medium, to obtain luciferase values for 35 of the untreated Graves' disease IgG specimens obtained from Dr. Cho. The cAMP values obtained by Dr. Cho with FRTL-5 and CHO-R cells using the same IgG samples as used in methods of the present invention are shown in comparison with the CHO-R luciferase results in FIGS. 2, 3 and 4. FIG. 5 shows the linearity of luciferase response to bTSH.

Figure 2:
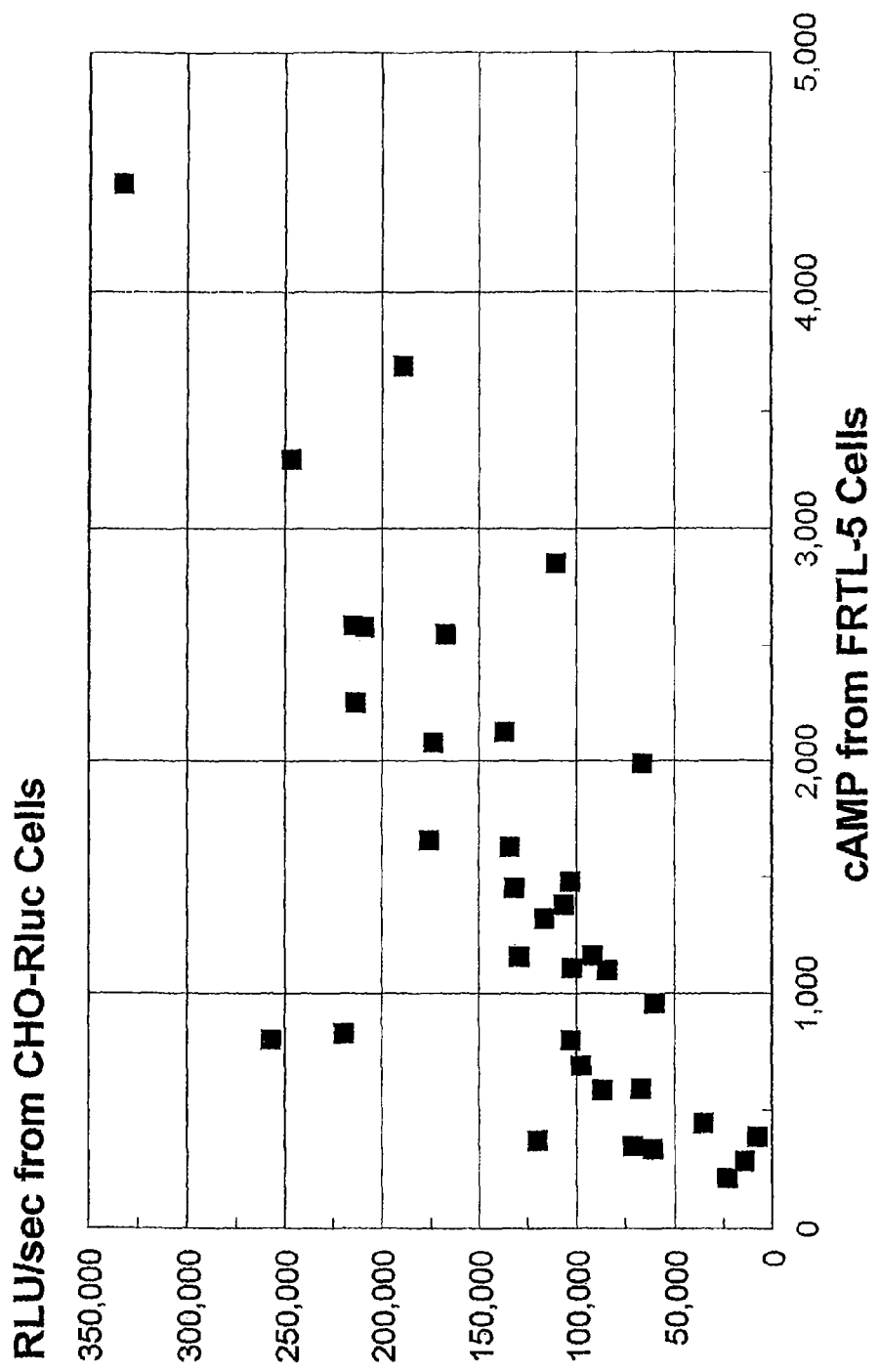
FIG. 2 provides a comparison of CHO-Rluc luciferase results with the FRTL-5 cAMP results for IgGs from 35 untreated Graves' patients.
Figure 3:
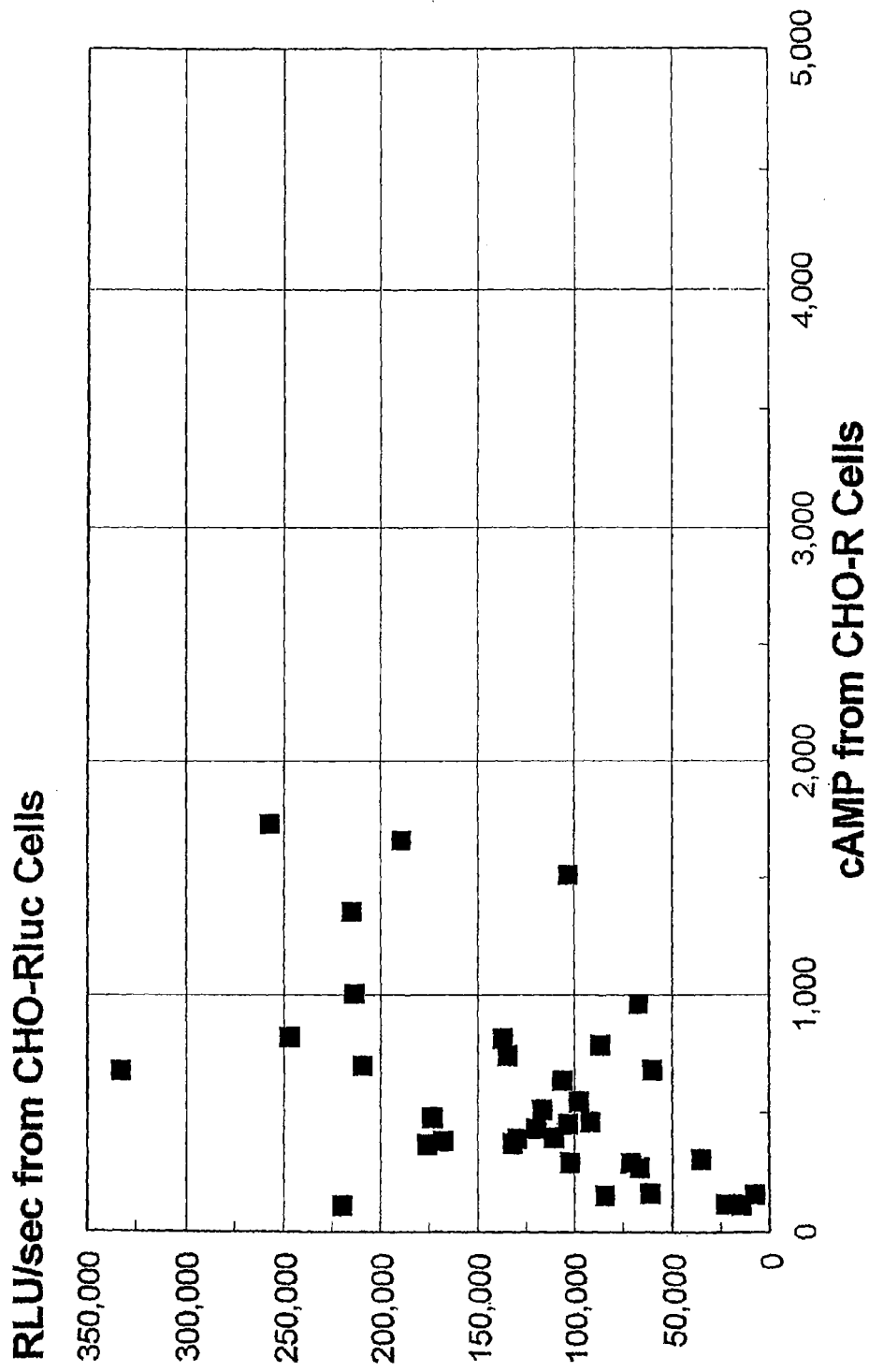
FIG. 3 provides a comparison of CHO-Rluc luciferase results with CHO-R cAMP results for IgGs from 35 untreated Graves' patients.

FIG. 2 provides a comparison of CHO-Rluc luciferase results with the FRTL-5 cAMP results. This Figure indicates that the correlation between these methods is quite good. FIG. 3 provides a comparison of CHO-Rluc luciferase results with CHO-R cAMP results. The CHO-R CAMP cut-off value was 173. Values below this cutoff were as follows (CHOluc RLU/sec): 110 (219,913), 113 (14,434), 116 (25,373), 152 (84,493), 156 (7576), and 161 (61,321). As indicated in this Figure, the range of CHO-R cAMP results is relatively narrow, as compared with the CHO-Rluc values. This is also shown in FIG. 4, which provides a comparison of CHO-R cAMP results with FRTL-5 cAMP results. The CHO-R value was 173. The FRTL-5 cut-off value was 153. Values below cutoff were as follows (FRTL-5 values): 110 (830), 113 (283), 116 (212), 152 (1100), 156 (388), and 161 (335). The average +/−SD values for the IgG Control (ICN), for the tests shown in FIG. 2 were 472+/−4015 (n=8).

FIG. 5 shows the linearity of the response to bTSH of the CHO-Rluc cells. In these experiments, dilutions of bTSH were tested. The RLU/sec values obtained are shown in Table 7, below.

TABLE 7

Results for bTSH Dilutions

| | μIU TSH · ml | | | | | |
|---|---|---|---|---|---|---|
| Results | 0 | 10 | 25 | 50 | 75 | 100 |
| RLU/sec | 0 | 5,921 | 20,227 | 34,426 | 54,396 | 62,206 |

It is contemplated that this linearity and sensitivity of response to bTSH will prove useful in the detection of blocking antibodies to the TSH receptor (e.g., those autoantibodies in patents with atrophic thyroiditis and Hashimoto's thyroiditis which block the TSH receptor, thereby preventing thyroid hormone production and release resulting in hypothyroidism). This Figure also provides at least a partial explanation of why the CHO-R cell line is not as sensitive to TSI from Graves' disease patients sera as the FRTL-5 cell line. In these results, the correlation coefficient (r) was 0.9925. The three S.D. (standard deviations) sensitivity was 1.3 μIU TSH/ml.

Example 9

Monitoring of Immune Responses

In these experiments, the immune response of vaccine recipients is measured and monitored. Although it is not intended that the present invention be so limited, this Example describes the monitoring of a subject's immune response to herpes simplex (HSV) vaccine.

Prior to administration of vaccine, a serum sample (i.e., preimmune serum) is collected from the subject for use as a baseline or control, and stored frozen until testing. Serum samples are also collected at periodic intervals following administration of the vaccine (e.g., 1-2 weeks, 1 month, 2 months post-vaccination, etc.). The sera are thawed as necessary, and used in an assay to determine the presence and quantity (i.e., titer) of neutralizing antibodies. Sera are serially diluted and mixed with known quantities of HSV. These samples are diluted in diluent comprising Eagle's MEM with HBSS containing 2 mM glutamine, 2% FBS, and PEG (e.g., 6% PEG 8000). However, it is also contemplated that other diluents will find use in the present method, including diluents containing different concentrations and types of PEG, as appropriate for the virus and assay system used). These samples are added to cell monolayers containing cells capable of producing an enzyme such as (3-galactosidase upon infection with HSV (e.g., ELVIS™ cells, Diagnostic Hybrids). Following overnight incubation under standard cell culture conditions, the monolayers are lysed and the enzyme activity is measured using chromogenic or luminogenic methods.

A positive response to the vaccine is indicated by the lowest dilution of postvaccination serum which neutralizes HSV in the sample (i.e., as indicated by a low OD. or luminescence value, in comparison with the preimmune control).

In summary, the present invention provides numerous advances and advantages over the prior art, including the avoidance of radioactivity, in combination with the advantages of ease of use, reliability, sensitivity, specificity, cost-effectiveness, and reproducibility.

Example 10

Construction Chimeric TSH-R Plasmids

This example presents one embodiment of constructing a cell line comprising a chimeric TSH-R receptor for detecting Graves' disease autoantibodies.

Plasmid Construction

A plasmid comprising a first nucleic acid sequences encoding a TSH-R chimeric receptor and a second nucleic acid sequence encoding a neomycin resistant gene was ligated to a luciferase gene and a glycoprotein hormone alpha subunit promoter.

Human Glycoprotein Alpha Subunit Promoter Cloning

Chromosomal DNA was isolated from human embryonic kidney cells using a QIAGEN RNA/DNA kit (QIAGEN Cat#14123.) Glycoprotein alpha subunit promoter fragments were amplified by PCR using the isolated chromosomal DNA as the PCR template and the 2 pairs of oligo-nucleotide primers shown below:

```
                                          (SEQ ID NO: 1)
5'PCR primer:
5'-GAGCTC ATG TGT ATG GCT CAA TAA AAT TAC GTA
CAA AGT GAC AGC-3'

(SEQ ID NO: 2)
3' PCR primer:
5'-AGATCT TCG TCT TAT GAG TTC TCA GTA ACT GCA
GTA TAA TGA AGT-3'.
```

A Sac I restriction site was added to the 5' end of the 5' PCR primer while a Bgl II restriction site was added to the 5' end of the 3' PCR primer (both shown as underlined sequence). For PCR amplification, BD Advantage 2 Polymerase Mix (BD Bioscience Palo Alto Calif.) was used and PCR reactions were performed in a thermal cycler (Eppendorf Mastercycler Personal, Germen.). Forty cycles were carried out at 94° C. for 30 seconds to denature the DNA. Samples were then annealed to the primers in the thermalcycler at 63° C. for 30 seconds, and the extension was induced at 68° C. for 1 minute 30 seconds per cycle. Two amplicons (1.2 kb and 0.6 kb) were cloned into the plasmid vector pcDNA2.1 (Invitrogen, Carlsbad, Calif.) and sequenced using the BigDye Terminator v3.0 Cycle Sequencing method on an ABI 377 automated sequencer (Davis Sequencing Inc.).

Construction of Plasmid pGHP/Luc

The human glycoprotein alpha subunit promoter was isolated from vector pcDNA2.1 by restriction cleavage with Sac I and Bgl II. The resulting 316 bp fragment was then subcloned into the Sac I/Bgl II site of the pGL2 enhancer plasmid (Promega, Madison, Wis.) for construction of a plasmid named pGHP/Luc.

Construction of Plasmid pMc4-neo

The neomycin resistance gene for antibiotic selection (positive clone selection) was isolated from vector pMC 1 (Stratagene Cedar Creek, Tex.) with restriction enzymes of XhoI and HicII. The resulting fragment was then subcloned into the XbaI site of plasmid pMc4 that contains the TSHR/LH chimeric receptor driven by the SV40 promoter (from Dr. Leonard Kohn.) The final plasmid was named pMc4-neo.

Construction of Plasmid pMc4-Bsd

The antibiotic selection gene Blastocidin, isolated from vector pCMV/Bsd (Invitrogen, Carlsbad, Calif.) with restriction enzymes XhoI and XbaI, was subcloned into the XbaI site of plasmid pMc4 which contains the TSHR/LH chimeric receptor. Tahara et al., "Immunoglobulins From Graves' Disease Patients Interact With Different Sites On TSH Receptor/LH/CG Receptor Chimeras Than Either TSH Or immunoglobulins From Idiopathic Myxedema Patients" *Biochem Biophys Res Comm* 179:70-77 (1991). The final plasmid was named pMc4-Bsd.

Construction of Plasmid pMc4-GHP/Luc

The human glycoprotein alpha subunit promoter, with a firefly luciferase reporter gene, was isolated from vector pMc4/Luc following restriction cleavage by SmaI and AccI. The isolated DNA fragment was then subcloned into the PfoI site of pMc4-neo plasmid. The final plasmid was named pMV4-GHP/Luc.

Example 11

Mammalian Cell Selection

Seven different mammalian cell lines were tested to select the cell line that had the lowest cyclic AMP basal level and highest potential inducible levels. The results demonstrated that the CHO and RD cells showed the lowest cyclic AMP basal activity and the highest potential inducible level. This empirical research approach maximizes the assay sensitivity by proper selection of cell culture type. For example, a lower cyclic AMP basal level increases the sensitivity of the luciferase assay. Also, the highest induced expression of cyclic AMP improves the accuracy of the luciferase assay.

Example 12

Transfection/Selection of a CHO Cell Line with Chimeric TSH-R Plasmid

This example describes the permanent transfection of CHO cells.

Chinese Hamster Ovary cell line (CHO-K1; ATCC Number: CCL-61, Manassas Va.) was transfected with a linearized (Xmn1) pMc4-GPH/Luciferase plasmid using HyFect® (Denville Scientific, Metuchen, N.J.) according to the manufacturer's instructions. The CHO-K1 cells were then grown in Ham's F12 Medium with 10% (v/v) fetal bovine serum and nine essential amino acids at 37° C. in a humidified atmosphere containing 5% $CO_2$. Twenty four hours after the transfection, the cells were combined and planted into a 96 well plate and selected with 0.5 mg/ml G418 in Ham's F12 Medium with 10% FBS.

Example 13

Transfection/Selection of an RD Cell Line with Chimeric TSH-R Plasmid

This example describes the transfection of a Human Rhabdomyosarcoma (RD) (ATCC Number: CCL-136.) cell line with two plasmids, pGHP/Luc and pMc4-Bsd, in series to facilitate detection.

RD cells were transfected with the linearized pGPH/Luc (Sca1) plasmid using HyFect (Denville Scientific, Metuchen, N.J.) according to the manufacturer's instructions. The cells were selected with 0.5 mg/ml of neomycin. The optimal clone from this transfection and selection was then transfected with the linearized plasmid pMc4-Bsd. After transfection, the cells were selected with both neomycin (0.5 mg/ml) and blasticidin (5 µg/ml.) to produce the final RD recombinant cell line.

All CHO and RD antibiotic resistant clones were tested with TSI-positive and normal serum to select the clone which can be used for the detection of TSI. The TSI induction positive clone was subjected to the limiting dilution cloning to further select a single clone.

The final clones have the ability to diagnose Graves' disease and/or monitor the drug treatment of patients with Graves' disease with higher sensitivity than the current product on the market. These cell lines show good stability, having been passaged more than ten times, and continue to show very similar performance characteristics.

Example 14

Induction of Cell Lines with TSI Containing Serum

CHO cells from freezer vials were diluted and grown in growth media (Ham's F12 Medium with 10 (v/v) % fetal bovine serum and nine essential amino acids) for 16 hours at 37° C. and 5% $CO_2$. After 16 hours the media was removed and the CHO cells were rinsed and refed with 100 µl/well "starvation" HBSS medium. The CHO cells were then incubated for 22-24 hours. Following incubation the media was removed and CHO cells were rinsed and refed with 100 μl/well reaction buffer. The CHO cells were then induced with a 1:11 dilution of patient serum in reaction buffer containing BSA, PEG, sucrose, glucose, and salts (Diagnostic Hybrids Catalog number 40-300500;) for 4 hours at 37° C. and 5% $CO_2$.

RD cells were grown in Eagles Minimal Essential Medium (EMEM) with 10 (v/v) % fetal bovine serums at 37° C. and 5% $CO_2$ for 16-24 hours. RD cells were then directly induced with patient serum in reaction buffer (Diagnostic Hybrids Catalog number 40-300500) for 4 hours at 37° C. and 5% $CO_2$.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the following claims.

Example 15

Effect of Dexamethasone on Starved CHO-RMc4luc Cells

CHO-Rluc (041307A) and CHO-RMc4luc (062707, P8, 3e6/ml) cells were each brought up in 5 ml CHO growth media. From this stock of cells enough was taken out and aliquoted into 6 tubes so that there would be 66,666 cells/well for CHO-Rluc assay and 50,000 cells/well for the CHO-RMc4luc assay for each dexamethasone concentration (100, 50, 40, 25, 12.5, and 0 μM). The dexamethasone stock was 500 μM in CHO-growth media. All dexamethasone was made fresh. These vials were spun down and the cells were brought up in the different concentrations of dexamethasone in CHO growth media.

Cells were then grown for 24 hours, rinsed with starvation media, and then incubated in dexamethasone-containing starvation media that contained the same for 24 hours. The cells were then rinsed with reaction buffer and serum (diluted 1:11) was added to 100 μl of reaction buffer already in the well. Serums used were: i) reference 121506R; ii) PC 121506P; and iii) patient #18 TSI serum. Reference and Patient #18 serums were both treated the same and incubated with all 6 concentrations of dexamethasone.

After 4 hours of induction the plates were lysed with 75 ul of Bright Glo®, lysed for 5 minutes, and then read on a Veritas luminometer.

Example 16

Comparison of Starvation Periods to Dexamethasone Treatment

Nine (9) human serum samples were prepared where four (4) samples were known positive for Grave's Disease and five (5) samples were known negative for Grave's disease. Each of the nine samples was tested in each condition of both the Non-Starvation/Dexamethasone Protocol and the Starvation Protocol.

1. Non-Starvation/Dexamethasone Protocol

Three cell plates were analyzed using a CHO-RMc4 protocol. Plate 1: CHO-Mc4luc cells (4e6 cells/plate)+Growth Medium containing 40 μM dexamethasone in CHO-Mc4 Reaction Buffer. Plate 2: CHO-RMc4luc cells (4e6 cells/plate)+Growth Medium without 40 μM dexamethasone in CHO-Mc4 Reaction Buffer. Plate 3: CHO-Rluc cells (4e6 cells/Plate)+Growth Medium without 40 μM dexamethasone in CHO-Rluc Reaction Buffer Each plate underwent a 16 hour growth period, a 3 hour induction period, and a 10 minute lysis period.

2. Starvation Protocol

Figure 16:
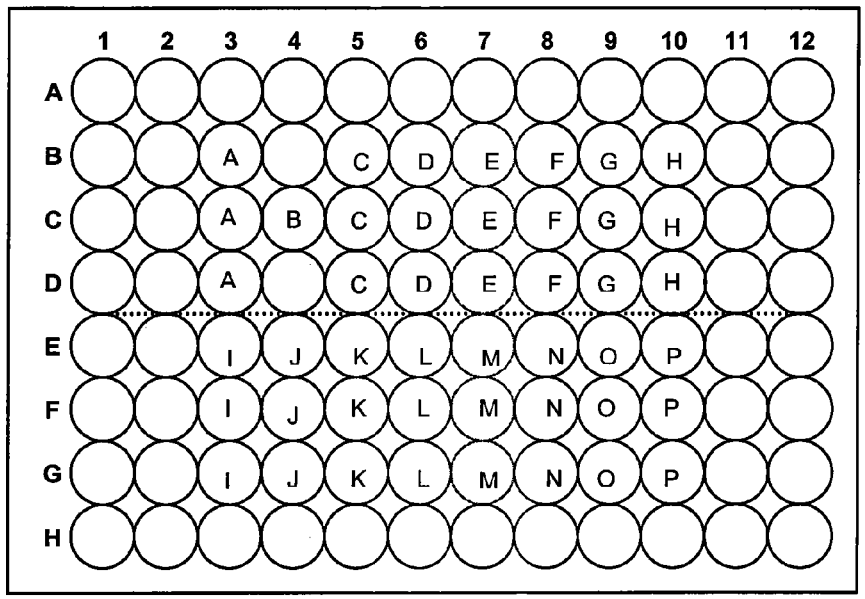
FIG. 16 illustrates a representative arrangement of TSI samples in a testing plate.

Three plates were analyzed using a CHO-R protocol. Plate 1: CHO-RMc4 cells (4e6 cells/plate)+Growth Medium containing 40 μM dexamethasone in CHO-Mc4 Reaction Buffer. Plate 2: CHO-RMc4luc cells (4e6 cells/plate)+Growth Medium without 40 μM dexamethasone in CHO-Mc4 Reaction Buffer. Plate 3: CHO-Rluc cells (4e6 cells/Plate)+Growth Medium without 40 μM dexamethasone in CHO-Rluc Reaction Buffer. The sample arrangement for each protocol was configured identically. See, FIG. 16.

Each plate underwent a 24 hour growth period, a 24 hour starvation period, a 4 hour induction period, and a 5 minute lysis period. The luminosity for each sample was measured using a Veritas luminometer.

Example 17

Comparison of Alternate Glucocortoids with Dexamethasone

This example provides data showing that improved sensitivity of a CHO-RMc4 assay is not limited to the substitution of a Starvation medium period with dexamethasone (Dex) in accordance with Example 16. These data demonstrate that four alternative glucocorticoids (GCs) have equivalent effects in improving signal intensity.

Four GCs were examined in this study: i) Prednisone (Sigma); ii) Hydrocortisone (Sigma); iii) Fluticasone Propionate (Sigma); and iv) Cortisone (Sigma). A stock concentration (100 mM) of each GC was made in DMSO. 1:10 (10 mM) and 1:100 (1 mM) dilutions, in DMSO, were then made from the 100 mM stock. All DMSO/GC stocks were clear with no visible precipitate.

Growth Media containing different concentrations of each GC were made as follows: i) 100 μM GC Medium: 5 μL of 100 mM GC Stock+5 mL SR097 (w/o Dex); ii) 50 μM GC Medium: 2.5 μL of 100 mM GC Stock+5 mL SR097 (w/o Dex); iii) 10 μM GC Medium: 5 μL of 10 mM GC Stock+5 mL SR097 (w/o Dex); iii) 1 μM GC Medium: 5 μL of 1 mM GC Stock+5 mL SR097 (w/o Dex); and iv) 0.1 μM GC Medium: 0.5 μL of 1 mM GC Stock+5 mL SR097 (w/o Dex). A 40 μM dexamethasone control sample was run in comparison to these various concentrations of the alternative glucocorticoids. Additional controls included Growth Medium containing 1 μl/ml dimethylsulfoxide (DMSO) as a solvent control and Growth Medium without any glucocorticoids.

Each assay was performed by using two (2) microwell plates for each glucocorticoid tested. The sample layouts for each plate are identified below:

A. Plate One

| A | B | C | D | E | F | G | H |
|---|---|---|---|---|---|---|---|
| I | J | K | L | M | N | O |   |

A  Positive (GM containing dexamethasone)
B  Reference (GM containing dexamethasone)
C  Normal (GM containing dexamethasone)
D  Positive (GM containing 100 μM glucocorticoid)
E  Reference (GM containing 100 μM glucocorticoid)
F  Normal (GM containing 100 μM glucocorticoid)
G  Positive (GM containing 50 μM glucocorticoid)

-continued

| | |
|---|---|
| H | Reference (GM containing 50 μM glucocorticoid) |
| I | Normal (GM containing 50 μM glucocorticoid) |
| J | Positive (GM containing 10 μM glucocorticoid) |
| K | Reference (GM containing 10 μM glucocorticoid) |
| L | Normal (GM containing 10 μM glucocorticoid) |
| M | Positive (GM containing 1 μM glucocorticoid) |
| N | Normal (GM containing 1 μM glucocorticoid) |
| O | Reference (GM containing 1 μM glucocorticoid) |

B. Plate Two

| | | | | | | |
|---|---|---|---|---|---|---|
| P | Q | R | S | T | U | V | W |
| X | Y | Z | AA | | | |

| | |
|---|---|
| P | Positive (GM containing dexamethasone) |
| Q | Reference (GM containing dexamethasone) |
| R | Normal (GM containing dexamethasone) |
| S | Positive (GM containing 0.1 μM glucocorticoid) |
| T | Reference (GM containing 0.1 μM glucocorticoid) |
| U | Normal (GM containing 0.1 μM glucocorticoid) |
| V | Positive (GM containing DMSO) |
| W | Reference (GM containing DMSO) |
| X | Normal (GM containing DMSO) |
| Y | Positive (GM only) |
| Z | Reference (GM only) |
| AA | Normal (GM only) |

The raw data is presented below. See Table 8.

TABLE 8

Alternative Glucocortiocids - Raw Data

| Condition | Δ (positive - normal) RLU | Δ (positive - normal) SRR % s |
|---|---|---|
| Fluticasone Proprionate | | |
| 0.1 μM | 9768 | 161 |
| 1 μM | 8806 | 148 |
| 10 μM | 8774 | 168 |
| 50 μM | 6996 | 137 |
| 100 μM | 6366 | 155 |
| Prednisone | | |
| 0.1 μM | 8717 | 150 |
| 1 μM | 8219 | 133 |
| 10 μM | 8429 | 142 |
| 50 μM | 8107 | 165 |
| 100 μM | Not Determined | Not Determined |
| Hydrocortisone | | |
| 0.1 μM | 9889 | 158 |
| 1 μM | 9149 | 155 |
| 10 μM | 9757 | 153 |
| 50 μM | 8950 | 178 |
| 100 μM | 8348 | 180 |
| Cortisone | | |
| 0.1 μM | 10494 | 169 |
| 1 μM | 9474 | 151 |
| 10 μM | 9847 | 151 |
| 50 μM | 8738 | 162 |
| 100 μM | 8106 | 176 |
| Controls | | |
| 40 μM Dexamethasone | 9375 | 282 |
| GM + 1 μL/ml DMSO | 9467 | 141 |
| GM w/o Dexamethasone | 9010 | 157 |

---

We claim:

1. A method, comprising:
   a) providing;
      i) a cell line comprising a stably transfected recombinant plasmid vector encoding a chimeric TSH receptor and a reporter gene, wherein said chimeric TSH receptor is encoded by a nucleic acid sequence comprising SEQ ID NO: 3;
      ii) a cell culture medium compatible with said cell line; and
      iii) a serum sample derived from a patient suspected of having Graves' disease;
   b) contacting the serum sample with the cell line and the medium under conditions such that a reporter gene emits a detectable signal upon induction by a TSH receptor-specific stimulating auto-antibody.

2. The method of claim 1, wherein an intensity of said detectable signal correlates with clinical activity.

3. The method of claim 1, wherein an intensity of said detectable signal correlates with the clinical severity of Graves' disease.

4. The method of claim 3 wherein said clinical severity is assessed on the basis of diplopia, proptosis, visual acuity, ocular motility, optic neuropathy, or extra-ocular muscle thickness.

5. The method of claim 3, wherein said clinical severity is measured on the basis of the NOSPECS score.

6. The method of claim 1, wherein an intensity of said detectable signal correlates with Graves' orbitopathy.

7. The method of claim 1, wherein the thyrotropin stimulating hormone receptor autoantibody concentration correlates with clinical activity.

8. The method of claim 1, wherein the thyrotropin stimulating hormone receptor autoantibody concentration correlates with the clinical severity of Graves' disease.

9. The method of claim 8, wherein the clinical severity is assessed on the basis of diplopia, proptosis, visual acuity, ocular motility, optic neuropathy, or extra-ocular muscle thickness.

10. The method of claim 8, wherein said clinical severity is measured on the basis of the NOSPECS score.

11. The method of claim 1, wherein the thyrotropin stimulating hormone receptor autoantibody concentration correlates with Graves' orbitopathy.

12. The method of claim 1, wherein said culture medium contains a glucocorticoid.

13. The method of claim 1, wherein said reporter gene is luciferase.

14. A method, comprising:
   a) providing:
      i) a cell line comprising a stably transfected recombinant plasmid vector encoding a chimeric TSH receptor and a reporter gene, wherein said chimeric TSH receptor is encoded by a nucleic acid sequence comprising SEQ ID NO: 3;
      ii) a cell culture medium compatible with said cell line; and
      iii) an undiluted serum sample and a diluted serum sample from a patient suspected of having Graves' disease;
   b) contacting the undiluted serum sample and diluted serum sample with the cell line and the medium under conditions such that a reporter gene emits a detectable signal upon induction by a TSH receptor-specific stimulating auto-antibody.

15. The method of claim 14, wherein said method further comprises step c) comparing an intensity of said detectable signal from said undiluted sample with said diluted sample.

16. The method of claim 15, wherein said activity from undiluted and diluted serum demonstrates a comparative reactivity profile indicative of clinical activity.

17. The method of claim 15, wherein said activity from undiluted and diluted serum demonstrates a comparative reactivity profile indicative of severity of Graves' disease.

18. The method of claim 15, wherein said activity from undiluted and diluted serum demonstrates a comparative reactivity profile indicative for Graves' orbitopathy.

19. The method of claim 14, wherein said culture medium contains a glucocorticoid.

20. The method of claim 14, wherein said reporter gene is luciferase.

21. A method, comprising:
   a) providing;
      i) a cell line comprising a stably transfected recombinant plasmid vector encoding a chimeric TSH receptor and a reporter gene, wherein said chimeric TSH receptor is encoded by a nucleic acid sequence comprising SEQ ID NO: 3;
      ii) a cell culture medium compatible with said cell line;
      iii) a first undiluted serum sample obtained from a patient having Graves' disease prior to being treated with drug therapy; and
      iv) a second undiluted serum sample obtained from a patient having Graves' disease after being treated with drug therapy;
   b) diluting a portion of said first serum to create a diluted first serum sample; and
   c) contacting said undiluted first serum sample and said diluted first serum sample with the cell line and the medium under conditions such that a reporter gene emits a detectable signal upon induction by a TSH receptor-specific stimulating auto-antibody.

22. The method of claim 21, wherein said method further comprises step d) diluting a portion of said second serum sample to create a diluted second serum sample; and e) contacting the undiluted second serum sample and diluted second serum sample with the cell line and the medium under conditions such that a reporter gene emits a detectable signal upon induction by a TSH receptor-specific stimulating auto-antibody.

23. The method of claim 22, further comprising step f) comparing the activity of the expressed reporter gene from the first and second serum samples.

24. The method of claim 23, wherein the comparative reactivity profiles of the first and second serum samples serve as an indication of patient response to drug treatment.

25. The method of claim 21, wherein said culture medium contains a glucocorticoid.

26. The method of claim 21, wherein said reporter gene is luciferase.

27. The method of claim 21, wherein the drug received by said patients is selected from the group consisting of anti-thyroid drugs, steroids, T4, and immunosuppressive drugs.

28. The method of claim 21, wherein the thyrotropin stimulating hormone receptor auto-antibody concentration is used to monitor drug treatment.

* * * * *